United States Patent
McQuade et al.

(10) Patent No.: US 6,172,262 B1
(45) Date of Patent: Jan. 9, 2001

(54) AMPHIPHILIC AGENTS FOR MEMBRANE PROTEIN SOLUBILIZATION

(75) Inventors: D. Tyler McQuade, Cambridge, MA (US); Samuel H. Gellman, Madison, WI (US)

(73) Assignee: Wisconsin Alumni Research Foundation, Madison, WI (US)

( * ) Notice: Under 35 U.S.C. 154(b), the term of this patent shall be extended for 0 days.

(21) Appl. No.: 09/238,522

(22) Filed: Jan. 27, 1999

(51) Int. Cl.$^7$ .................................................. C07C 233/05
(52) U.S. Cl. .................. 564/182; 564/181; 564/184; 564/190; 564/215; 564/224; 530/407; 530/825; 510/382; 436/4.1
(58) Field of Search ..................................... 564/181, 182, 564/184, 215, 224, 190; 436/4.1; 530/407, 825; 510/382; 106/135.1, 155.21

(56) References Cited

U.S. PATENT DOCUMENTS

| | | |
|---|---|---|
| 3,947,451 | 3/1976 | Jönsson et al. . |
| 4,110,263 * | 8/1978 | Lindemann et al. .................. 252/545 |
| 4,174,296 * | 11/1979 | Kass ...................... 252/312 |

OTHER PUBLICATIONS

Alder, R.W.;Maunder, C.M.;Orphen, A.G. Tetrahedron Lett. 1990, 31:6717–6720.

attwood, D., Micelle formation by some antihistamines in aqueous solution. Letters to the Editor, *J. Pharmac.*, 1972, 24:751–752.

Attwood, D. and Udeala, O.K., Aggregation of antihistamines in aqueous solution: micellular properties of some diphenylmethane derivatives, 1974, *J. Pharm. Pharmac.* 26:854–860.

Attwood, D. and Udeala, O.K., Aggregation of Antihistamnies in Agueous Solution. Self–Association of Some Pyridine Derivatives, 1975, *The Journal of Physical Chemistry*, Vol. 70, No. pp. 889–892.

Attwood, D. and Udeala, O.K., Aggregation of antihistamnies in aqueous solution. The Effect of electrolyte on the micellar properties of some diphenylmethane derivatives, 1975, *J. Pharmac.*, 27:395–399.

Attwood, D., Aggregation of antiacetylcholine drugs in aqueous solution: micellular properties of some diphenyl-methane derivatives, 1976, *J. Pharm. Pharmac.* 28:407–409.

Attwood, D., Micellar and Nonmicellar Association of Anti-acetylcholine Drugs in Aqueous Solution, *The Journal of Physical Chemisgtry*, 1976, Vol. 80, No. 18, pp. 1984–1987.

Azema, J.; Chebli, C.; Bon, M.; Rico–Lattes, I.; Lattes, A. *J. Carbo. Chem.* 1995, 14:805–817.

Bumagin, N.A.; Luzikova, E. V.; Beletskaya, I.P. Russian *J. Org. Chem.* 1996, 31:1480–1486.

Champaigne, E.; Mais, D.; Yokley, E.M. *Syn Comm.* 1974, 4:379.

Cope, A.C.; Hofmann, C.M.; Wyckoff, C.; Hardenbergy, E. *J. Am. Chem.* Soc. 1941, 63:3452.

Davis, A.P.; Orchard, M.G. *J. Chem. Soc. Perkins Trans.* I 1993:919–924.

Luitjes, H.; Schakel, M.; Klumpp, G.W., *Syn. Comm.* 1994, 24:2257–2261.

Nugebauer, J.M. (1990), *Methods in Enzymology*, 182:239–253.

Patai, S.; Dayagi, S. *J. Chem. Soc.* 1962, 717.

Rabjohn, N.; Phillips, L. V.; Defeo, R.J., Unsymmetrical Tetraalkylmethanes. IV. General Method of Synthesis of Tetraalkylmethanes, *J. Org. Chem.* 1959, 24:1964–1969.

Schafmeister, C.E.; Miercke, L.J.W.; Stroud, R.M. *Science* 1993, 262:734–738.

Schleicher et al. (Schleicher, A.; Franke, R.; Hofmann, K.P.; Finkelmann, H.; Welte, W. *Biochemistry* 1987, 26:5908–5916.

* cited by examiner

*Primary Examiner*—Shailendra Kumar
(74) *Attorney, Agent, or Firm*—DeWitt Ross & Stevens S.C.

(57) ABSTRACT

Disclosed are amphiphilic compounds comprising Formula I:

Formula I:

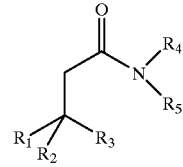

wherein $R_1$, $R_2$, and $R_3$ are $C_2$–$C_{12}$ straight or branched alkyl; unsubstituted phenyl, biphenyl, $C_3$–$C_8$ cycloalkyl, or $C_3$–$C_8$ cycloalkenyl; or phenyl, biphenyl, $C_3$–$C_8$ cycloalkyl, or $C_3$–$C_8$ cycloalkenyl substituted with one, two, or three $C_1$–$C_6$ straight or branched alkyl groups; or $R_1$ and $R_2$ combined are $C_3$–$C_8$ cycloalkyl, $C_3$–$C_8$ cycloalkenyl; or $C_3$–$C_8$ cycloalkyl or $C_3$–$C_8$ cycloalkenyl substituted with one, two, or three $C_1$–$C_6$ straight or branched alkyl groups; one of $R_4$ or $R_5$ is selected from the group consisting of $C_2$–$C_6$-straight or branched alkyl-(dimethyl-N-oxide), alkyl-(dimethylamine), alkyl-(trimethylammonium), alkyl-glucosyl, alkyl-maltosyl, glucosyl, maltosyl, and polyethylene(glycosyl); the other of $R_4$ or $R_5$ is selected from the group consisting of H, $C_2$–$C_6$ straight or branched alkyl or alkenyl, $C_2$–$C_6$-straight or branched alkyl-(dimethyl-N-oxide); alkyl-(dimethylamine), alkyl-(trimethylammonium), alkyl-glucosyl, alkyl-maltosyl, glucosyl, maltosyl, and polyethylene(glycosyl); and salts thereof. The compounds are detergents useful in the solubilization of membrane-bound proteins.

17 Claims, No Drawings

AMPHIPHILIC AGENTS FOR MEMBRANE PROTEIN SOLUBILIZATION

This invention was made with United States government support awarded by the following agencies: NSF Grant No. 9224561. The United States has certain rights in this invention.

FIELD OF THE INVENTION

The invention is directed to a genus of amphiphilic detergents which readily solubilize membrane-bound proteins.

DESCRIPTION OF THE PRIOR ART

The currently accepted model for the molecular structure of a cell membrane is referred to as the fluid mosaic model. In this view, the lipid bilayer of a cell membrane acts as a "sea" in which membrane-bound proteins are dispersed. Membrane-bound proteins are those proteins which associate with the lipid bilayer of a cell membrane. Membrane-bound proteins regulate or otherwise play a role in a vast number of cellular functions, including cell-to-cell signalling, mitosis, viral infectivity, etc. Elucidating the structure and function of membrane-bound proteins is therefore critical to a complete understanding of overall cellular functionality.

However, separating a membrane-bound protein from the lipid components of a bilayer without destroying the essential structure and functionality of the protein is often difficult, if not impossible. This, in turn, makes it equally difficult or impossible to determine the structure of the membrane-bound protein by X-ray crystallography because the impure and/or denatured protein cannot be induced to crystallize.

The lipids which form cell membranes are amphiphilic: each lipid molecule contains a polar headgroup and a non-polar region. Likewise, detergents, as a class of compounds, also contain a polar region and a non-polar region. Detergents spontaneously aggregate in aqueous solution into micelles, spherical structures in which the non-polar portions of the detergent molecules point to the center of the structure and the polar regions define the spherical surface of the structure. Detergent micelles are dynamic structures which readily interact with and solubilize hydrophobic material. It is this characteristic which makes detergents invaluable cleaning agents.

Detergent micelles and monomeric detergents can also disrupt lipid bilayers. The disruption of a membrane bilayer by a detergent has been proposed to involve first the insertion of the hydrophobic domain of the detergent into the hydrophobic domain of the membrane bilayer, followed by aggregation of the inserted detergent molecules within the membrane. The regions of aggregated detergent are thought to alter the curvature of the bilayer, causing it to degrade into mixed detergent-lipid aggregates. With sufficient concentration of detergent, the process continues until the membrane bilayer has been completely dissolved and all that remains are mixed detergent-lipid micelles.

This ability to disrupt lipid bilayers makes detergents useful for solubilizing membrane-bound proteins and separating the proteins from the lipid components of the cell membrane. However, crystallizing a detergent-solubilized membrane protein into a structure of sufficient regularity to enable high-resolution X-ray crystallography remains extremely problematic. Despite much effort, well-ordered membrane protein crystals are very difficult to obtain using conventional detergents.

To the inventors' knowledge, only three accounts using rigid amphiphile molecules for solubilization of membrane proteins are found in the prior art. In the first example, Schleicher et al. (Schleicher, A.; Franke, R.; Hofmann, K. P.; Finkelmann, H.; Welte, W. *Biochemistry* 1987, 26:5908–5916) found that a biphenyl-based detergent could maintain the solubility of rhodopsin that had initially been solubilized with nonanoyl-N-methylglucamide. The authors suggest that the rigid structure of the detergent provides a hydrophobic core similar to that provided by a lipid bilayer. However, the authors never suggest that the rigidity of the detergent could allow for more facile crystallization of rhodopsin.

The second example of rigid amphiphiles are peptitergents (see Schafmeister, C. E.; Miercke, L. J. W.; Stroud, R. M. *Science* 1993, 262:734–738). Peptitergents are rigid α-helical amphiplhilic peptides that have been proposed as solubilization and crystallization agents. However, only bacteriorhodopsin has proven to have long-term stability (weeks) when solubilized by a peptitergent. There are no reports to date of a membrane protein having been crystallized using a peptitergent.

The third example of rigid amphiphiles is modified bile acids like 3-{(3-cholamidopropyl)dimethylammonio}-2-hydroxy-1-propane sulfonate (CHAPSO). See, for example, Azema, J.; Chebli, C.; Bon, M.; Rico-Lattes, I.; Lattes, A. *J. Carbo. Chem.* 1995, 14:805–817.

SUMMARY OF THE INVENTION

The invention is directed to amphiphilic compounds comprising Formula I:

Formula I:

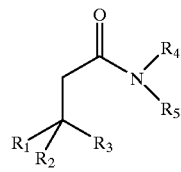

wherein $R_1$, $R_2$, and $R_3$ are independently selected from the group consisting of $C_2$–$C_{12}$ straight or branched alkyl; unsubstituted phenyl, biphenyl, $C_3$–$C_8$ cycloalkyl, and $C_3$–$C_8$ cycloalkenyl; and phenyl, biphenyl, $C_3$–$C_8$ cycloalkyl, and $C_3$–$C_8$ cycloalkenyl substituted with one, two, or three $C_1$–$C_6$ straight or branched alkyl groups; or $R_1$ and $R_2$ combined are selected from the group consisting of $C_3$–$C_8$ cycloalkyl, $C_3$–$C_8$ cycloalkenyl; and $C_3$–$C_8$ cycloalkyl and $C_3$–$C_8$ cycloalkenyl substituted with one, two, or three $C_1$–$C_6$ straight or branched alkyl groups;

one of $R_4$ or $R_5$ is selected from the group consisting of $C_2$–$C_6$-straight or branched alkyl-(dimethyl-N-oxide), alkyl-(dimethylamine), alkyl-(trimethylammonium), alkyl-glucosyl, alkyl-maltosyl, glucosyl, maltosyl, and polyethylene(glycosyl);

the other of $R_4$ or $R_5$ is selected from the group consisting of H, $C_2$–$C_6$ straight or branched alkyl or alkenyl, $C_2$–$C_6$-straight or branched alkyl-(dimethyl-N-oxide); alkyl-(dimethylamine), alkyl-(trimethylammonium), alkyl-glucosyl, alkyl-maltosyl, glucosyl, maltosyl, and polyethylene(glycosyl); and salts thereof.

While not being confined to any particular mechanism, the present inventors hypothesize that the flexibility of conventional detergents is what makes them antithetical to the formation of well-ordered crystals of membrane protein-detergent complexes. When a membrane protein-detergent complex crystallizes, detergent is trapped within the crystal lattice in high concentrations. It is believed that the large, disordered domains of conventional detergent complexed to the membrane protein contribute in large measure to the difficulty of growing membrane protein crystals in the first instance, and also contribute to the disorder of proteins within the lattice when crystals are formed.

The invention is therefore directed to amphiphiles as noted above having limited flexibility within their hydrophobic domains. The limited flexibility of the molecules is believed to enhance their ability to solubilize and crystallize membrane-bound proteins into well-order crystals. In short, it is believed that the detergent molecules described herein are sufficiently rigid to minimize intramolecular disorder, long enough to span the gaps within a lattice formed by protein-protein interactions, and yet still sufficiently flexible to maximize the protein-protein contacts which give rise to the lattice structure in a membrane protein-detergent crystal.

The amphiphiles of the present invention can also be used in any application where conventional detergents are utilized. For instance, the amphiphiles of the present invention can be used to lyse cellular membranes. The amphiphiles of the present invention also form micelles in aqueous solution. They can therefore be used to solubilize hydrophobic compounds for dispersion into aqueous solution. More specifically, the subject amphiphiles are useful for solubilizing membrane proteins.

Further aims, objects and advantages of the invention will appear upon a complete reading of the following Detailed Description and attached claims.

DETAILED DESCRIPTION OF THE INVENTION

Abbreviations and Definitions:

BR=Bacteriorhodopsin.

CMC=Critical Micelle Concentration. The concentration of a detergent in an aqueous solution at which the detergent molecules will self-assemble into micelles. Below the CMC, detergents are mostly monomeric; above the CMC, micelle concentration increases linearly with detergent concentration. CMC is dependent upon many factors and is detergent-specific.

DMF=dimethylformamide.

DDAO=dodecylammonium-N-oxide.

DMSO=dimethylsulfoxide.

LDAO=lauryldodecylammonium-N-oxide.

mCPBA=m-chloroperbenzoic acid.

Orange OT=a fluorophore dye.

salts=as used herein, refers to acid-addition salts, such as chlorides, bromides, citrates, malonates, fumarates, etc.

THF=tetrahydrofuran.

The Triphenylmethyl Moiety

Triphenylacetic acid 4.0 has a novel amphiphilic geometry and is commercially available. The sodium salt of triphenylacetic acid 4.1 was synthesized, and the high solubility (210 mM) and high CMC (130 mM), as measured by orange OT uptake, made the compound very attractive.

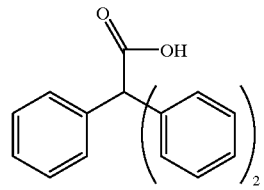

4.0

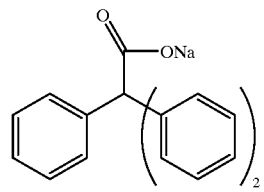

4.1

The triphenylacetic acid moiety was then used to generate detergents for membrane protein solubilization and crystallization.

Attaching one betaine headgroup to 4.1 yielded insoluble products. Attempts to functionalize 4.1 by adding two betaine groups proved unfruitful, likely due to adverse steric interference. Therefore, the one-carbon homologue of 4.0, 3,3,3-triphenylpropionic acid, 4.6. was synthesized by heating a neat mixture of malonic acid and triphenylmethanol, 4.5 (Patai, S.; Dayagi, S. *J. Chem. Soc.* 1962, 717).

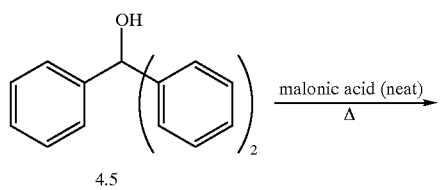

4.5

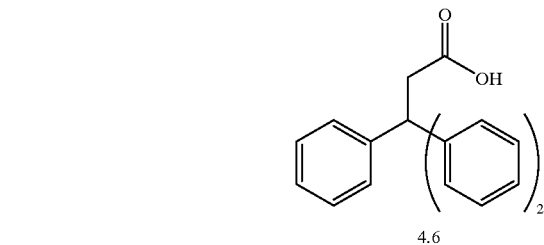

4.6

Functionalization of 4.6 proved to be very easy. Compound 4.8 was synthesized by first generating the acyl chloride with thionyl chloride and condensing it with triamine 4.7. Amido diamine 4.8 provided two sites for further elaboration into water solubilizing groups. Instead of the bis-betaine headgroup, bis-N-oxide 4.10 was synthesized. Bis-N-oxide 4.10 was very soluble in water (>2 M). Bis-N-oxide 4.11 was synthesized in a similar manner; for tris-N- oxide 4.13, the amide carbonyl of 4.8 was reduced and the resulting triamine (4.12) was oxidized:

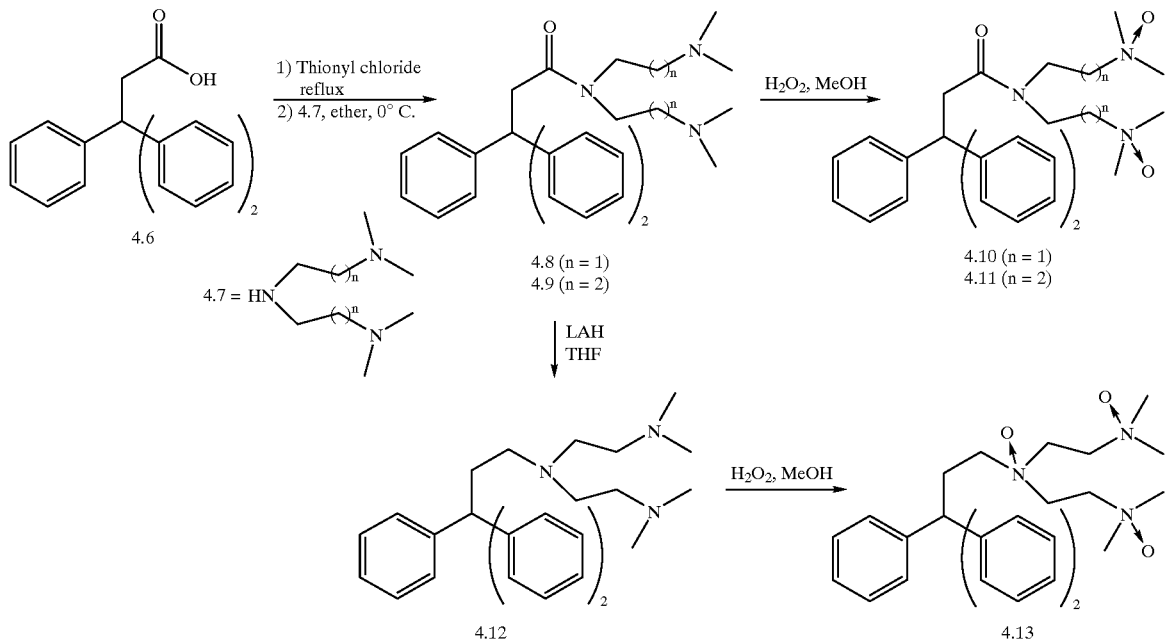

Functionalization of 4.5 with diethanolamine was also successful via condensation of the amine with acyl chloride.

The high aqueous solubility of this first generation of amphiphiles encouraged us to synthesize detergents with even greater hydrophobicity.

It was hypothesized that placement of an alkyl group, such as a tert-butyl group, on one or more of the phenyl groups would not only provide more hydrophobic surface area, but would also provide a long axis to the hydrophobic core which might facilitate entry into the lipid bilayer. Ester 4.16 was treated with 2 equivalents of phenylmagnesium bromide. The resulting alcohol (4.17) was then condensed with neat malonic acid to give acid 4.18, which was treated with thionyl chloride and then with triamine 4.7. The bis-amine was oxidized to bis-N-oxide 4.20:

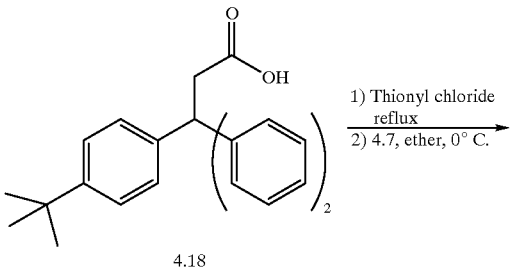

-continued

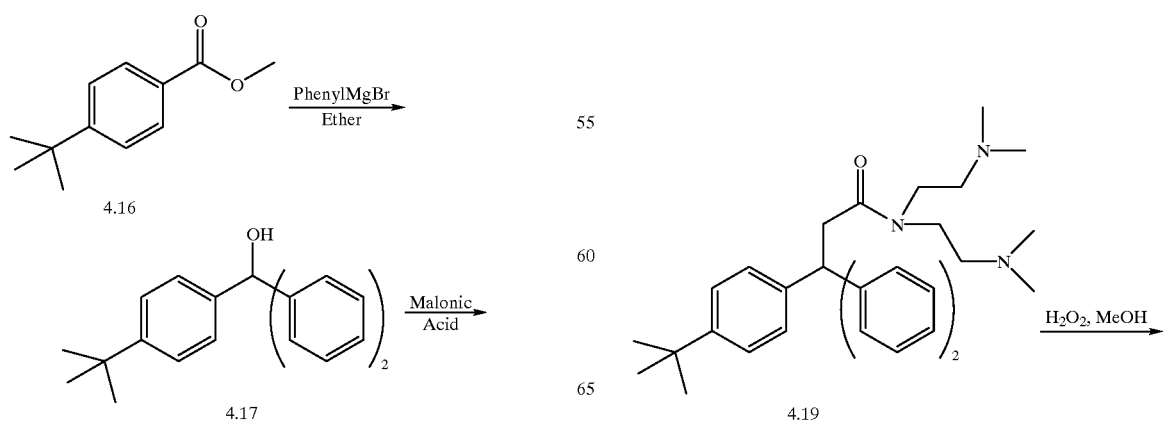

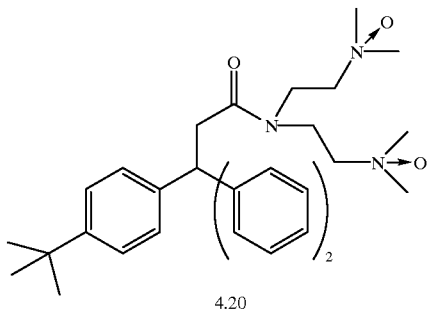

4.20

The CMCs of 4.20 and 4.10 were determined by dye uptake and were found to be about 12.5 mM and about 80 mM, respectively. The addition of the t-butyl group accomplished the goal of increasing the hydrophobic surface area, as indicated by the diminished CMC's.

It was then thought that the quaternary center of 3,3,3-triphenylpropionic acid (4.6) could serve three purposes: 1) The quaternary center would provide an attachment point for hydrophobic groups; that is, the quaternary center would display the headgroup in one direction and hydrophobic tails in the other three directions; 2) the quaternary center would provide a source of intramolecular rigidity; and 3) the quaternary center would force the detergents to be contrafacial (i.e., having the polar headgroup extending essentially perpendicularly from the plane of the hydrophobic domain).

Detergent Synthesis

Synthesis of quaternary carbon centers can be difficult due to steric congestion. As the substitution of a carbon center increases, the difficulty of bimolecular nucleophilic substitution reactions goes up. A tertiary carbon center can readily form a carbocation intermediate and undergo unimolecular nucleophilic substitution, but as the bulk of the substituents increase, the tendency to undergo elimination reactions also increases. Using Michael addition methodology, Rabjohn et al. (Rabjohn, N.; Phillips, L. V.; Defeo, R. J. *J. Org. Chem.* 1959, 24:1964) synthesized a series of carboxylic acids with a quaternary center beta to the carbonyl. Rabjohn's route involved a copper mediated Grignard addition to a cyano-ethylcarboxyl alkylidene, 4.25. The addition product 4.26 was then decarboxylated and the nitrile 4.27 was hydrolyzed:

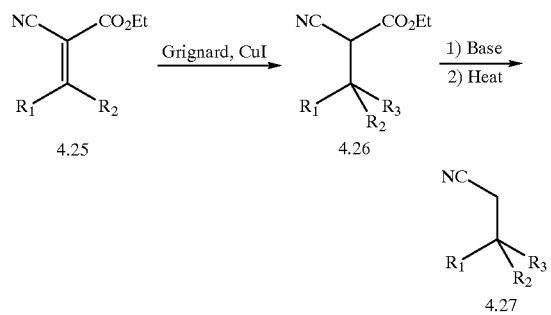

Rabjohn's method was modified to provide a modular route to the amphiphiles of the present invention. Using malononitrile instead of ethyl cyanoacetate will yield, via condensation, a ketone. The dinitrile is less sterically demanding and allows for greater elaboration. The Michael addition to the alkylidene allows the synthesis of quaternary centers with a wide variety of hydrophobic appendages. The resulting dinitrile can be hydrolyzed to the dicarboxylic acid (4.28), hydrolyzed and decarboxylated to the carboxylic acid (4.29) or reduced to the diamine (4.30). These functional groups can then be elaborated to myriad headgroups. The quaternary center provides a tripod appearance; therefore these detergents are called "tripods."

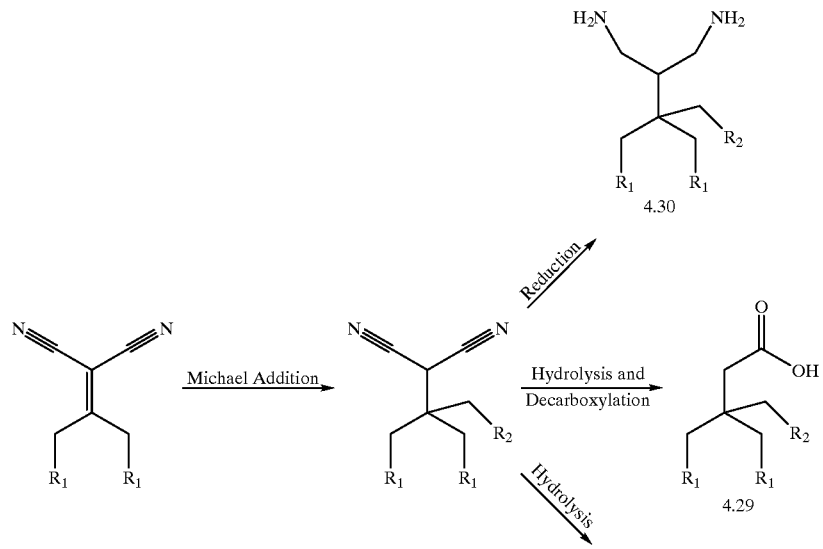

-continued

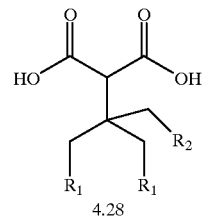
4.28

The quarternary center of the tripid detergent rigidifies the entire skeleton. A tetra-substituted carbon atom limits the allowable torsion angles of the flanking bonds, and conformational restriction extends out two bonds from the quaternary center. See Alder, R. W.; Maunder, C. M.; Orphen, A. G. Tetrahedron Lett. 1990, 31:6717–6720. Alder et al. found that the influence of the quarternary center does not extend to the bond gamma to the quarternary center. Incorporation of a quarternary center in the subject detergents therefore provides the desired rigidity without unduly restricting the intramolecular flexibility of the molecules.

A class of detergents that will be successful for crystallizing many different membrane proteins should optimally have members with varying rigidity. Detergents which are too rigid cannot adequately adapt to fit into the spaces formed when detergent-solubilized membrane proteins come together in a regular lattice. However, the optimum level of rigidity likely differs for each membrane protein. Therefore, a successful class of detergents will contain members that systematically vary in their rigidity. The quaternary center of the subject tripod detergents allows control of the rigidity of the first two bonds extending out from the quaternary center. This limited influence of the quaternary center allows for systematic variation of the rigidity by replacing n-alkyl chains with cyclic or branched hydrocarbons. The ends of two legs of the tripod can also be linked to form a ring:

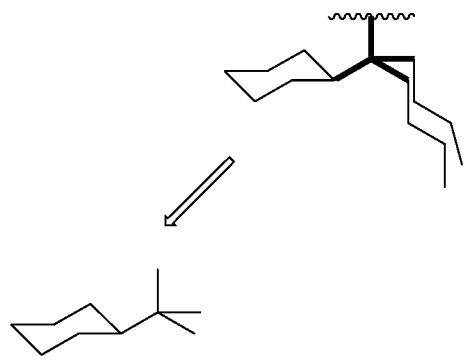

By varying the numbers of cyclic legs, the rigidity of the hydrophobic region of the tripod can be controlled.

Another approach used in the invention to increase the rigidity of a tripod detergent is to use branched chains instead of rings. Strategically placed branch points can be used to control the conformation of acyclic hydrocarbon backbones. In this approach, the avoidance of syn-pentane interactions can be employed to generate a mono-conformational linear alkyl chain. Branched chains will adopt conformations that avoid syn-pentane type interactions. For example, 2,3,4,5-tetramethylhexane (TMH) adopts a single conformation because all other conforma-

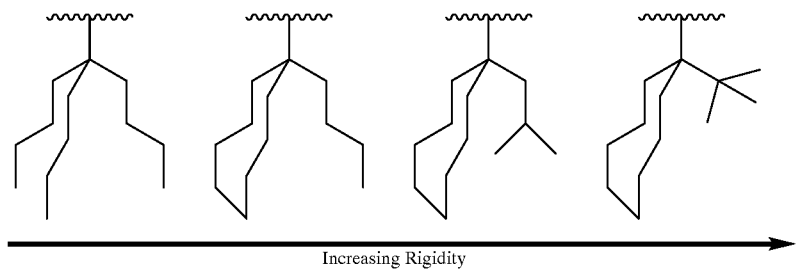

Increasing Rigidity

The quaternary center of the tripod can strongly bias the conformation of a cyclcohexyl ring. Cyclohexyl rings substituted with a t-butyl group strongly favor a chair conformation that places the t-butyl group in an equatorial position to avoid 1,3-diaxial interactions. The following structure illustrates a tripod detergent substituted with a cyclohexane and show the relationship to a t-butyl substituted cyclohexane:

tions contain syn-pentane interations. This approach allows for the construction of long, rigid alkyl chains.

A first series of detergents synthesized using this modular approach are based on the starting material 5-nonanone. The ketone was condensed with malononitrile, using the modified Knovenagel condensation of Cope (Cope, A. C.; Hofmann, C. M.; Wyckoff, C.; Hardenbergy, E. J. Am.

Chem. Soc. 1941, 63:3452). The resulting alkylidiene was reacted with copper (I) iodide and n-butyl, n-hexyl or phenyl magnesium bromide. The resulting dinitriles proved to be difficult to hydrolyze. After trying a number of acidic and basic conditions, a method developed by Patai and Dayagi was employed (Patai, S.; Dayagi, S. *J. Chem. Soc.* 1962:717):

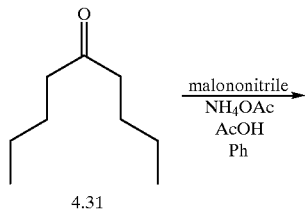

4.31

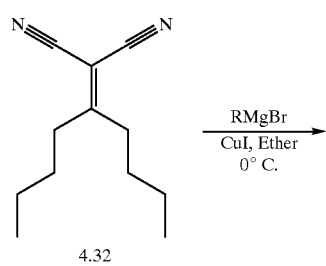

4.32

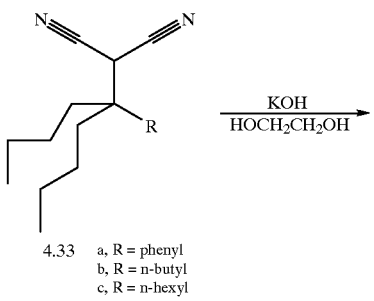

4.33  a, R = phenyl
      b, R = n-butyl
      c, R = n-hexyl

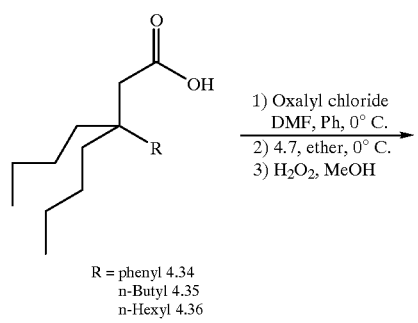

R = phenyl 4.34
n-Butyl 4.35
n-Hexyl 4.36

-continued

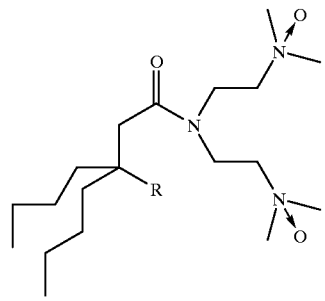

R = phenyl 4.37
n-Butyl 4.38
n-Hexyl 4.39

The dinitrile was refluxed in ethyleneglycol and potassium hydroxide for three days, yielding the monocarboxylic acids 4.34, 4.35, and 4.36. These carboxylic acids were initially converted to the acyl chlorides using thionyl chloride, but later oxalyl chloride was found to provide cleaner and higher yields. Condensation of the acyl chlorides with amine 4.7 and subsequent oxidation with methanolic hydrogen peroxide provided detergents 4.37, 4.38, and 4.39.

BR solubilization can be used as one measure to evaluate the utility of tripod detergents with regard to membrane protein manipulation. Solubilization of BR was successfully accomplished with detergent 4.37 with greater than 90% efficiency after mixing for approximately 20 hrs. Compound 4.39 showed approximately 30% solubilization after 11 days.

A second series of detergents synthesized was designed to vary further the size and flexibility of the hydrophobic domain. A cyclooctyl ring was used to replace the dibutyl chains in 4.37. The inclusion of a cyclic group was expected to increase the rigidity of the detergent. Compounds 4.44 and 4.46 were synthesized starting with condensate of cyclooctanone with malononitrile, 4.41. Reaction of 4.41 with phenylmagnesium bromide and copper (I) iodide, however, did not yield the desired product 4.42 reproducibly. Large amounts of starting material were always recovered; it appears that deprotonation of the alkylidiene was a competing side reaction. Employing the higher order cuprate of Davis (Davis, A. P.; Orchard, M. G. *J. Chem. Soc. Perkins Trans. I* 1993: 919–924), 4.42 can be synthesized in good yields (60–70%). The dinitrile was hydrolyzed and decarboxylated to provide carboxylic acid 4.43.

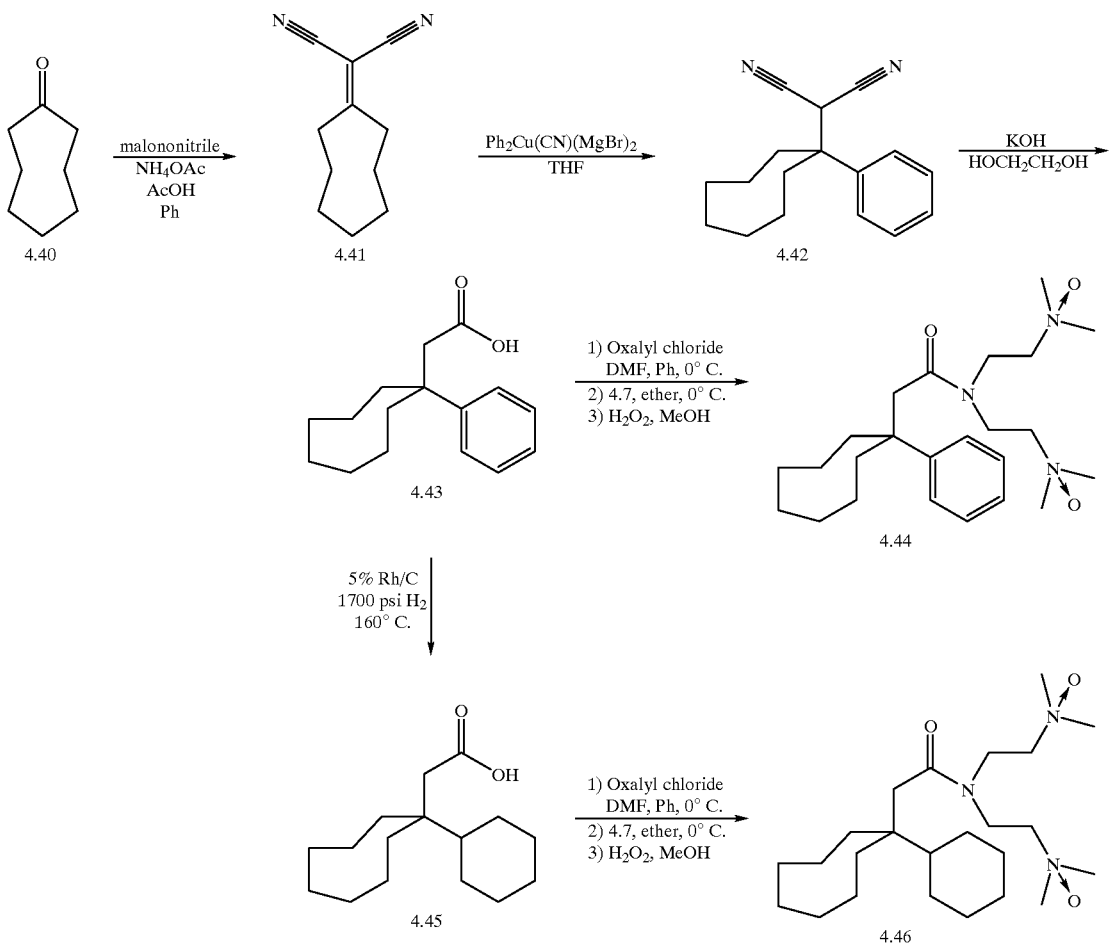

The aryl ring of 4.43 can be hydrogenated to a cyclohexyl ring in the presence of rhodium on carbon to provide the cyclohexyl-cyclooctyl carboxylic acid 4.45. The acids 4.43 and 4.45 were further elaborated to bis-N-oxides 4.44 and 4.46, respectively, as previously described.

Compounds with two phenyl rings attached to the quaternary center were synthesized using 1,1-cyano-2,2-diphenylethylene. It is preferred that 1,1-cyano-2,2-diphenylethylene be prepared by the method of Campaigne et al. (Campaigne, E.; Mais, D.; Yokley, E. M. *Syn. Comm.* 1974, 4:379). Benzonitrile is reacted with phenylmagnesium bromide, and the intermediate imine is rapidly quenched with malononitrile.

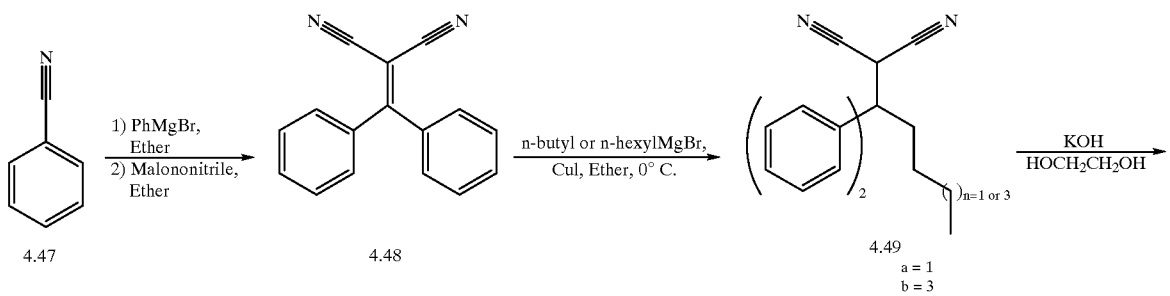

-continued

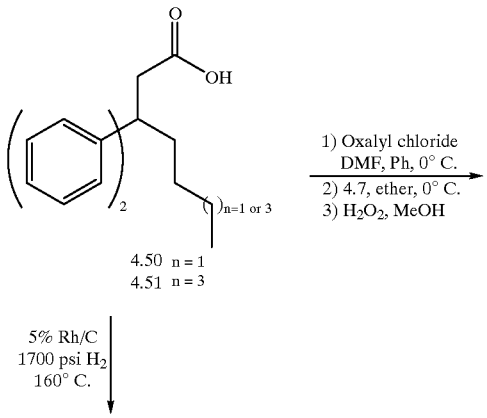

4.50 n = 1
4.51 n = 3

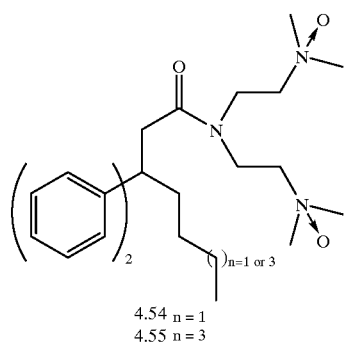

4.54 n = 1
4.55 n = 3

5% Rh/C
1700 psi H$_2$
160° C.

1) Oxalyl chloride
DMF, Ph, 0° C.
2) 4.7, ether, 0° C.
3) H$_2$O$_2$, MeOH 4.52 n = 1
4.53 n = 3

1) Oxalyl chloride
DMF, Ph, 0° C.
2) 4.7, ether, 0° C.
3) H$_2$O$_2$, MeOH

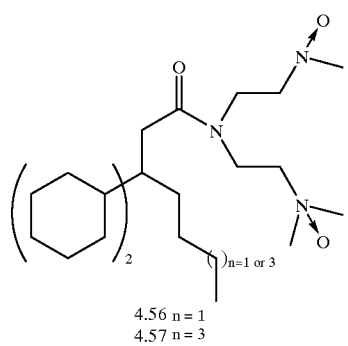

4.56 n = 1
4.57 n = 3

This alkylidiene was then reacted with n-butyl-, or n-hexylmagnesium bromide and copper (I) bromide. The dinitrile products were hydrolyzed and decarboxylated to provide carboxylic acids 4.50 and 4.51, which were hydrogenated with rhodium on carbon to yield the dicyclohexyl acids 4.52 and 4.53. All four acids were converted to their acyl chlorides, reacted with 4.7, and oxidized with methanolic hydrogen peroxide.

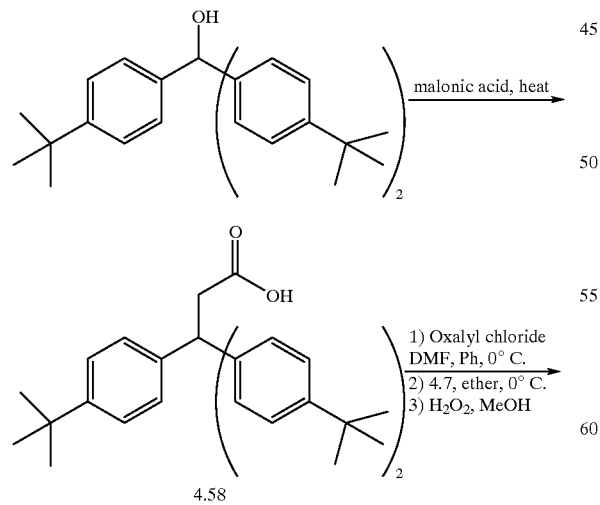

4.58

-continued

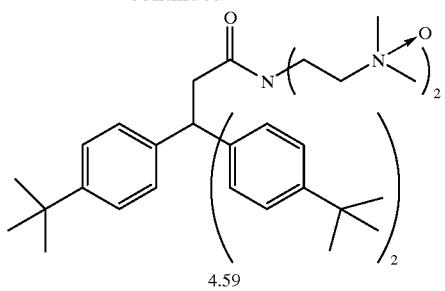

4.59

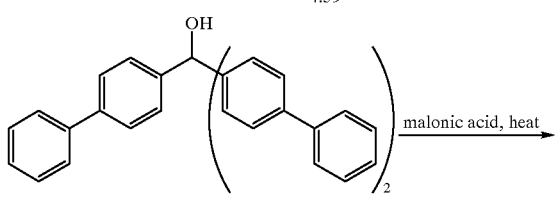

4.60 malonic acid, heat

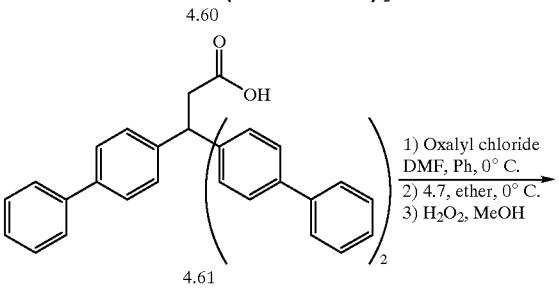

4.61

1) Oxalyl chloride
DMF, Ph, 0° C.
2) 4.7, ether, 0° C.
3) H$_2$O$_2$, MeOH

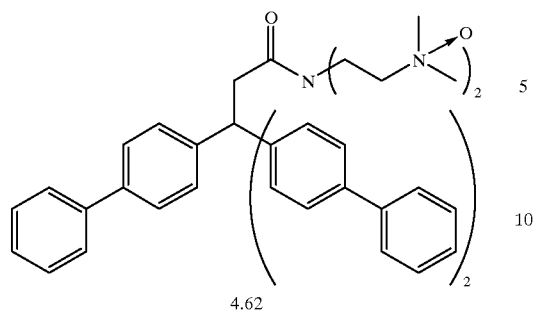

4.62

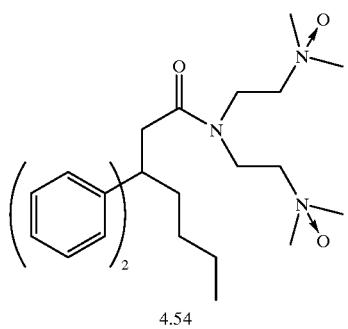

4.54

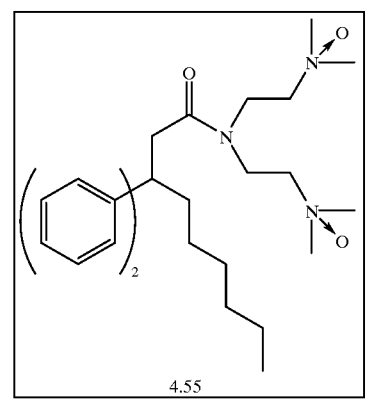

4.55

Tris-biphenylmethylacetic acid and tri-t-butylphenylmethylacetic acid derivatives complete this second series of detergents. These syntheses began by condensing the corresponding triarylmethanols with neat malonic acid, and proceeded as previously described to provide bis-N-oxides 4.59 and 4.62. Both 4.59 and 4.62 were insoluble in water. However, when small amounts of ethanol or ethyl acetate were added to aqueous suspensions, the solubility of these amphiphiles greatly increased.

The second series of tripod detergents synthesized by the modular approach clearly demonstrates the myriad hydrophobic moeities accessible using this methodology. Two detergents from this series, 4.55 and 4.56, readily solubilize BR.

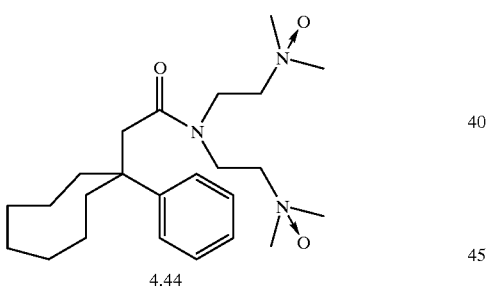

4.44

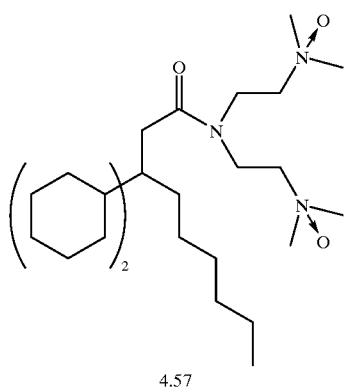

4.57

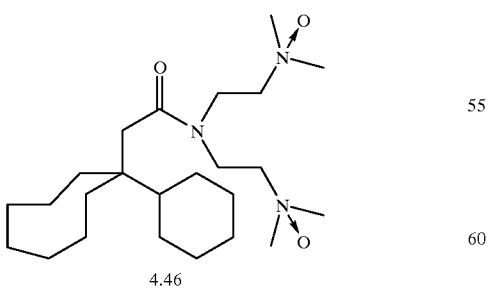

4.46

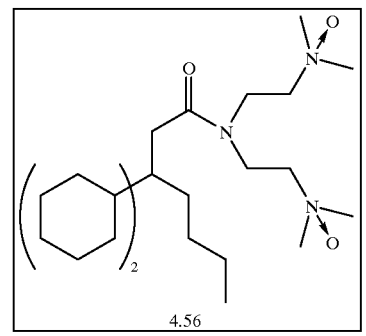

4.56

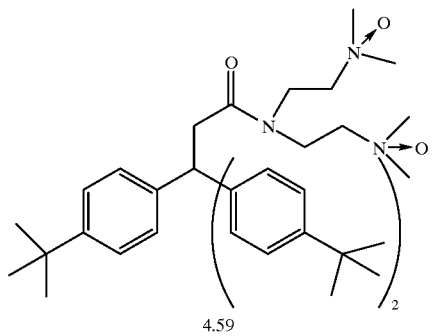

4.59

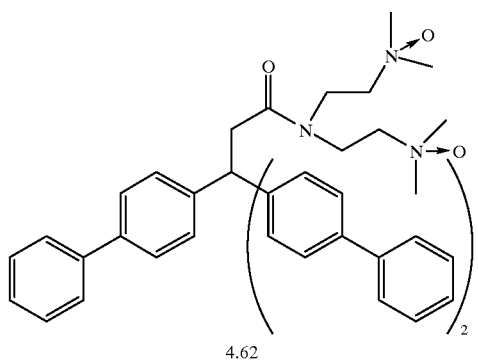

4.62

Using the above protocol, different amines can be condensed to produce other detergents having mono- and bis-N-oxides in the hydrophilic domain.

In the course of a detailed investigation of 4.37, a second batch of material was prepared. This second batch provided much lower solubilization yields (<50%) than the original batch. The composition of each batch was analyzed by HPLC. The two batches that solubilized BR to varying degrees showed varying amounts of an impurity. The first batch, which solubilized BR to >90%, had approximately twice as much impurity compared to the second batch that solubilized the BR with only 50% efficiency. Scrutiny of the $^1$H-NMR spectrum of the first batch of 4.37 revealed a small set of resonances in the vinyl region. Alumina chromatography of the mixture of 4.37 and the impurity provided an impure sample that was enriched in the material with the vinyl resonances. A mass spectrum revealed a M(+H) peak at 375.30, indicating that the impurity was 4.63, which presumably results from a Cope elimination of one of the N-oxide headgroups:

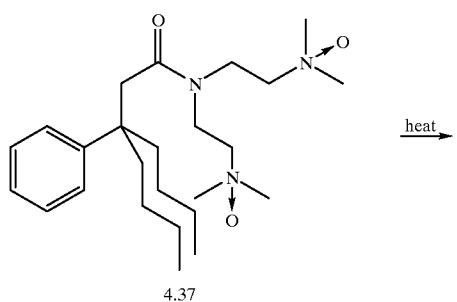

4.37

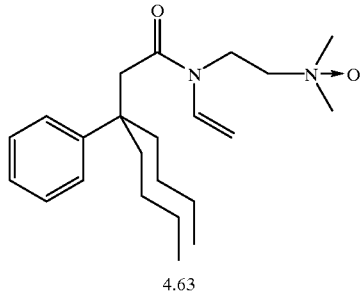

4.63

A saturated analog of 4.63, 4.65, was synthesized by condensing commercially available 4.64 with the acyl chloride of 4.34:

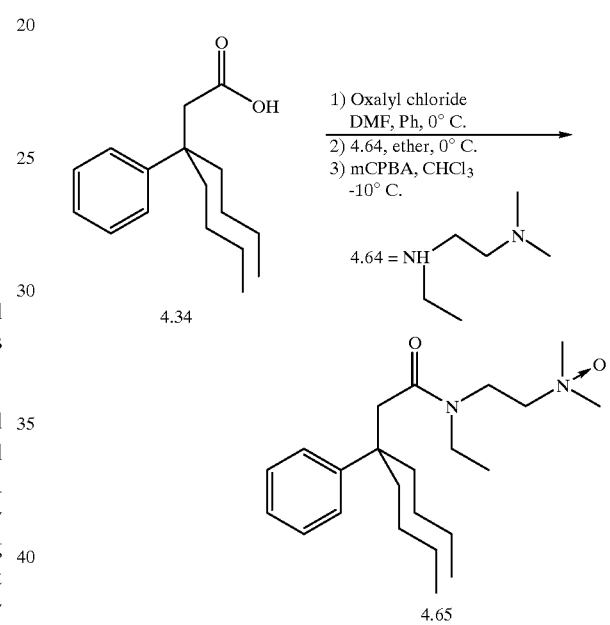

The resulting tertiary amide was oxidized with mCPBA instead of methanolic hydrogen peroxide to provide the mono-N-oxide 4.65. mCPBA reacted faster, provided an easier work-up and yielded cleaner product.

Compound 4.65 was shown to be >99% pure by HPLC and solubilized BR to greater than 90%. These results lead to a series of N-oxides based on the acid 4.34 to investigate the influence the headgroup has on BR solubilization. Compounds 4.67 and 4.68 are isomers of 4.65. The secondary amide 4.68 cannot undergo a Cope elimination because there are no protons on the carbon adjacent to the amide. The one-carbon homologue of 4.68, 4.70, was also synthesized. The secondary amide 4.66 was synthesized along with 4.71 to investigate the difference in solubilizing ability between the mono-N-oxide versus a bis-N-oxide. Detergent 4.69 is the simplest N-oxide accessible, and 4.72 was prepared to test the effect of removing the ethyl chain from 4.65. Compound 4.66 readily solubilize BR.

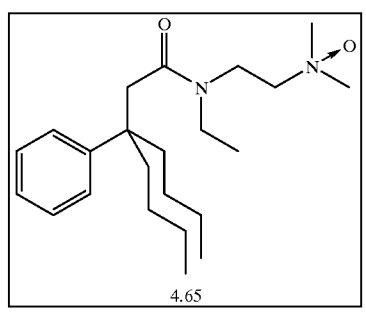
4.65
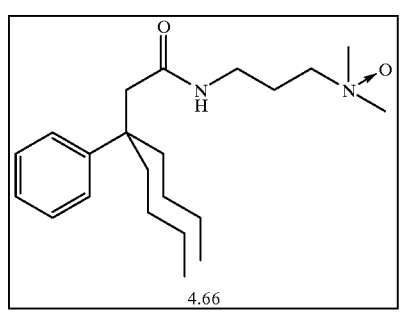
4.66
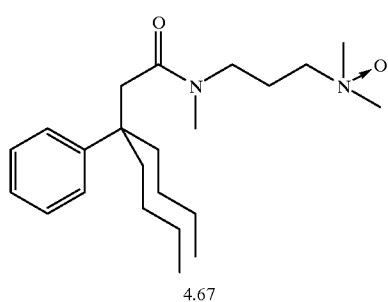
4.67
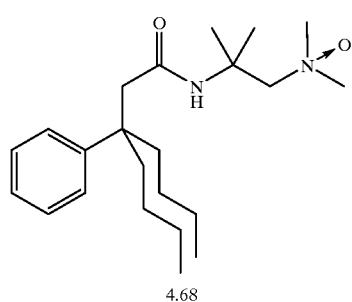
4.68
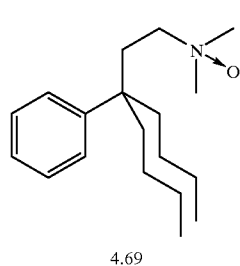
4.69
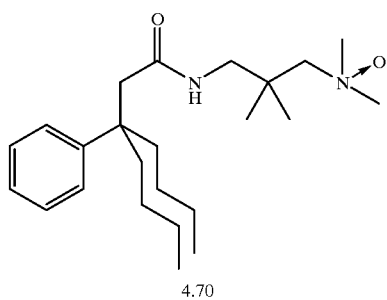
4.70
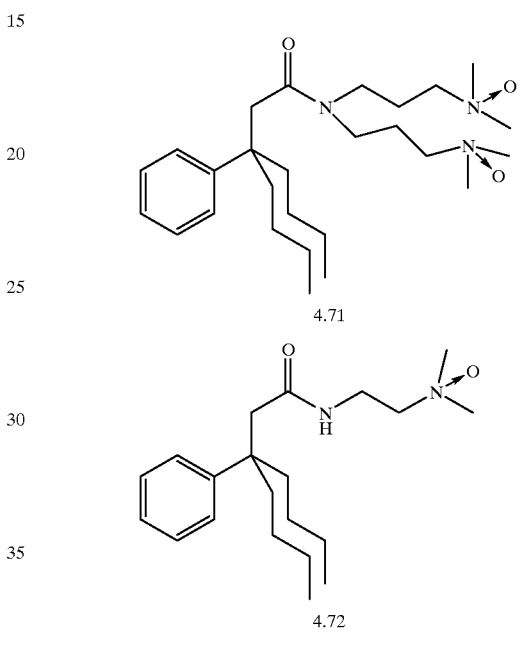
4.71
4.72
The headgroup was then altered to yield detergents 4.73, 4.74, 4.75, and 4.77:
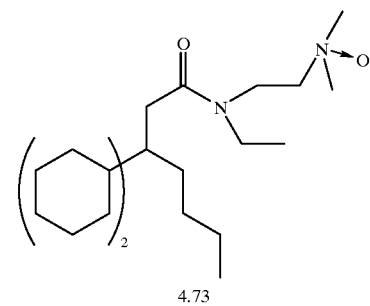
4.73
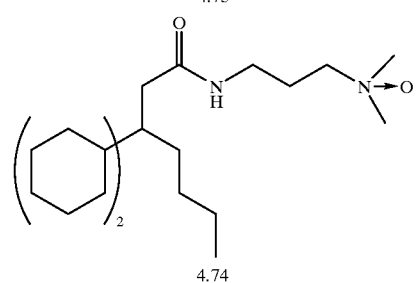
4.74

-continued

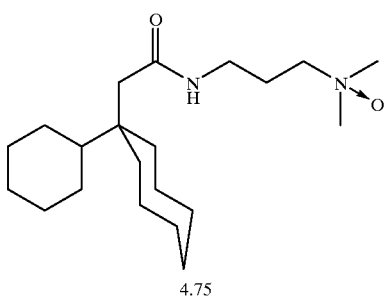

4.75

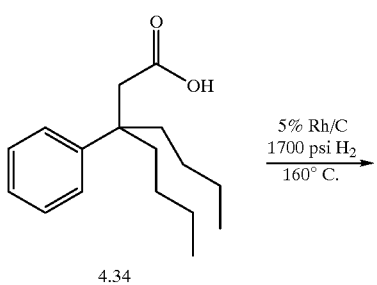

4.34

5% Rh/C
1700 psi H$_2$
160° C.

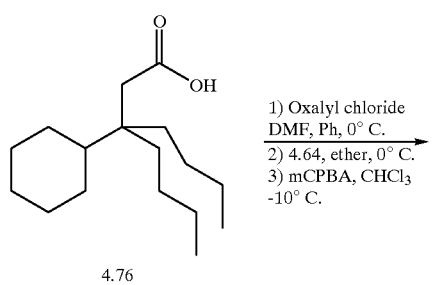

4.76

1) Oxalyl chloride
DMF, Ph, 0° C.
2) 4.64, ether, 0° C.
3) mCPBA, CHCl$_3$
-10° C.

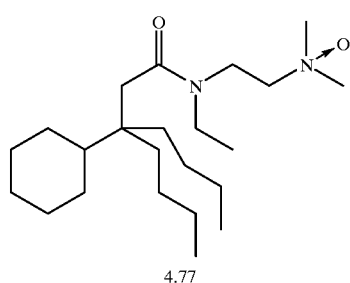

4.77

Removal of BR from the purple membrane (the native two-dimensional lattice) is the difficult step in solubilization of BR, and only three detergents, Triton X-100, nonyl glucoside (NG) and OG, have been reported to successfully remove BR from its native environment. Some detergents can maintain BR in a stable solubility after being exchanged with Triton X-100, NG, or OG. The exchange can occur via dilution, ion-exchange, and size exclusion chromatography, as is known in the art. Often the detergents that can solubilize a protein from a lipid environment are more denaturing than detergents that can maintain protein solubility through exchange. This implies that tripods that cannot solubilize BR from the purple membrane may be able, upon exchange, to maintain the solubility of BR. Exchanging Triton X-100 or some other detergent, for the tripod detergents of the present invention that cannot solubilize BR from the purple membrane provides a route to increase the number of tripods that can be screened for proclivity to crystallize membrane proteins.

The CMCs of detergents 4.65–4.72 were determined by monitoring the uptake of a fluorescent dye (1,6-diphenylhexatriene) with increasing detergent concentration (Table 1, CMC's determined by dye uptake versus concentration monitored by fluorescence spectroscopy). The CMCs of N-oxide isomers 4.65, 4.67, and 4.68 are very similar: 3 mM, 3 mM, and 1.2 mM, respectively. Table 1 also reveals that the hydrochloride salts tend to have CMCs twice as large as the CMCs measured for the corresponding N-oxides. The only instance where this trend breaks down is for detergents 4.65 and 4.66, two detergents that can solubilize BR. The CMCs for the N-oxides 4.65 and 4.66 are twice the CMCs of the corresponding hydrochloride salts (4.78 and 4.79). The hydrochloride salts were formed from the amine precursors to the N-oxides. Most cationic detergents have CMCs that are much higher than non-ionic or zwitterionic analogs. For example, dodecylammonium bromide has a CMC of 15 mM which is >7 times larger than the CMC of the N-oxide analog (LDAO, CMC=2 mM).

Considering the difference of CMC between 4.68 and homologue 4.70 one would expect the addition of one carbon to decrease the CMC by a factor of three. Surprisingly, 4.70 has a CMC that is six times larger than that of 4.68. The headgroup of 4.70 has both greater flexibility and is one methylene longer than 4.68. This increase in length and flexibility may allow the secondary amide of 4.70 to be more solvent-exposed than the more sterically encumbered secondary amide of 4.68. The greater solvent exposure would increase the solubility while at the same time increasing the CMC of 4.70 relative to 4.68.

TABLE 1
Critical Micelle Concentration of N-Oxides and Hydrochloride Salts
| Detergent | CMC | Detergent | CMC |
|---|---|---|---|
| 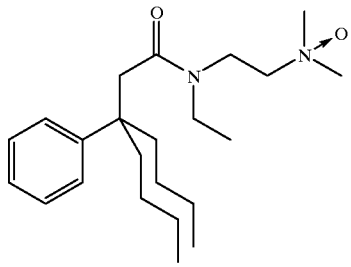<br>4.65 | 3 mM | 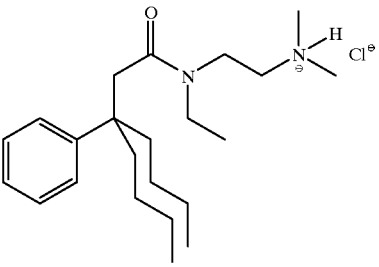<br>4.78 | 1.3 mM |
| 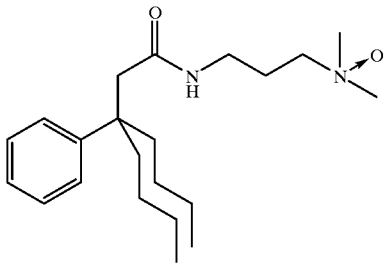<br>4.66 | 4.5 mM | 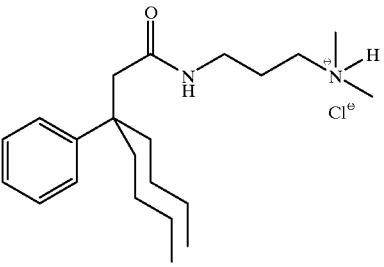<br>4.79 | 2.8 mM |
| 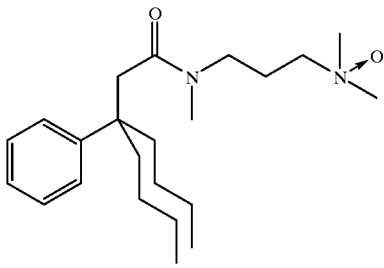<br>4.67 | 3 mM | 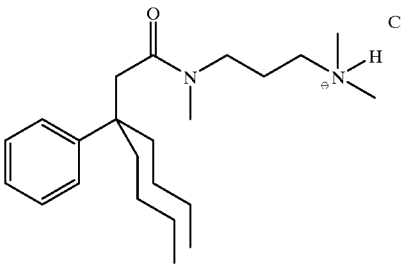<br>4.80 | 5 mM |
| 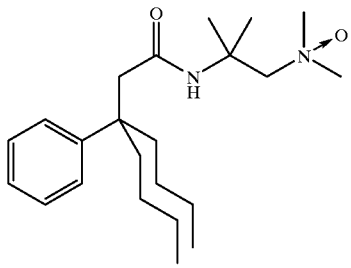<br>4.68 | 1.2 mM | 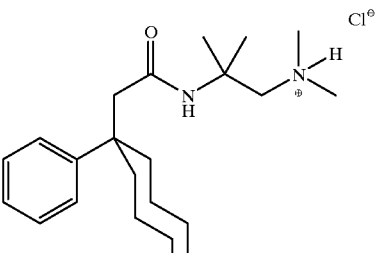<br>4.81 | Does not take up dye up to solubility limit of ~12.5 mM |

TABLE 1-continued

Critical Micelle Concentration of N-Oxides and Hydrochloride Salts

| Detergent | CMC | Detergent | CMC |
|---|---|---|---|
| 4.69 | 2.5 mM | 4.82 | 5 mM |
| 4.70 | 7.5 mM | 4.83 | 14.7 mM |
| 4.71 | 10 mM | 4.84 | 24 mM |

The aggregate structure of a detergent, and hence its ability to solubilize proteins, can be strongly influenced by salt concentration, pH, temperature, and organic additives; therefore, attempting to solubilize BR using the detergents of the present invention under varied salt, pH and temperatures may provide different results.

Using the acids described above, a series of bis-hydrochloride salt tripod detergents were synthesized. See Table 2. The surface area of the tripod tails was calculated using the MM3 force field with 1.4 Å probe. The 1.4 Å probe represents a sphere with a diameter equal to the van der Waals radius of an oxygen atom in a water molecule. The 1.4 Å probe, when computationally rolled across the surface of a molecule, defines the water-exposed surface area. The surface areas were plotted against the measured CMC of each detergent in Table 2. If the data are divided into detergents with and without aromatic groups, a linear correlation between surface area and CMC is observed ($r^2$=0.82 with aromatic "legs"; $r^2$=0.80 without aromatic "legs").

The relationship between CMC and surface area indicates that there is a distinct difference in tripods that contain aromatic groups and those that do not. However, within the two divisions, aromatic and non-aromatic, the nature of the tripod leg seems to matter very little and the CMC is governed by surface area. The greater the surface area the smaller the CMC, which is consistent for a series of straight chain detergents with varying lengths. For example the CMCs for LDAO and DDAO are 1.1 mM and 10.4 mM respectively. An aromatic ring is more polar than a saturated hydrocarbon and the difference in polarity may account for why the surface areas only correlate well when the tripod detergents are divided into an aromatic group and non-aromatic group.

Isomers of 4.65 were synthesized to evaluate the influence of topology on aggregation in aqueous solution, and on solubilization of BR. Isomer 4.100 was synthesized by an efficient three step route beginning with a Pd (II) coupling of decylmagnesium bromide to 1,4-dibromobenzene by the method of Bumagin et al. (Bumagin, N. A.; Luzikova, E. V.; Beletskaya, I. P. Russian *J. Org. Chem.* 1996, 31:1480–1486). The alkyarylbromide was then lithiated with t-butyl lithium and quenched with dry carbon dioxide. The resulting acid was coupled to amine 4.64 via the acylchloride. The amine was then oxidized with mCPBA.

TABLE 2

| Detergent | MM3 S.A.[a] | CMC[b] | Detergent | MM3 S.A. | CMC |
|---|---|---|---|---|---|
| 4.84 | 473 | 24 mM | 4.96 | 472 | 4.6 mM |
| 4.85 | 412 | 80 mM | 4.95 | 419 | 24 mM |
| 4.86 | 500 | 21 mM | 4.94 | 510 | 3 mM |
| | 564 | 4 mM | | 482 | 6 mM |

TABLE 2-continued

| Detergent | MM3 S.A.[a] | CMC[b] | Detergent | MM3 S.A. | CMC |
|---|---|---|---|---|---|
| 4.87 | 496 | 30 mM | 4.93 | 546 | 1 mM |
| 4.88 | 595 | 3 mM | 4.92 | 793 | insol. |
| 4.89 | | | 4.91 | | |
| 4.90 | 848 | insol. | | | |

[a] MM3 calculations
[b] As Determined by Dye Uptake Versus Concentration Monitored by Fluorescence Spectroscopy The synthesis of the second isomer of 4.65 was performed by a reaction of 5-nonanone with methyl lithium to provide 4.101. The resulting alcohol was coupled to toluene with titanium tetrachloride. The aryl methyl group was oxidized with molecular oxygen under catalysis by hydroxyphthalimide and cobalt (II) acetoacetonate. The acid was then reacted with oxalyl chloride, condensed with amine 4.64 and finally oxidized with mCPBA to provide 4.104.

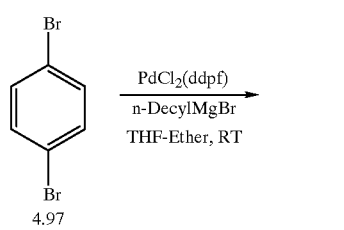

dppf = 1,1'-bis(diphenylphosphino)ferrocene

-continued

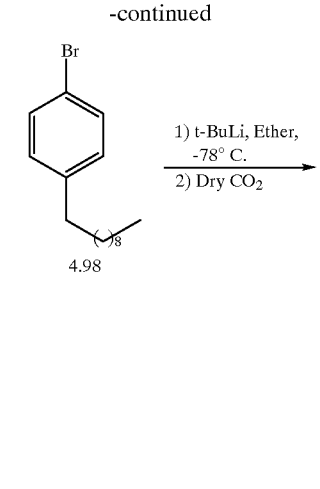

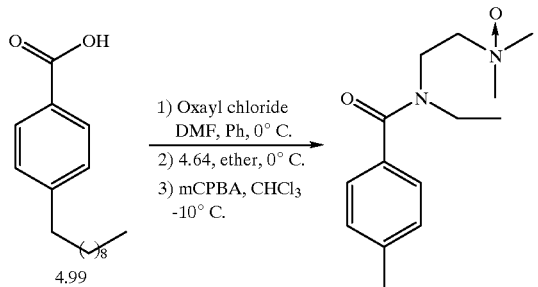
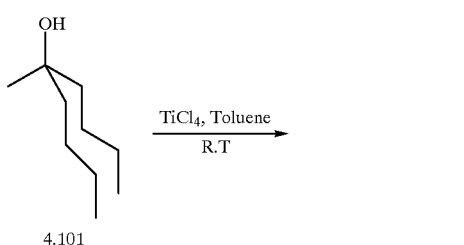
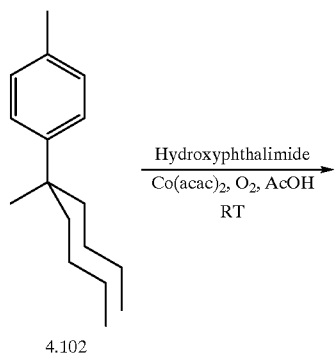
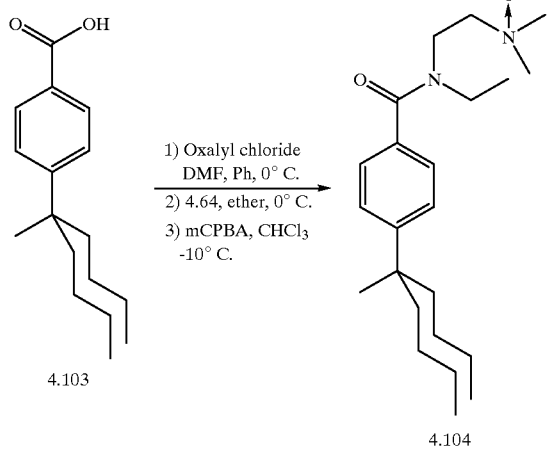
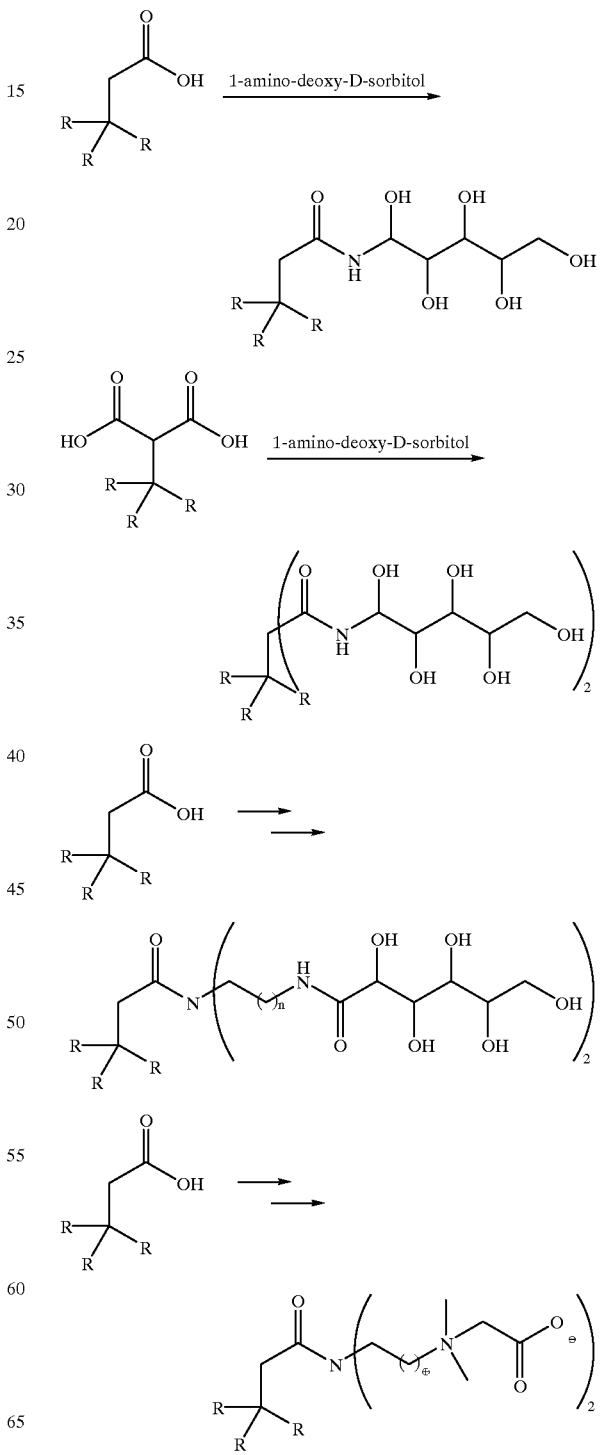

The CMCs of 4.100 and 4.104 were determined by the uptake of the fluorescent dye 1,6-diphenylhexatriene. The CMCs are 0.125 mM and 0.700 mM respectively. These values are substantially lower than the CMC of 4.65, which was determined to be 3 mM. The CMCs of 4.100 and 4.104 are much lower than that of LDAO (2.1 mM), indicating the hydrophobic surfaces of 4.100 and 4.104 are larger than that displayed by LDAO or by 4.65. Based on these data, we conclude that the topology of N-oxide isomers 4.65, 4.100 and 4.104 profoundly impacts the concentration at which these detergents self-associate.

The headgroup of the amphiphiles of the present invention can also be non-ionic groups such as polyethylene (glycol) (PEG), glucosyl, or maltosyl. The synthesis of these tripod amphiphiles is straightforward via established procedures.

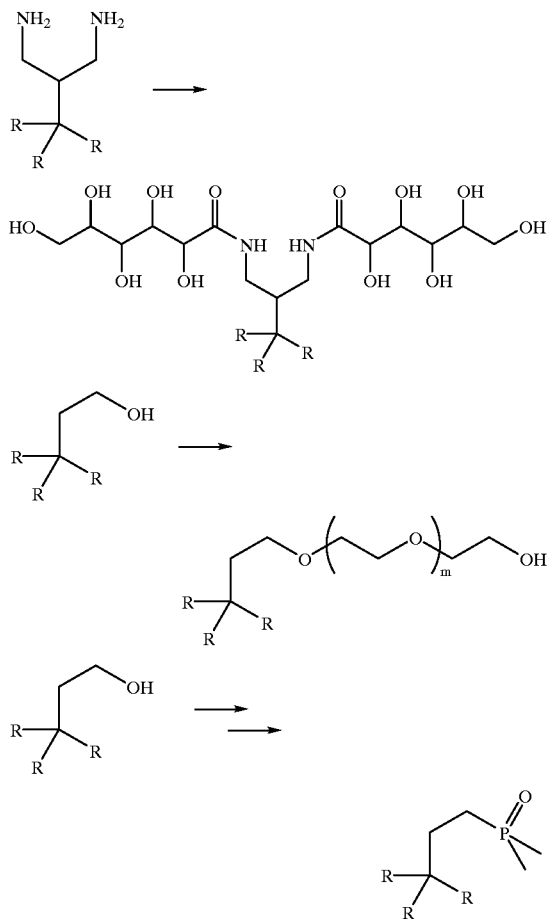
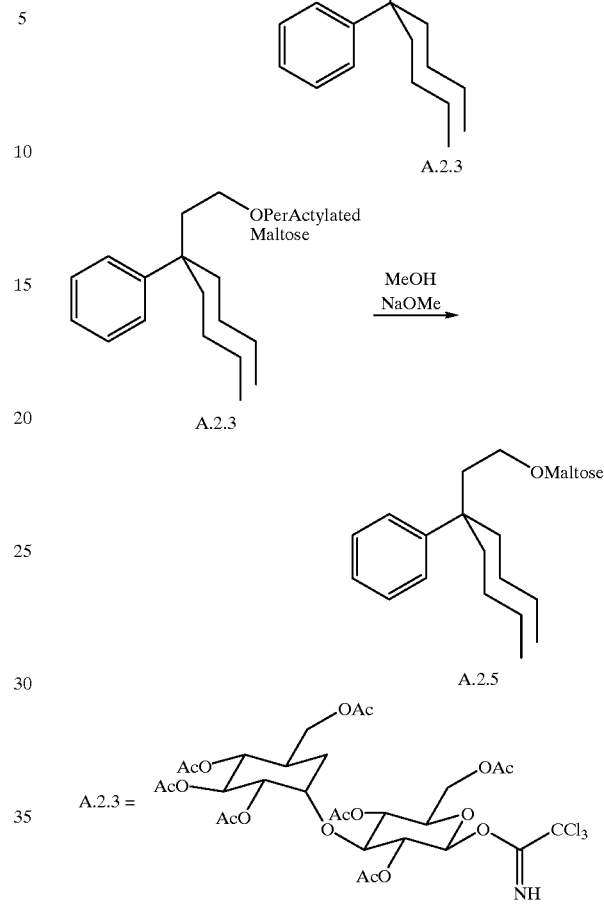

For example, the maltoside A.2.5 was synthesized from the corresponding acid 4.33. The acid 4.33 was reduced with LAH in refluxing THF. The alcohol A.2.1 was then reacted with the trichloracetimidate of peractylated maltose. The resulting alkyl maltoside was deprotected with methanolic sodium methoxide, resulting in the desired product A.2.5.

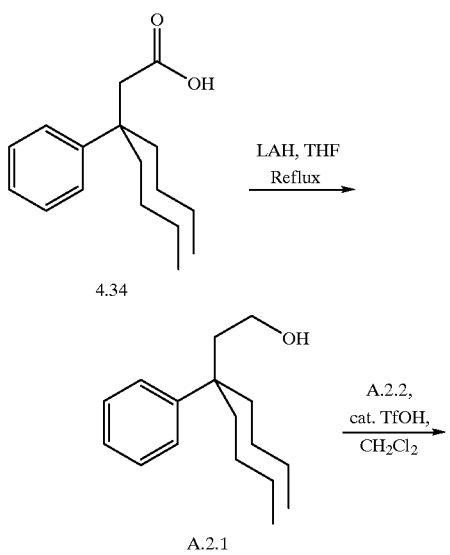

The maltoside A.2.5 is sparingly soluble in water. A.2.5 solubilize approximately 50% of BR from the purple membrane.

A very important aspect of the tripod family of the present invention is their variable rigidity. This family of related detergents provides membrane protein crystallographers with a set of tools that can be used to solubilize and crystallize a wide variety of membrane proteins.

EXAMPLES

The following Examples are included solely as an aid to provide a complete understanding of the invention. The Examples do not limit the scope of the invention described and claimed herein in any fashion.

General

Reagents were purchased from Aldrich Chemical Company, (Milwaukee, Wis., U.S.A.) unless otherwise noted. Ether was distilled from benzophenone-sodium ketyl under nitrogen.

NMR spectra were acquired on Bruker AM-250 or AM-300 spectrometers in deuterated chloroform with tetramethylsilane (TMS) as the internal standard. For all other organic solvents, the residual solvent peak served as the standard. For aqueous solutions, an external reference of sodium 3-(trimethylsilyl)-$d_4$-propionate (TSP) was used.

The solvent and field strengths employed are provided with each spectral listing. For proton NMR spectra, signals are reported as: δ xx (multiplicity, #H, coupling constants, assigned H). Multiplicities are abbreviated as: s=singlet, d=doublet, t=triplet, dd=doublet of doublets, dt=doublet of triplets, q=quartet, ddd=doublet of doublet of doublets, td=triplet of doublets. tt=triplet of triplets, m=multiplet, br=broad, app=apparent. AB quartets, AA'BB', and ABX patterns are listed as such. Carbon resonances are assigned substitution based on DEPT-135 experiments, as reported in parentheses after each chemical shift entry.

Infrared (IR) spectra were obtained on either a Mattson Polaris instrument or a Nicolet 740 infrared spectrometer. Absorbance intensities are reported as st=strong, m=medium, w=weak, br=broad. High-resolution mass spectra were recorded on a Kratos MS-25. Fast Atom Bombardment mass spectra (FABMS) were obtained on a VG Analytical ZAB-2F spectrometer. Melting points were determined on a Thomas Hoover apparatus and are uncorrected. UV spectra were obtained on a Hewlett-Packard 8452 Diode Array Spectrophotometer.

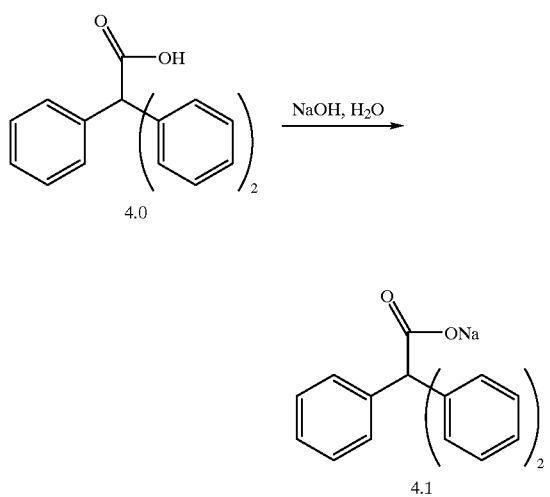

Triphenylacetic acid sodium salt (4.1). Triphenylacetic acid was dissolved in an aqueous NaOH solution containing 2–5% molar excess of semi-conductor grade NaOH. Once the acid had completely dissolved, the solution was filtered through a 0.22 mm syringe filter, lyophilized, and further dried in a drying pistol charged with $P_2O_5$ under vacuum for 2 days. A solution of the lyophilized solid was always slightly basic (pH 9).

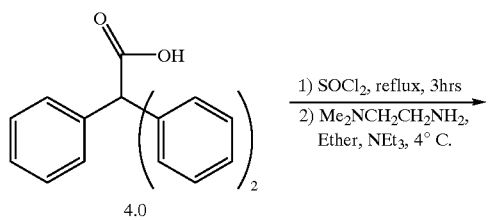

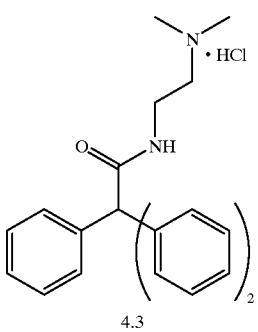

Preparation of 4.3. Triphenylacetic acid (1.0 g, 3.5 mmol) was refluxed in thionyl chloride (9 ml, 123 mmol) for 3 hours at which time the solution was cooled to room temperature and the excess thionyl chloride was removed by vacuum. The resulting oil was dissolved in dry ether and cooled to 4° C. in an ice bath. N,N-dimethylethylenediamine (7.62 mL, 7 mmol) was added dropwise resulting in a white precipitate. The reaction was allowed to stir overnight and was then washed with 1 N NaOH (50 mL) three times. The organic layers were dried with $MgSO_4$, gravity filtered, and concentrated on a rotary evaporator. The resulting oil was dissolved in 10 mL of freshly distilled ether and the amine was precipitated as the HCl salt with 4N HCl in dioxane (8.75 mL, 3.5 mmol). The precipitate which was crystalline was filtered, washed with dry ether, and placed on a vacuum line to afford 1.38 g (100%) of a white solid. The white solid was crystallized from water providing X-ray quality crystals. IR (KBr): 3373 (N—H), 2817–2767 (br), 1664 (C=O), 1491. $^1$H NMR (CDCl$_3$, 300 MHz): δ 2.08 (s, 6H); 2.32 (t, J=6 Hz, 2H); 3.38 (dt, J=6.5 Hz, 2H); 6.36 (t, J=5 Hz, $^1$H); 7.2–7.3 (m, 15H); $^{13}$C NMR (CDCl$_3$, 75.4 MHz): δ 173.3 (C), 143 (C), 130.5 (CH), 127.8 (CH), 126.8 (CH), 67.7 (C), 57.3 (CH$_2$), 44.9 (CH$_3$), 37.6 (CH$_2$). EI-MS m/z (M$^+$H$^+$) calcd for $C_{24}H_{27}N_2O$ 359.2045, obsd 359.2101.

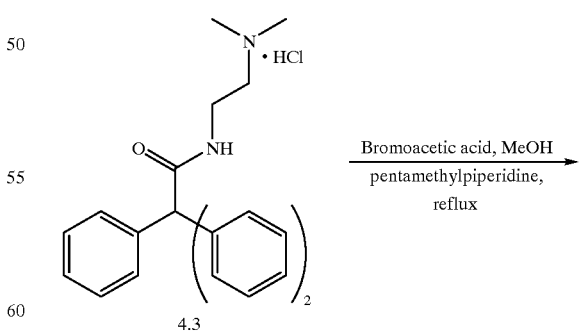

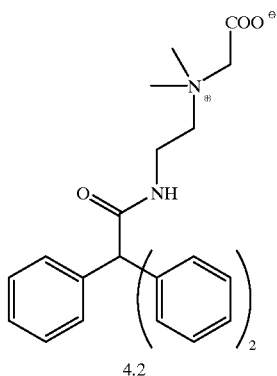

4.2

Preparation of 4.2. The free base of amido amine 4.3 (1 g, 2.79 mmol) was dissolved in 25 mL of MeOH. Bromoacetic acid (388 mg, 2.78 mmol) and then pentamethylpiperidine (5.05 mL, 2.79 mmol) were added and the solution was refluxed for two days. Once the solution cooled to room temperature the MeOH was rotary evaporated. The resulting solid was dissolved in methylene chloride with 10% MeOH and two scupulas of silica gel were added. The solvent was removed leaving the product preabsorbed to silica gel. The gel was loaded onto a silica gel column pre-equilibrated with methylene chloride with 10% MeOH. The fractions containing product were collected and concentrated; the off-white solid was recrystallized from water which resulted in X-ray quality crystals. IR (KBr): 3353 (N—H), 2774 (br), 1648 (C=O), 1491. $^1$H NMR (CDCl$_3$/DMSO-d6, 300 MHz): δ 3.01 (s, 6H); 3.656 (br,s 6H); 7.2–7.3 (m, 15H); 7.62 (t, 1H); $^{13}$C NMR (CDCl$_3$/DMSO-d6, 75.4 MHz): δ 172.6 (C), 164.1 (C), 142.6 (C),129.6 (CH), 127.0 (CH), 125.9 (CH), 66.7 (CH$_2$), 64.1 (CH$_2$), 61.4 (C), 49.9 (CH$_3$). EI-MS m/z (M$^+$H$^+$) calcd for C$_{26}$H$_{28}$N$_2$O$_3$ 316.2100, obsd 316.2080.

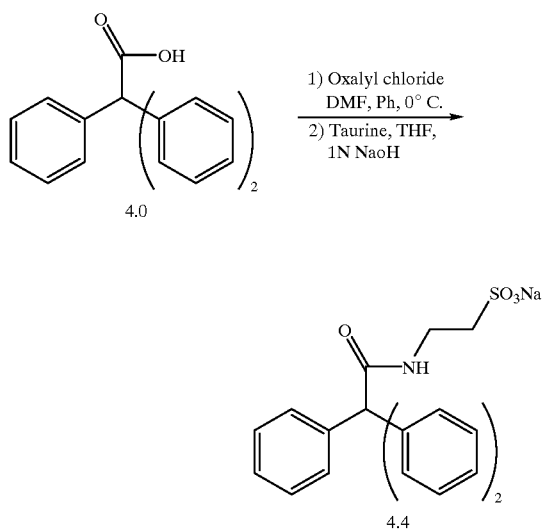

Preparation of 4.4. Triphenylacetic acid (2 g, 6.94 mmol) was dissolved in 5 mL of benzene in a round bottom flask. One drop of DMF was added as a catalyst and the solution was cooled with an ice bath. Once the solution had cooled oxalyl chloride (3 mL, 34.7 mmol) was added dropwise resulting in a vigorously bubbling solution. The reaction was allowed to stir 3 hours and the volatiles were removed under vacuum. The resulting oil was dissolved in 25 mL of THF and the round bottom flask was fitted with an addition funnel. The solution was cooled and a solution of taurine (1.3 g, 11.6 mmol) in 13 mL of 1 N NaOH was mixed with 12 mL of THF and the solution was placed into the addition funnel and added dropwise. The reaction was stirred overnight and the THF was removed by rotary evaporation. The resulting solid was collected and washed with water. The material was then recrystallized from water providing 2.5 g (90%) of light yellow plates. IR (KBr): 3439 (N—H), 2763 (br), 1655 (C=O), 1218. $^1$H NMR (CDCl$_3$/DMSO-d6, 300 MHz): δ 2.58 (t, J=22, 1H); 2.75 (t, J=22 Hz, 6H); 2.92 (dt, J=18, 22, $^1$H); 3.48 (s, 6H); 3.562 (dt, J=22,18 Hz, 1H); 7.17–7.30 (m, 16H); 7.42 (t, J=18 Hz, 0.5H)); $^{13}$C NMR (CDCl$_3$/DMSO-d6, 75.4 MHz): δ 172.0 (C), 143.5 (C), 130.2 (CH), 127.5 (CH), 126.4 (CH), 67.3 (C), 52 (CH$_2$), 49.8 (CH$_2$), 37.67 (CH$_2$), 36.3 (CH$_2$).

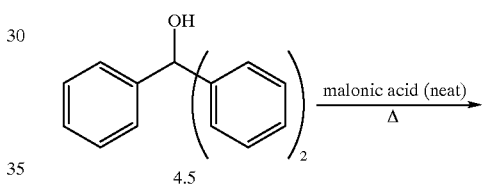

4.5

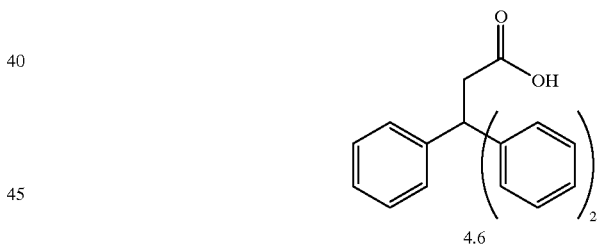

4.6

Preparation of 3,3,3-Triphenylpropionic Acid, 4.6. Triphenylmethanol (20 g, 77 mmol) was combined with malonic acid (13 g, 125 mmol) in a mortar and ground together well with a pestle. The finely ground mixture was placed into a pear-shaped 100 mL flask and heated to 140–170° C. The solid slowly melted to form a bright red mixture which bubbled vigorously. The reaction was heated until the solution stopped bubbling and was allowed to cool to room temperature. The resulting white solid was recrystallized from ethanol providing 9.99 g (43%, 1st crop) X-ray quality crystals that were submitted for analysis. IR (KBr): 2829 (br), 1710 (C=O), 1232. $^1$H NMR (CDCl$_3$): δ 3.69 (s, 2H); 7.1–7.3 (m, 15H); $^{13}$C NMR (CDCl$_3$, 75.4): δ 176.4 (C), 146.2 (C), 129.4 (CH), 127.8 (CH), 126.2 (CH), 55.3 (C), 45.8 (CH,); EI-MS m/z (M$^+$H$^+$) calcd for C$_{21}$H$_{18}$O$_2$: 302.1306, obsd 302.1272.

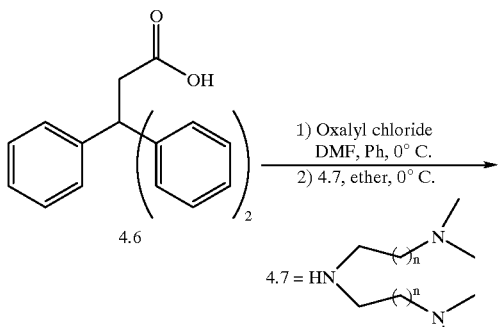

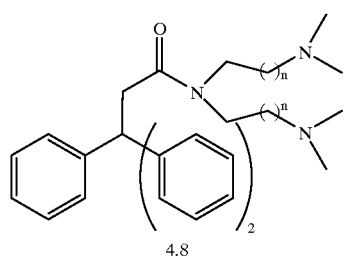

Preparation of 4.8. The acid 4.6 (4.73 g, 15.6 mmol) was dissolved in 5 mL of benzene in a round bottom flask. One drop of DMF was added as a catalyst and the solution was cooled with an ice bath. Once the solution had cooled, the oxalyl chloride (3 mL, 34.7 mmol) was added dropwise resulting in a vigorously bubbling solution. The reaction was allowed to stir 3 hours and the volatiles were removed under vacuum. The residue was dissolved in dry ether (100 mL), cooled to 0° C., and 4.7 (n=1) (6.02 mL, 33.2 mmol) in ether (50 mL) was added dropwise resulting in a white precipitate. (Triamine 4.7 was made by the procedure of Luitjes, H.; Schakel, M.; Klumpp, G. W. Syn. Comm. 1994, 24, 2257–2261.) The solution was allowed to stir overnight. The next day 1 N NaOH (25 mL) was added and the precipitate dissolved. The layers were separated and the ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 4.5 g (69%) of a light yellow oil. The oil was dissolved in 30 mL of ether and the amine was precipitated by adding 4 N HCl in dioxane (5.6 mL) diluted in 30 mL of ether. The light yellow solid was washed with dry ether and recrystallized with ethanol. The recrystallization resulted in X-ray quality crystals which were submitted for analysis. IR (KBr): 3436 (N—H), 2939–2701 (br), 1658 (C=O), 703. $^1$H NMR (DMSO-d6): δ 2.73 (dd, 6H); 2.95 (br,m 2H); 3.14 (br,m, 2H); 3.51 (br, m, 2H); 3.72 (br, m, 2H); 3.91 (s, 2H); 7.1–7.3 (m, 15H); 7.62 (t, $^1$H); $^{13}$C NMR (DMSO-d6, 75.4): δ 170.6 (C), 147.2(C), 129.4 (CH), 127.6 (CH), 125.8 (CH), 66.7 ($CH_2$), 56.2 ($CH_2$), 55.9 (C), 53.1 ($CH_2$), 42.2 ($CH_3$), 41.2 ($CH_2$); MALDI TOF ($M^+$Na) calcd for $C_{29}H_{37}N_3$ONa 466, obsd 466 ($M^+$Cs) 575, obsd 575.

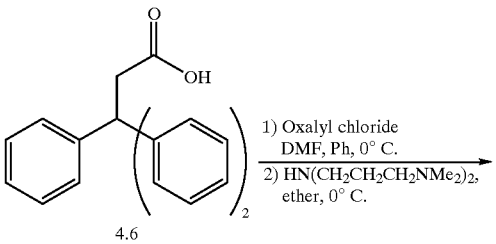

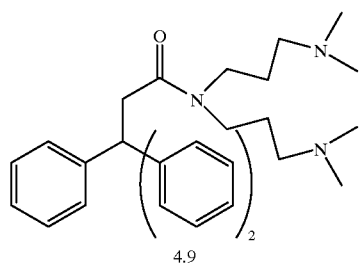

Preparation of 4.9. The acid 4.6 (1 g, 3.3 mmol) was dissolved in 30 mL of benzene in a round bottom flask. One drop of DMF was added as a catalyst and the solution was cooled with an ice bath. Once the solution had cooled the oxalyl chloride (1.44 mL, 16.5 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (4.7, n=2) (1.47 mL, 6.6 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated, yielding 550 mg (37.5%) of a light yellow oil. The oil was dissolved in 30 mL of ether and the amine was precipitated by adding 4 N HCl in dioxane (5.6 mL) diluted in 30 mL of ether. The light yellow solid was washed with dry ether and recrystallized with ethanol. IR (KBr): 3413 (N—H), 3056–2769 (br), 2242 (N—H), 1641 (C=O), 1459. $^1$H NMR (CDCl$_3$): δ 1.84 (br, dt, J=4,7 2H); 2.05 (br,m, 2H); 2.70 (d, J=5, 6H); 2.76 (br, m, 2H); 2.83 (d, J=5 Hz, 6H), 3.04 (br, m, 2H), 3.19 (t, J=7 Hz, 2H), 3.37 (t, J=7, 2H), 3.71 (s, 2H), 7.17–7.30 (m, 15H); 11.65 (br, m, 1H) 12.00 (br, m, 1H); $^{13}$C NMR (CDCl$_3$, 75.4): δ 170.5 (C), 146.3 (C),129.0 (CH), 127.6 (CH), 125.9 (CH), 56.2 (C), 55.6 ($CH_2$), 54.7 ($CH_2$), 45.7 ($CH_2$), 43.6 ($CH_2$), 42.9 ($CH_3$), 42.8 ($CH_3$), 42.2 ($CH_2$), 24.2 ($CH_2$), 23.1 ($CH_2$); EI-MS m/z ($M^+$) calcd for $C_{31}H_{41}N_3O$: 471.3250, obsd 471.3254.

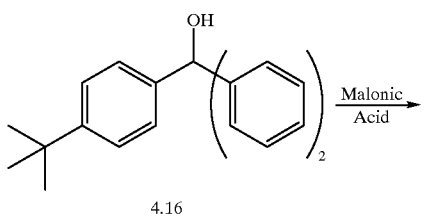

4.16

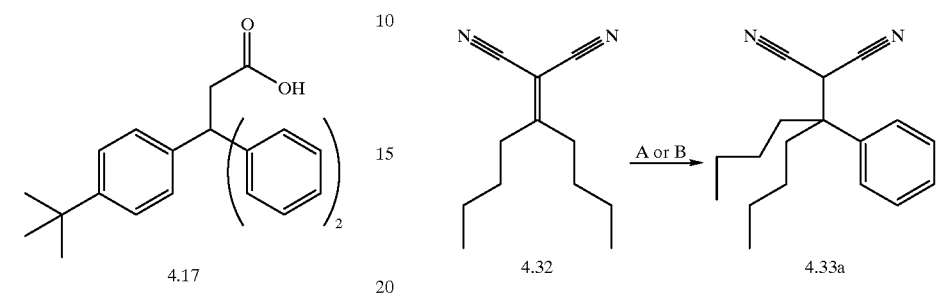

4.17

Preparation of 3-p-tert-butylphenyl-3,3-diphenylpropionic acid (4.17).

The alcohol 1-p-tert-butylpheny-1,1-diphenylmethanol (9.42 g, 29.8 mmol) was combined with malonic acid (4.96 g, 47.7 mmol) in a mortar and ground together well with a pestle. The finely ground mixture was placed into a pear-shaped 100 mL round bottom flask and heated to 140–170° C. The solid slowly melted to form a bright red mixture which bubbled vigorously. The reaction was heated until the solution stopped bubbling and was allowed to cool to room temperature. The resulting white solid was recrystallized from ethanol providing 4.48 g (42%) of a white crystalline solid after recrystallization from ethyl acetate/hexanes. IR (KBr): 2964–2724 (br), 1718 (C=O), 1413 $^1$H NMR (CDCl$_3$): δ 1.28 (s,9H); 3.69 (s 2H); 7.08–7.25 (m, 15H); $^{13}$C NMR (CDCl$_3$, 75.4): δ 176 (C), 148.4 (C), 146.2 (C), 142.2 (C), 128.6 (CH), 128.3 (CH), 127.4 (CH),125.8 (CH), 124.4 (CH), 54.7 (C), 45.5 (CH$_2$), 34.2 (C), 31.0 (CH$_3$); EI-MS m/z (M$^+$) calcd for C$_{25}$H$_{26}$O$_2$: 358.1932, obsd 358.1931.

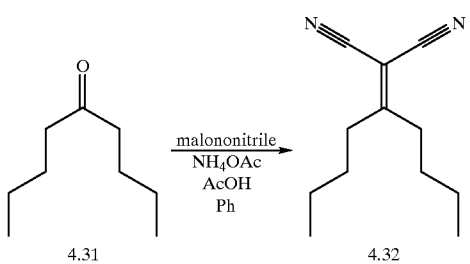

Preparation of 1,1-dicyano-2,2-dibutylethylene 4.32.

5-Nonanone (12.1 mL, 70.3 mmol) was dissolved in benzene (25 mL) containing acetic acid (3.21 mL, 56.4 mmol) and ammonium acetate (1.08 g, 14.1 mmol). The mixture was allowed to stir while malononitrile was added (4.43 mL, 70.3 mmol). The round bottom flask holding the mixture was fitted with a Dean-Stark trap which was filled with benzene and fitted with a reflux condenser. The solution was then refluxed until no more water was being collected by the Dean-Stark trap (4–6 hours). The mixture was cooled and 50 mL of 1 N NaOH was added. The organic layer was separated and washed with 1 N NaOH until no more color was observed in the aqueous layer. The organic layer was dried with MgSO$_4$ and concentrated by rotary evaporation providing 13.38 g (100%) of a yellow oil. IR (KBr): 3424 (br), 2960 (s), 2229 (CN), 1598 (s), 1467. $^1$H NMR (CDCl$_3$): δ 0.961 (t, J=7, 6H); 1.421 (m, 4H); 1.543 (m,4H); 2.57 (t, 4H); $^{13}$C NMR (CDCl$_3$, 75.4): δ 186.5 (C), 111.7 (C), 85.3 (C), 35.3 (CH$_2$), 29.8 (CH$_2$), 22.4 (CH$_2$), 13.4 (CH$_3$): EI-MS m/z (M$^+$) calcd for C$_{12}$H$_{18}$N$_2$: 190.1470, obsd 190.1467.

Preparation of 4.33a.

Method A (see Rabjohn, N.; Phillips, L. V.; Defeo, R. J. *J. Org. Chem.* 1959, 24, 1964): 1,1-dicyano-2,2-dibutylethylene (13.87 g, 73 mmol) was dissolved in dry ether (100 mL) and a catalytic amount of copper (I) iodide (364 mg, 5 g/mol) was added. The reaction was cooled to 0° C. and phenylmagnesium bromide was added (48.5 mL, 3 M in ether) dropwise. After approximately 5 mL of phenylmagnesium bromide the reaction turned black. The reaction was allowed to warm to room temperature after addition was complete and the reaction was stirred overnight. The next day the reaction was quenched by pouring the black solution over an ice/sat. ammonium acetate solution. The biphasic solution was allowed to stir until both layers were homogeneous and the aqueous layer was bright blue. The organic layer was collected and washed with three 50 mL portions of sat. ammonium acetate. The organic layer was dried with MgSO$_4$, concentrated, and applied to a silica gel column. The product was eluted with 9:1 hexanes:ethyl acetate yielding 8.02 g (41%) of a light yellow oil.

Method B (a modification of Davis, A. P.; Orchard, M. G. *J. Chem. Soc. Perkins Trans. I* 1993, 919–924: Phenylmagnesium bromide (107.6 mL, 3 M in ether) was cannulated into a flame dried round bottom flask and then diluted with 50 mL of THF. Copper (I) cyanide was added and the heterogeneous mixture was allowed to stir until the solution became a black homogeneous solution. A solution of 4.32 (11.01 g, 63 mmol) in THF (100 mL) was added dropwise. The addition of 4.32 resulted in the formation of a thick white precipitate that caused stirring to cease. The flask was agitated by hand during the remainder of the addition. The reaction was quenched by adding 75 mL of sat. ammonium chloride. The mixture was filtered through a celite pad eluting with ether. The filtrate was separated and the ether layer was washed with three 50 mL portions of sat. ammonium chloride. The organic layer was dried with MgSO$_4$, concentrated, and preabsorbed onto silica gel. The material was then chromatographed on a silica gel column eluting with 9.5:1.5 ethyl acetate:hexanes. The fractions containing product were pooled and concentrated yielding 11 g (~65%) of a slightly impure yellow oil. IR (KBr): 2985–2873 (br), 2252 (CN), 1467 (s); $^1$H NMR (CDCl$_3$): δ 0.930 (t, J=7, 6H); 1.226 (m, 4H); 1.377 (m, 4H); 2.03 (m, 4H); 3.90 (s, 1H); 7.34–7.44 (m, 5H); $^{13}$C NMR (CDCl$_3$, 75.4): δ 139.1 (C), 128.7 (CH), 127.8 (CH), 126.3 (CH), 111.7 (C), 46.7 (C), 32.9 (CH$_2$), 33.8 (CH), 25.6 (CH$_2$), 22.4 (CH$_2$), 13.7 (CH$_3$); EI-MS m/z (M$^+$) calcd for C$_{18}$H$_{24}$N$_2$: 268.1939, obsd 268.1933.

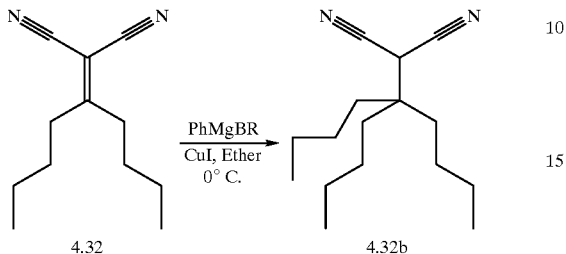

Preparation of 4.33b. The alkylidene, 1,1-dicyano-2,2-dibutylethylene (4.32) (13.65 g, 72 mmol) was dissolved in dry ether (36 mL) and a catalytic amount of copper (I) iodide (360 mg, 5 g/mol) was added. The reaction was cooled to 0° C. and n-butylmagnesium bromide was added (53.7 mL, 2 M in ether) dropwise. After approximately 5 mL of n-butylmagnesium bromide the reaction turned black. The reaction was allowed to warm to room temperature after addition was complete and the reaction was stirred overnight. The next day the reaction was quenched by pouring the black solution over an ice/sat. ammonium acetate solution. The biphasic solution was allowed to stir until both layers were homogeneous and the aqueous layer was bright blue. The organic layer was collected and washed with three 50 mL portions of sat. ammonium acetate. The organic layer was dried with MgSO$_4$, concentrated, and applied to a silica gel column. The product was eluted with 19:1 hexanes:ethyl acetate yielding 10.02 g (59%) of a light yellow oil. IR (KBr): 2958–2871 (br), 2250 (CN), 1467 (s); $^1$H NMR (CDCl$_3$): δ 0.942 (t, J=7, 6H); 1.312 (m, 12H); 1.528 (m, 6H); 3.61 (s, 1H); $^{13}$C NMR (CDCl$_3$, 75.4): δ 112.1 (C), 42.7 (C), 35.4 (CH$_2$), 31.2 (CH), 25.3 (CH$_2$), 22.9 (CH$_2$), 13.7 (CH$_3$); EI-MS m/z (M$^+$H$^-$) calcd for C$_{16}$H$_{27}$N$_2$: 247.2252, obsd 247.2179.

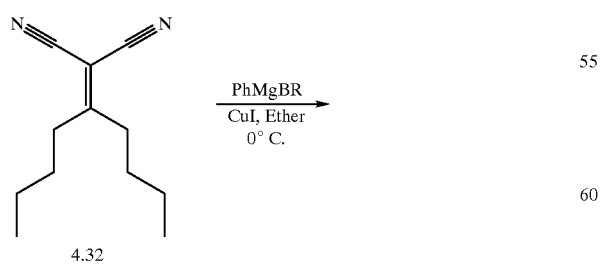

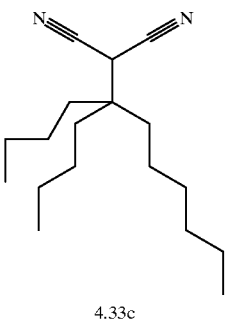

Preparation of 4.33c. The alkylidene, 1,1-dicyano-2,2-dibutylethylene, (4.32) (14 g, 7 mmol) was dissolved in dry ether (50 mL) and a catalytic amount of copper (I) iodide (350 mg, 5 g/mol) was added. The reaction was cooled to 0° C. and n-hexylmagnesium bromide was added (26 mL, 4 M in ether) dropwise. After approximately 5 mL of n-hexylmagnesium bromide the reaction turned black. The reaction was allowed to warm to room temperature after addition was complete and the reaction was stirred overnight. The next day the reaction was quenched by pouring the black solution over an ice/sat. ammonium acetate solution. The biphasic solution was allowed to stir until both layers were homogeneous and the aqueous layer was bright blue. The organic layer was collected and washed with three 50 mL portions of sat. ammonium acetate. The organic layer was dried with MgSO$_4$, concentrated, and applied to a silica gel column. The product was eluted with 19:1 hexanes:ethyl acetate yielding 18.02 g (95.7%) of a light yellow oil. IR (KBr): 2944–2736 (br), 2250 (CN), 1465(s); $^1$H NMR (CDCl$_3$): δ 0.897–0.964 (m, 9H); 1.261–1.557 (m, 30H); 3.61 (s, 1H); $^{13}$C NMR (CDCl$_3$, 75.4): δ 112.1 (C), 42.7 (C), 35.7 (CH$_2$), 35.4 (CH$_2$), 31.2 (CH), 31.1 (CH$_2$), 29.6 (CH$_2$), 25.3 (CH$_2$), 23.1 (CH$_2$), 23.0 (CH$_2$), 22.4 (CH$_2$), 13.8 (CH$_3$), 13.7 (CH$_3$); EI-MS m/z (M$^+$H$^-$) calcd for C$_{18}$H$_{31}$N$_2$: 275.2485, obsd 275.2507.

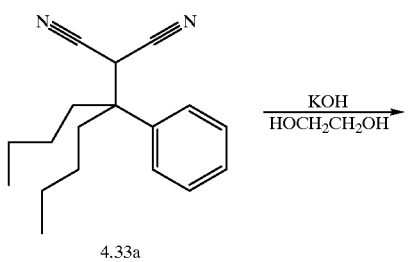

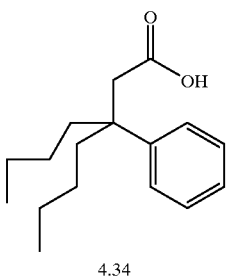

Preparation of 4.34. The dinitrile 4.33a (8 g, 29.8 mmol) was mixed with ethylene glycol (75 mL) and potassium hydroxide (9 g, 160.7 mmol). The mixture was refluxed for 3 days. After 24 hours the reaction foamed, indicating the formation of a surface active species. The reaction was allowed to cool and diluted with 75 mL of water. The solution was poured over ice containing excess concentrated HCl. Upon acidification the product precipitated. The off-white precipitate was then extracted with four 50 mL portions of ether. The organic layers were combined, dried with $MgSO_4$, and concentrated by rotary evaporation. The resulting solid could be recrystallized from ethanol, acetic acid or hexanes. In the above case, ethanol was used and 7 g (90%) of a crystalline product was obtained. IR (KBr): 2948–2865 (br), 1702 (s, C=O), 1319; $^1$H NMR ($CDCl_3$): δ 0.825 (t, J=7, 6H); 0.963–1.275 (m, 6H); 1.78 (dt, J=2, 7, 2H); 2.743 (s, 2H); 7.18–7.33 (m, 5H) $^{13}$C NMR ($CDCl_3$, 75.4): δ 178.0 (C), 145.6 (C), 127.9 (CH), 125.9 (CH), 125.5 (CH), 43.0 (C), 40.7 ($CH_2$), 38.2 ($CH_2$), 25.6 ($CH_2$), 23.0 ($CH_2$), 13.8 ($CH_3$); EI-MS m/z ($M^+H^-$) calcd for $C_{17}H_{28}O_2$: 262.1933, obsd 262.1941.

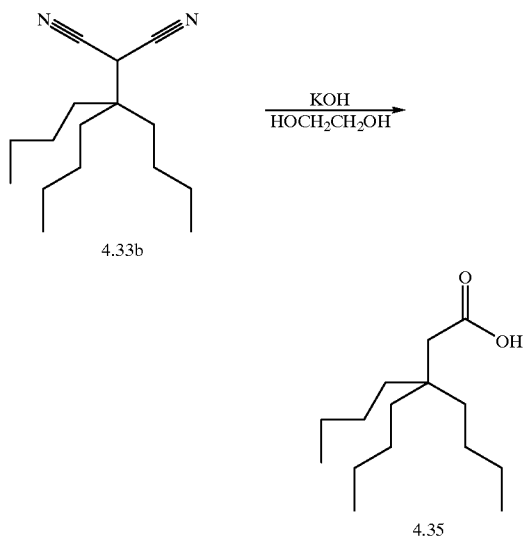

Preparation of 4.35. The dinitrile 4.33b (16.10 g, 64.9 mmol) was mixed with ethylene glycol (50 mL) and potassium hydroxide (10 g, 179 mmol). The mixture was refluxed for 3 days. After 24 hours the reaction foamed, indicating the formation of a surface active species. The reaction was allowed to cool and diluted with 75 mL of water. The solution was poured over ice containing excess concentrated HCl. Upon acidification the product precipitated. The off-white precipitate was then extracted with four 50 mL portions of ether. The organic layers were combined, dried with $MgSO_4$, and concentrated by rotary evaporation. The resulting solid could be recrystallized from ethanol, acetic acid or hexanes. In the above case, ethanol was used and 17.4 g (90%) of a crystalline product was obtained. IR (KBr): 2935–2858 (br), 1702 (s, C=O), 1467; $^1$H NMR ($CDCl_3$): δ 0.902 (t, J=7, 9H); 1.156–1.330 (m, 18H); 2.226 (s, 2H); $^{13}$C NMR ($CDCl_3$, 75.4): δ 179.0 (C), 41.1 ($CH_2$), 38.1 (C), 36.2 ($CH_2$), 25.1 ($CH_2$), 23.0 ($CH_2$), 13.9 ($CH_3$); EI-MS m/z ($M^+$) calcd for $C_{15}H_{30}O_2$: 242.2245, obsd 242.2236.

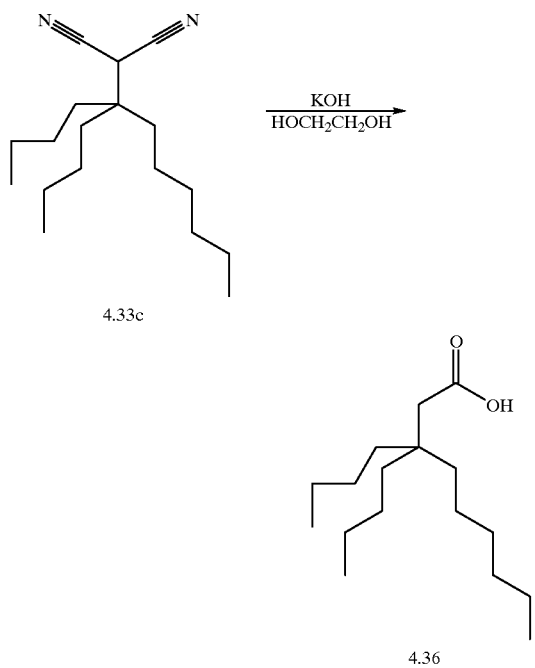

Preparation of 4.36. The dinitrile 4.33c (18.50 g, 67 mmol) was mixed with ethylene glycol (75 mL) and potassium hydroxide (15 g, 268 mmol). The mixture was refluxed for 3 days. After 24 hours the reaction foamed, indicating the formation of a surface active species. The reaction was allowed to cool and diluted with 75 mL of water. The solution was poured over ice containing excess concentrated HCl. Upon acidification the product precipitated. The off-white precipitate was then extracted with four 50 mL portions of ether. The organic layers were combined, dried with $MgSO_4$, and concentrated by rotary evaporation. The oil was determined by $^1$H NMR to be a mixture of product and partially hydrolyzed starting material. A new set of conditions was applied to the mixture in which the oil was refluxed in a 1:1 mixture of AcOH and concentrated HCl. After refluxing the solution for 24 hours the solution was diluted carefully with water and extracted with ether yielding approx. 7 g (30%) of a clear oil. IR (KBr): 2881–2730 (br), 1704 (s, C=O), 1465; $^1$H NMR ($CDCl_3$): δ 0.902 (m, 9H); 1.181–1.311 (m, 22H); 2.225 (s, 2H); $^{13}$C NMR ($CDCl_3$, 75.4): δ 178.6 (C), 41.0 ($CH_2$), 38.1 (C), 36.5 ($CH_2$), 36.2 ($CH_2$), 31.6 ($CH_2$), 36.2 ($CH_2$), 29.8 ($CH_2$), 25.1 ($CH_2$), 23.2 ($CH_2$), 22.7 ($CH_2$), 22.5 ($CH_2$), 13.9 ($CH_3$); EI-MS m/z ($M^+$) calcd for $C_{17}H_{34}O_2$: 270.2558, obsd 242.2639.

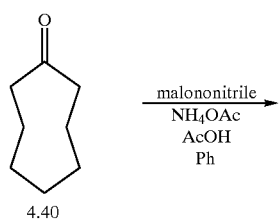

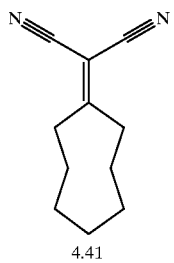

4.41

Preparation of 4.41. Cyclooctanone, (10 mL, 79.2 mmol) was dissolved in benzene (25 mL) containing acetic acid (3.63 mL, 63.6 mmol) and ammonium acetate (1.22 g 15.9 mmol). The reaction was allowed to stir while malononitrile was added (4.99 mL, 79.2 mmol). The round bottom flask holding the mixture was fitted with a Dean-Stark trap which was filled with benzene and fitted with a reflux condenser. The solution was then refluxed until no more water was being collected by the Dean-Stark trap (4–6 hours). The mixture was cooled and 50 mL of 1 N NaOH was added. The organic layer was separated and washed with 1 N NaOH until no more color was observed in the aqueous layer. The organic layer was dried with $MgSO_4$ and concentrated by rotary evaporation providing 13.38 g (100%) of a yellow oil. IR (KBr): 2861–2697 (br), 2227 (s, CN), 1579); $^1$H NMR ($CDCl_3$): δ 1.381 (m, 2H); 1.543 (m, 4H); 1.933 (m, 4H); 2.726 (m, 4H); $^{13}$C NMR ($CDCl_3$, 75.4): δ 191.2 (C), 111.8 (C), 84.3 (C), 35.1 ($CH_2$), 26.5 ($CH_2$), 26.2 ($CH_2$), 25.1 ($CH_2$); EI-MS m/z (M$^+$) calcd for $C_{11}H_{14}N_2$: 174.1156, obsd 174.1155.

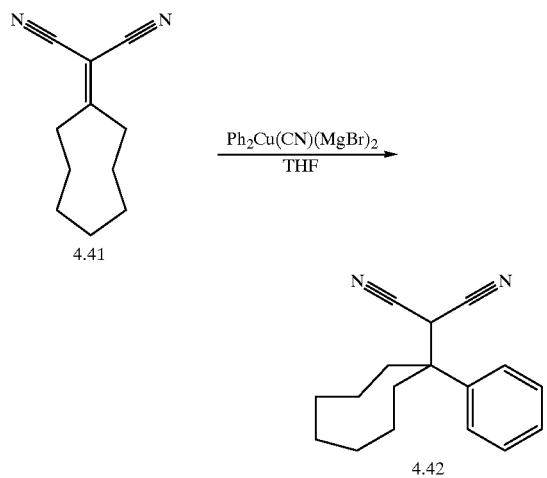

Preparation of 4.42. Phenylmagnesium bromide (107.6 mL,3 M in ether) was cannulated into a flame dried round bottom flask and then diluted with 50 mL of THF. Copper (I) cyanide was added and the heterogeneous mixture was allowed to stir until the solution became a black homogeneous solution. A solution of 4.41 (11.01 g, 63 mmol) in THF (100 mL) was added dropwise. The addition of 4.41 resulted in the formation of a thick white precipitate that caused stirring to cease. The flask was agitated by hand during the remainder of the addition. The reaction was quenched by adding 75 mL of sat. ammonium chloride. The mixture was filtered through a celite pad eluting with ether. The filtrate was separated and the ether layer was washed with sat. ammonium chloride three times with 50 mL portions. The organic layer was dried with $MgSO_4$, concentrated, and preabsorbed onto silica gel. The material was then chromatographed on a silica gel column eluting with 5:4 toluene:hexanes. The fraction containing product was pooled and concentrated yielding 10 g (65%) of a slightly impure yellow oil. IR (KBr): 2923–2757 (br), 2250 (w, CN); $^1$H NMR ($CDCl_3$): δ 1.452–1.713 (m, 12H); 2.131–2.214 (m, 2H); 2.421–2.501 (m, 2H); 3.739 (s, 1H); 7.233–7.492 (m, 5H); $^{13}$C NMR ($CDCl_3$, 75.4): δ 138.5 (C), 128.8 (CH), 128.1 (CH), 127.3 (CH), 111.7(C),47.9 (C), 37.2 (CH), 31.2 ($CH_2$),27.7 ($CH_2$), 24.0 ($CH_2$), 22.4 ($CH_2$); EI-MS m/z (M$^+$H$^-$) calcd for $C_{17}H_{19}N_2$: 251.1546, obsd 251.1561.

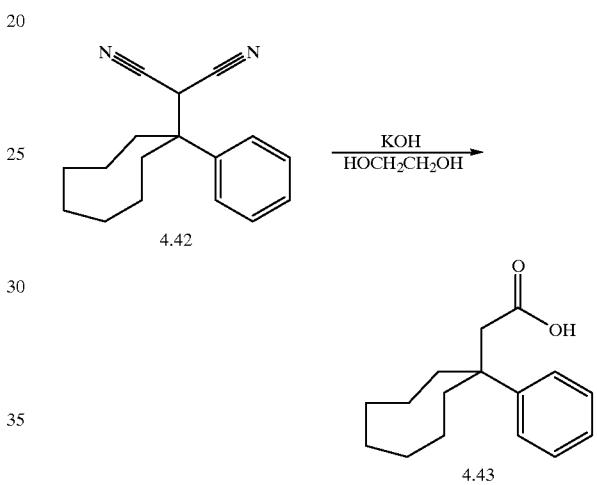

Preparation of 4.43. The dinitrile 4.42 (10.33 g, 41 mmol) was mixed with ethylene glycol (70 mL) and potassium hydroxide (13 g, 232 mmol). The mixture was refluxed for 3 days. After 24 hours the reaction foamed, indicating the formation of a surface active species. The reaction was allowed to cool and diluted with 75 mL of water. The solution was poured over ice containing excess concentrated HCl. Upon acidification the product precipitated. The off-white precipitate was then extracted with four 50 mL portions of ether. The organic layers were combined, dried with $MgSO_4$, and concentrated by rotary evaporation. The resulting solid could be recrystallized from ethanol, acetic acid or hexanes. Hexanes worked very well and are easily removed. In the above case, ethanol was used and 8.3 g (80%) of a crystalline product was obtained. IR (KBr): 3396 (br); 2921–2817 (br), 1689 (w, C=O); $^1$H NMR ($CDCl_3$): δ 1.461–1.543 (m, 10H); 1.943–2.167 (m, 4H); 2.539 (s, 2H); 7.168–7.342 (m, 5H); $^{13}$C NMR ($CDCl_3$, 75.4): δ 177.6 (C), 145.9 (CH), 128.0 (CH), 126.7 (CH) 125.8 (C), 47.1 ($CH_2$), 43.8 (C), 33.3 ($CH_2$), 28.4 ($CH_2$), 25.1 ($CH_2$), 22.9 ($CH_2$); EI-MS m/z (M$^+$H$^-$) calcd for $C_{16}H_{22}O_2$: 246.1618, obsd 246.1634.

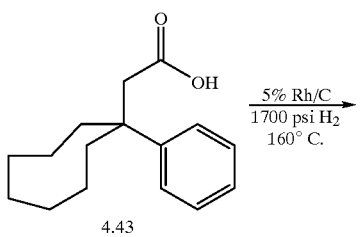

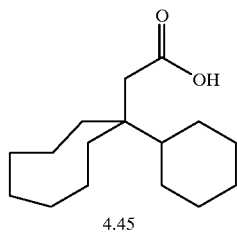

Preparation of 4.45. The acid 4.43 (1 g, 4 mmol) was dissolved in 10 mL of acetic acid and 5% rhodium on carbon (300 mg) was added along with a stir bar. The reaction mixture which was in a glass sleeve was placed in a small reaction bomb and the bomb was sealed. Hydrogen pressure of 1700 psi was charged into the bomb and the bomb was heated to 150° C. for 36 hours. The bomb was cooled and the solution was filtered over celite to remove the catalyst eluting with ethyl acetate. The solution was concentrated and the residue was recrystallized from ethanol/water yielding 857 mg (85%) of a slightly pink solid. IR (KBr): 2925–2786 (br), 1695 (w, C=O); $^1$H NMR (CDCl$_3$): δ 1.122–1.782 (m, 25H); 2.176 (s,2H); $^{13}$C NMR (CDCl$_3$, 75.4): δ 179.6 (C), 45.7 (CH), 41.5 (CH$_2$), 32.1 (CH$_2$), 28.6 (CH$_2$), 27.1 (CH$_2$), 26.6 (CH$_2$), 25.8 (CH$_2$), 23.1 (CH$_2$); EI-MS m/z (M$^+$CH$_3$CO$_2^-$) calcd for C$_{14}$H$_{24}$: 192.346, obsd 192.190.

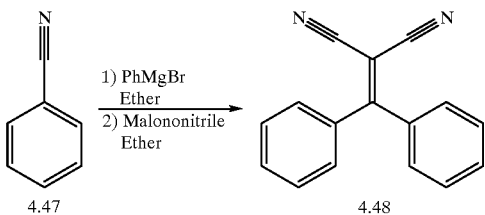

Preparation of 4.48. Benzonitrile 4.47 (5.1 mL, 50 mmol) was dissolved in 100 mL of dry ether and reacted with phenylmagnesium bromide (15.8 mL, 3 M in ether, 47.4 mmol). Addition of the Grignard reagent caused a precipitate to form and the solution became difficult to stir. The solution was allowed to stir for 30 minutes after which the reaction was quenched with ethereal malononitrile (4.72 mL, 75 mmol, in 100 mL ether). The reaction was allowed to stir for an hour more. The solution was washed once with 1 N HCl, three times with 1 N NaOH, and dried with MgSO$_4$. The concentration of the solution yielded 8.06 g (70%) of pure off-white solid product. IR (KBr): 2784 (br), 2221 (s, CN), 1531; $^1$H NMR (CDCl$_3$): δ 7.254–7.612 (m, 10H); $^{13}$C NMR (CDCl$_3$, 75.4): δ 174.8 (C), 135.8 (C), 132.4 (CH) 130.4 (CH), 130.2 (CH), 128.7 (CH), 113.7 (C); EI-MS m/z (M$^+$) calcd for C$_{16}$H$_{10}$N$_2$: 230.0844, obsd 230.0853.

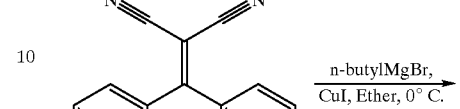

Preparation of 4.49a. The alkylidene, 1,1-dicyano-2,2-diphenylethylene, (4.48) (1 g, 4.3 mmol) was dissolved in dry ether (25 mL) and a catalytic amount of copper (I) iodide (21 mg, 5 g/mol) was added. The reaction was cooled to 0° C. and n-butylmagnesium bromide was added (4.3 mL, 2 M in ether, 8.86 mmol ) dropwise. After approximately 1 mL of n-butylmagnesium bromide the reaction turned black. The reaction was allowed to warm to room temperature after addition was complete and the reaction was stirred overnight. The next day the reaction was quenched by pouring the black solution over an ice/sat. ammonium acetate solution. The biphasic solution was allowed to stir until both layers were homogeneous and the aqueous layer was bright blue. The organic layer was collected and washed with three 50 mL portions of sat. ammonium acetate. The organic layer was dried with MgSO$_4$, concentrated, and applied to a silica gel column. The product was eluted with 19:1 I hexanes-:ethyl acetate yielding 512 mg (41%) of a light yellow oil. IR (KBr): 3062–2740 (br), 2254 (w, CN), 1444; $^1$H NMR (CDCl$_3$): δ 0.8287 (t, J=7 Hz, 3H); 0.969–1.042 (m, 2H); 1.287 (h, J=7, Hz, 2H); 2.334–2.390 (m, 2H); 7.245–7.422 (m, 10H); $^{13}$C NMR (CDCl$_3$, 75.4): δ 140.4(C), 128.3 (CH), 128.0 (CH), 127.9 (CH), 111.8 (C), 53.3 (C); 38.7 (CH$_2$); 33.4 (CH); 26.5 (CH$_2$); 22.5 (CH$_2$); 13.5 (CH$_3$); EI-MS m/z (M$^+$) calcd for C$_{20}$H$_{20}$N$_2$: 288.1626, obsd 288.1639.

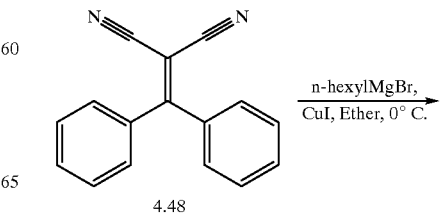

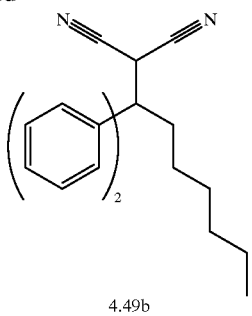

4.49b

Preparation of 4.49b. The alkylidene, 1,1-dicyano-2,2-diphenylethylene, (4.48) (3.14 g, 13.6 mmol) was dissolved in dry ether (25 mL) and a catalytic amount of copper (I) iodide (68 mg, 5 g/mol) was added. The reaction was cooled to 0° C. and n-hexylmagnesium bromide was added (13.6 mL, 2 M in ether, 27.2 mmol) dropwise. After approximately 3 mL of n-hexylmagnesium bromide the reaction turned black. The reaction was allowed to warm to room temperature after addition was complete and the reaction was stirred overnight. The next day the reaction was quenched by pouring the black solution over an ice/sat. ammonium acetate solution. The biphasic solution was allowed to stir until both layers were homogeneous and the aqueous layer was bright blue. The organic layer was collected and washed with three 50 mL portions of sat. ammonium acetate. The organic layer was dried with MgSO$_4$, concentrated, and applied to a silica gel column. The product was eluted with 19:1 hexanes:ethyl acetate yielding 2.15 g (50%) of a light yellow oil. IR (KBr): 3062–2740 (br), 2254 (w, CN), 1444; $^1$H NMR (CDCl$_3$): δ 0.826 (t, J=7 Hz, 3H); 0.883–1.269 (m, 8H); 3.350 (m, 2H); 4.60 (s, 1H); 7.243–7.41 (m, 10H); $^{13}$C NMR (CDCl$_3$, 75.4): δ 140.4 (C), 128.3 (CH), 128.0 (CH), 127.9 (CH), 111.8 (C), 53.3 (C); 38.9 (CH$_2$); 33.4 (CH); 31.2 (CH$_2$); 29.1 (CH$_2$); 23.9 (CH$_2$); 22.2 (CH$_2$); 13.7 (CH$_3$); EI-MS m/z (M$^+$H$^+$) calcd for C$_{22}$H$_{24}$N$_2$: 317.2019, obsd 317.2033.

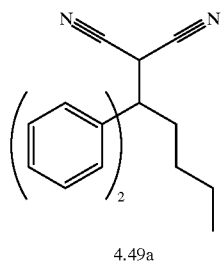

4.49a

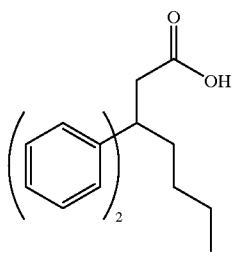

4.50

Preparation of 4.50. The dinitrile 4.49a (3.20 g, 11 mmol) was mixed with ethylene glycol (75 mL) and potassium hydroxide (10 g, 178 mmol). The mixture was refluxed for 3 days. After 24 hours the reaction foamed, indicating the formation of a surface active species. The reaction was allowed to cool and diluted with 75 mL of water. The solution was poured over ice containing excess concentrated HCl. Upon acidification the product precipitated. The off-white precipitate was then extracted with four 50 mL portions of ether. The organic layers were combined, dried with MgSO$_4$, and concentrated by rotary evaporation. The product was recrystallized from ethanol and X-ray quality crystals obtained. The reaction yielded 2.88 g (93%). IR (KBr): 2927 (v.br), 1704 (s, C=O); $^1$H NMR (CDCl$_3$): δ 0.808 (t, J=7 Hz, 3H); 0.955–1.035 (m, 2H); 1.250 (h, J=7 2H); 2.293 (m, 2H); 3.129 (s, 2H) 7.106–7.274 (m, 10H); $^{13}$C NMR (CDCl$_3$, 75.4): δ 172.1 (C), 147.1 (C), 127.7 (CH), 127.4 (CH), 125.9 (CH), 48.3 (C); 42.5 (CH$_2$); 37.4 (CH$_2$); 26.2 (CH$_2$); 23.0 (CH$_2$); 13.8 (CH$_3$); EI-MS m/z (M$^+$) calcd for C$_{19}$H$_{22}$O$_2$: 282.1620, obsd 282.1612.

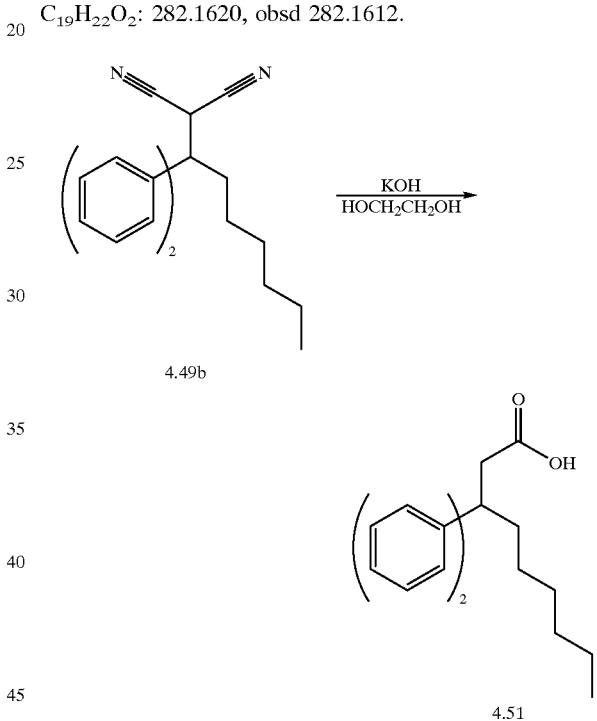

4.49b 4.51

Preparation of 4.51. The dinitrile 4.49b (2.92 g, 9.2 mmol) was mixed with ethylene glycol (50 mL) and potassium hydroxide (10 g, 178 mmol). The mixture was refluxed for 3 days. After 24 hours the reactions foamed, indicating the formation of a surface active species. The reaction was allowed to cool and diluted with 75 mL of water. The solution was poured over ice containing excess concentrated HCl. Upon acidification the product precipitated. The off-white precipitate was then extracted with four 50 mL portions of ether. The organic layers were combined, dried with MgSO$_4$, and concentrated by rotary evaporation. The resulting oil slowly crystallized after sitting for many weeks. The reaction yielded 2 g (70%) of the desired product. $^1$H NMR (CDCl$_3$): δ 0.824 (t, J=7 Hz, 3H); 1.014–1.260 (m, 8H); 2.290 (m, 2H); 3.136 (s, 2H) 7.122–7.279 (m, 10H); $^{13}$C NMR (CDCl$_3$, 75.4): δ 176.2 (C), 147.0 (C), 127.7 (CH), 127.4 (CH), 125.8 (CH), 48.3 (C); 42.3 (CH$_2$); 37.6 (CH$_2$); 31.4 (CH$_2$); 29.5 (CH$_2$); 23.9 (CH$_2$); 22.4 (CH$_2$), 13.8

(CH₃); EI-MS m/z (M⁺) calcd for $C_{21}H_{26}O_2$: 310.1933, obsd 310.1954.

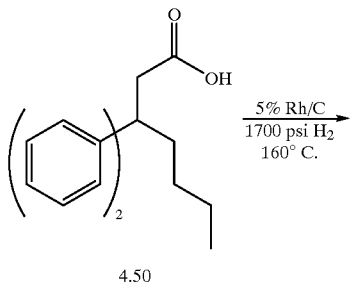

4.50

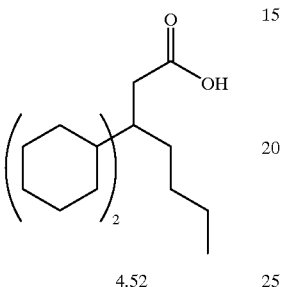

4.52

Preparation of 4.52. The acid 4.50 (3.37 g, 12 mmol) was dissolved in 15 mL of acetic acid and 5% rhodium on carbon (300 mg) was added along with a stir bar. The reaction mixture which was in a glass sleeve was placed in a small reaction bomb and the bomb was sealed. Hydrogen pressure of 2000 psi was charged into the bomb and the bomb was heated to 150° C. for 24 hours. The bomb was cooled and the solution was filtered over celite to remove the catalyst eluting with ethyl acetate. The solution was concentrated and chromatographed on a silica gel column eluting with 19:1 hexanes:ethyl acetate. The fractions containing product were pooled and concentrated yielding 2.9 g (50%) of a crystalline product which was recrystallized from ethanol. IR (KBr): 2925–2726 (br), 1700 (s, C=O); ¹H NMR (CDCl₃): δ 0.866–1.751 (m, 28H); 2.450 (s, 2H); 11 (br,s, 1H) ¹³C NMR (CDCl₃, 75.4): δ 180 (C), 48.8 (C); 43.2 (CH); 39.3 (CH₂); 33.9 (CH₂); 28.3 (CH₂); 28.2 (CH₂); 27.2 (CH₂); 27.5 (CH₂); 26.9 (CH₂); 26.7 (CH₂); 25.3 (CH₂); 13.8 (CH₃); EI-MS m/z (M⁺2H⁻) calcd for $C_{19}H_{34}O_2$: 292.2399, obsd 292.2390.

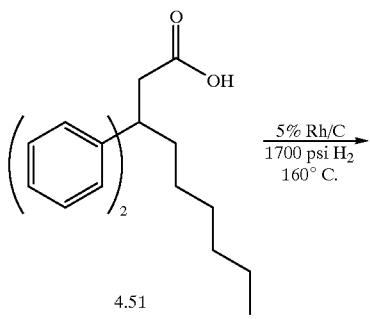

4.51

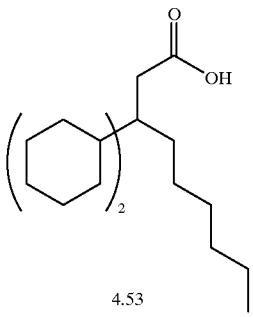

4.53

Preparation of 4.53. The acid 4.51 (3.2 g, 11 mmol) was dissolved in 15 mL of acetic acid and 5% rhodium on carbon (300 mg) was added along with a stir bar. The reaction mixture which was in a glass sleeve was placed in a small reaction bomb and the bomb was sealed. Hydrogen pressure of 2000 psi was charged into the bomb and the bomb was heated to 150° C. for 96 hours. The bomb was cooled and the solution was filtered over celite to remove the catalyst eluting with ethyl acetate. The solution was concentrated and chromatographed on a silica gel column eluting with 19:1 hexanes:ethyl acetate. The fractions containing product were pooled and concentrated yielding 1.67 g (47%) of a clear oil. ¹H NMR (CDCl₃): δ 0.907 (t, J=7 Hz, 3H); 1.117–1.749 (m, 32H); 2.262 (s, 2H) ¹³C NMR (CDCl₃, 75.4): d 179.8 (C), 43.8 (C); 43.2 (CH); 39.2 (CH₂); 34.3 (CH₂); 31.6 (CH₂); 30.4 (CH₂); 28.35 (CH₂); 28.29 (CH₂); 27.5 (CH₂); 27.3 (CH₂); 26.7 (CH₂); 24.6 (CH₂); 22.5 (CH₂); 13.8 (CH₃); EI-MS m/z (M⁺H⁺) calcd for $C_{21}H_{39}O_2$: 323.2952, obsd 323.2959.

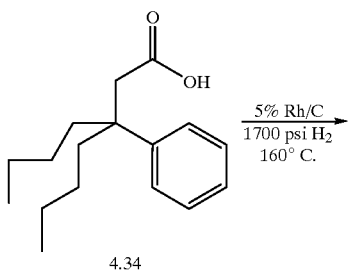

4.34

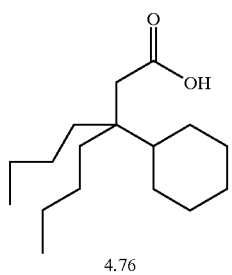

4.76

Preparation of 4.76. The acid 4.34 (6.8 g, 25.9 mmol) was dissolved in 15 mL of acetic acid and 5% rhodium on carbon (600 mg) was added along with a stir bar. The reaction mixture which was in a glass sleeve was placed in a small reaction bomb and the bomb was sealed. Hydrogen pressure of 2000 psi was charged into the bomb and the bomb was heated to 150° C. for 4 days. The bomb was cooled and the solution was filtered over celite to remove the catalyst eluting with ethyl acetate. The solution was concentrated and chromatographed on a silica gel column eluting with 19:1 hexanes:ethyl acetate. The fractions containing product were pooled and concentrated yielding 4 g (58%) of a clear oil. IR (KBr): 2929–2726 (br), 1702 (s, C=O); $^1$H NMR (CDCl$_3$): δ 0.902 (t, J=7 Hz, 6H); 1.029–1.786 (m, 23H); 2.240 (s, 2H); 11 (br, s $^1$H), $^{13}$C NMR (CDCl$_3$, 75.4): δ 179.5 (C), 44.9 (CH); 40.8 (C); 39.9 (CH$_2$); 35.2 (CH$_2$); 27.2 (CH$_2$); 26.6 (CH$_2$); 25.9 (CH$_2$); 23.5 (CH$_2$); 13.9 (CH$_3$); EI-MS m/z (M$^+$) calcd for C$_{17}$H$_{32}$O$_2$: 222.416, obsd 223.238.

Preparation of 4.61. The alcohol 4.60 (See *Org. Syn. III*, 831) (2.62 g, 5.4 mmol) was ground together with malonic acid (5.58 g, 54 mmol) and the mixture was heated to 170° C. At approximately 150° C., the solids began to melt together and form a red syrup. The reaction bubbled vigorously for about 1.5 hours and then ceased to bubble. Once bubbling stopped the reaction was cooled. Upon cooling the syrup solidified to a off-white solid which was recrystallized from ethanol yielding 2.12 g (74%). IR (KBr): 3025–2846 (br), 1716 (s, C=O), 1484; $^1$H NMR (CDCl$_3$): δ 3.86 (s, 2H); 7.321–7.615 (m, 27H); 9.0 (s, 1H); $^{13}$C NMR (CDCl$_3$, 75.4): δ 177.5 (C), 145.1 (C); 140.3 (C); 138.8 (C); 129.3 (CH), 128.6 (CH); 128.1 (CH); 127.0 (CH); 126.8 (CH); 126.3 (CH); EI-MS m/z (M$^+$) calcd for C$_{39}$H$_{30}$O$_2$: 530.2246, obsd 530.2239.

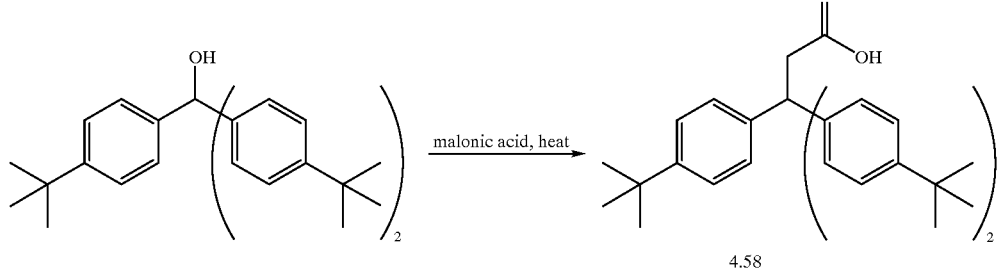

4.58

Preparation of 3,3,3-tri-p-tert-butylphenylacetic acid (4.58). Alcohol tris-t-butylphenylmethanol (3.8 g, 8.9 mmol) was ground together with malonic acid (9.23 g, 89 mmol) and the mixture was heated to 170° C. At approximately 150° C., the solids began to melt together and form a red syrup. The reaction bubbled vigorously for about 1.5 hours and then ceased to bubble. Once bubbling stopped the reaction was cooled. Upon cooling the syrup solidified to an off-white solid which was recrystallized from ethanol yielding 3 g (72%). IR (KBr): 3031–2748 (br), 1700 (s, C=O), 1508; $^1$H NMR (CDCl$_3$): δ 1.288 (s, 27H); 3.684 (s, 2H); 7.087 (d, J=9, 6H); 7.243 (d, J=9, 6H); $^{13}$C NMR (CDCl$_3$, 75.4): δ 175 (C), 148.4 (C); 143.2 (C); 128.3 (CH); 124.2 (CH); 45.4 (CH$_2$); 33.9 (C); 30.9 (CH$_3$); EI-MS m/z (M$^+$) calcd for C$_{33}$H$_{42}$O$_2$: 470.3185, obsd 470.3197.

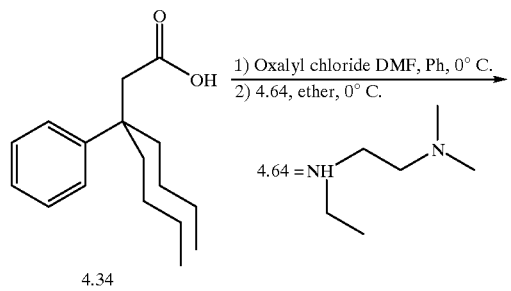

4.34

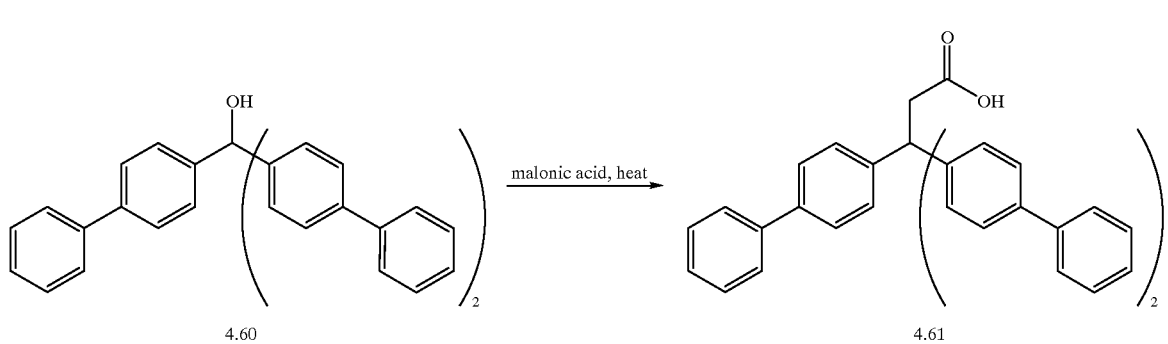

4.60   4.61

-continued

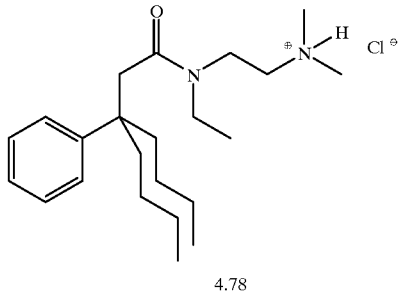

4.78

-continued

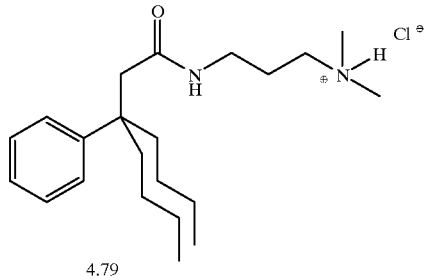

4.79

Preparation of 4.78. The acid 4.34 (2.43 g, 9.3 mmol) was dissolved in 5 mL of benzene in a round bottom flask. One drop of DMF was added as a catalyst and the solution was cooled with an ice bath. Once the solution had cooled the oxalyl chloride (4.04 mL, 46.5 mmol) was added dropwise resulting in a vigorously bubbling solution. The reaction was allowed to stir 3 hours and the volatiles were removed under vacuum. The residue was dissolved in dry ether (50 mL), cooled to 0° C., and amine 4.64 (2.92 mL, 18.6 mmol) in ether (50 mL) was added dropwise resulting in a white precipitate. The solution was allowed to stir overnight. The next day 1 N NaOH (25 mL) was added and the precipitate dissolved. The layers were separated and the ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 3.35 g (100%) of a light yellow solution. The oil was dissolved in 30 mL of ether and the amine was precipitated by adding 4 N HCl in dioxane (2.3 mL) diluted in 30 mL of ether. The off-white solid was recrystallized from methylene chloride/hexanes. IR (Kbr Free amine): 2954–2769 (br), 1637 (s, C=O), 1457; $^1$H NMR ($CDCl_3$, Free Amine): δ 0.89 (dt, J=3.5, 7, 6H); 0.967 (dt, J=7,18, 3H); 1.046–1.364 (m, 8H); 1.844–2.025 (m, 4H); 2.285 (s, 3H); 2.218 (s,3H); 2.20–2.271 (m, 2H); 2.518 (s, 1H); 2.547 (s, 1H); 2.812 (m, 1H); 2.941 (AB, J=7, 1H); 3.219 (AB, J=7, 1H); 3.291 (m, 1H); 7.138–7.358 (m, 5H); $^{13}$C NMR ($CDCl_3$, 75.4. HCl Salt): δ 171.5 (C), 146.2 (C); 127.8 (CH); 126.1 (CH), 125.6 (CH); 54.0 ($CH_2$); 43.6 ($CH_2$); 43.1 (C); 42.7 ($CH_3$); 40.8 ($CH_2$); 40.5 ($CH_2$); 36.1 ($CH_2$); 25.6 ($CH_2$); 23.1 ($CH_2$); 13.9 ($CH_3$); MALDI-TOF ($M^+H^+$) calcd for $C_{23}H_{41}N_2O$ 361.59, obsd 361.32; ($M^+Na^+$) calcd for $C_{23}H_{40}N_2ONa$: 384.59, obsd 384.26.

Preparation of 4.79. The acid 4.30 (300 mg, 1.1 mmol) was dissolved in 5 mL of benzene in a round bottom flask. One drop of DMF was added as a catalyst and the solution was cooled with an ice bath. Once the solution had cooled the oxalyl chloride (0.499 mL, 5.72 mmol) was added dropwise resulting in a vigorously bubbling solution. The reaction was allowed to stir 3 hours and the volatiles were removed under vacuum. The residue was dissolved in dry ether (15 mL), cooled to 0° C., and N,N-dimethylpropylenediamine (0.288 mL, 2.2 mmol) in ether (15 mL) was added dropwise resulting in a white precipitate. The solution was allowed to stir overnight. The next day 1 N NaOH (25 mL) was added and the precipitate dissolved. The layers were separated and the ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 394 mg (100%) of a light yellow oil. The oil was dissolved in 10 mL of ether and the amine was precipitated by adding 4 N HCl in dioxane (0.285 mL) diluted in 10 mL of ether. The off-white solid was recrystallized from methylene chloride/hexanes. IR (Kbr HCl Salt): 3309 (br), 2954–2769 (s, C=O), 2240 (N—H), 1644 (C=O), 1540, 1465; $^1$H NMR ($CDCl_3$, Free Amine): δ 0.863 (t, J=7, 6H); 1.022–1.318 (m, 8H); 1.375 (p, J=7, 2H); 1.740–1.844 (m, 4H); 2.078–2.124 (m, 2H); 2.136 (s, 6H); 2.491 (s, 2H); 3.062 (app. q, J=6, 3H); 5.530 (t, J=6, 1H); 7.169–7.340 (m, 5H); $^{13}$C NMR ($CDCl_3$, 75.4, Free Amine): δ 170.6(C), 146.6(C); 128.1 (CH); 126.2 (CH), 125.6 (CH); 57.6 ($CH_2$); 46.2 ($CH_2$); 45.2 ($CH_3$); 43.0 (C); 38.0 ($CH_2$); 36.7 ($CH_2$); 23.1 ($CH_2$); 13.8 ($CH_3$).

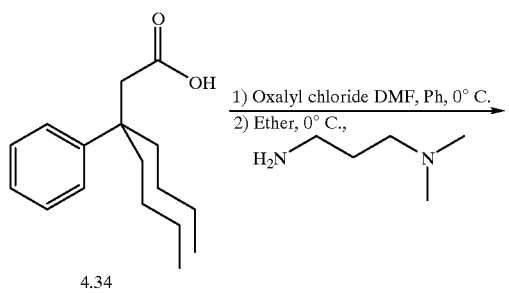

4.34

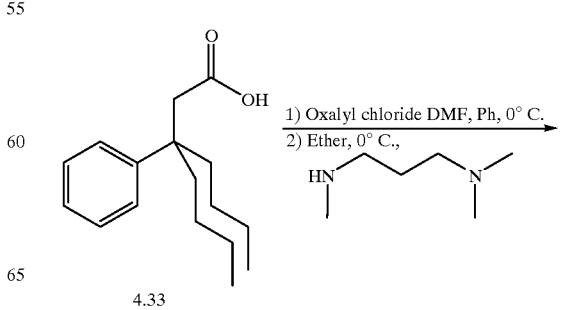

4.33

61

-continued

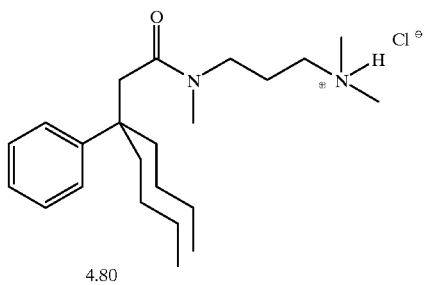

4.80

Preparation of 4.80. The acid 4.33 (211 mg, 0.8 mmol) was dissolved in 5 mL of benzene in a round bottom flask. One drop of DMF was added as a catalyst and the solution was cooled with an ice bath. Once the solution had cooled the oxalyl chloride (0.351 mL, 4.0 mmol) was added dropwise resulting in a vigorously bubbling solution. The reaction was allowed to stir 3 hours and the volatiles were removed under vacuum. The residue was dissolved in dry ether (15 mL), cooled to 0° C., and N,N,N'-trimethylpropylene-diamine (0.236 mL, 1.6 mmol) in ether (15 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 300 mg (99%) of a light yellow oil. The oil was dissolved in 10 mL of ether and the amine was precipitated by adding 4 N HCl in dioxane (0.200 mL) diluted in 10 mL of ether. The off-white solid was recrystallized from methylene chloride/hexanes. IR (KBr HCl Salt): 3442 (br), 2954–2709 (br), 1635 (s, C=O), 1467; $^1$H NMR (CDCl$_3$, HCl Salt): δ 0.863 (t, J=7, 6H); 1.022–1.4 (m, 10H); 1.740–1.844 (m, 6H); 2.62 (s, 3H); 2.68–2.81 (m, 10H); 3.26 (m, 2H); 7.13–7.38 (m, 5H); 11.9 (br, m, 1H) $^{13}$C NMR (CDCl$_3$, 75.4,HCl Salt): δ 171.6 (C), 146.6 (C); 127.7 (CH); 126.1 (CH), 125.4 (CH); 55.3 (CH$_2$); 44.3 (CH$_2$); 42.9 (C); 42.7 (CH$_3$); 40.9 (CH$_2$); 36.1 (CH$_2$); 35.7 (CH$_2$); 25.6 (CH$_2$); 23.1 (CH$_2$); 22.6 (CH$_2$); 13.9 (CH$_3$); MALDI-TOF (M$^+$2H$^+$) calcd for C$_{23}$H$_{42}$N$_2$O: 362.59, obsd 362.40.

62

-continued

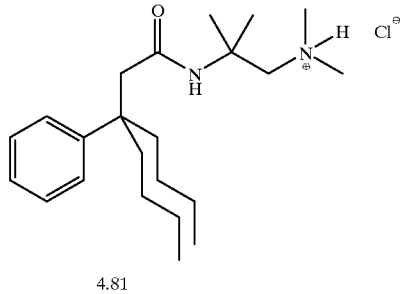

4.81

Preparation of 4.81. The acid 4.33 (500 mg, 1.91 mmol) was dissolved in 5 mL of benzene in a round bottom flask. One drop of DMF was added as a catalyst and the solution was cooled with an ice bath. Once the solution had cooled the oxalyl chloride (0.832 mL, 9.55 mmol) was added dropwise resulting in a vigorously bubbling solution. The reaction was allowed to stir 3 hours and the volatiles were removed under vacuum. The residue was dissolved in dry ether (20 mL), cooled to 0° C., and 1-dimethylaminomethyl-2-aminopropane (0.442 mL, 3.8 mmol) in ether (20 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 630 mg (89%) of a light yellow oil. The oil was dissolved in 10 mL of ether and the amine was precipitated by adding 4 N HCl in dioxane (0.478 mL) diluted in 10 mL of ether. The off-white solid was recrystallized from methylene chloride/hexanes. IR (KBr HCl Salt): 3435 (br), 2934, 2868, 2731 (br), 1666 (s, C=O); $^1$H NMR (CDCl$_3$, HCl Salt): δ 0.877 (t, J=7, 6H); 0.991–1.141 (m, 2H); 1.166 (s, 6H); 1.207–1.338 (m, 4H); 1.745–1.852 (m, 6H); 2.623 (s, 2H); 2.732 (d, J=5, 6H); 3.368 (d, J=3.5, 2H); 7.165–7.421 (m, 5H); 11.2 (br, m, 1H); $^{13}$C NMR (CDCl$_3$, 75.4, HCl Salt): δ 173.2(C), 147(C); 128.2 (CH); 126.5 (CH), 125.4 (CH); 65.3 (CH$_2$); 52 (C); 46.8 (CH$_2$); 46.7 (CH$_3$); 36.1 (CH$_2$); 25.5 (CH$_2$); 25.4 (CH$_3$); 23.1 (CH$_2$); 13.9 (CH$_3$); MALDI-TOF (M$^+$2H$^+$) calcd for C$_{23}$H$_{42}$N$_2$O: 362.59, obsd 362.35.

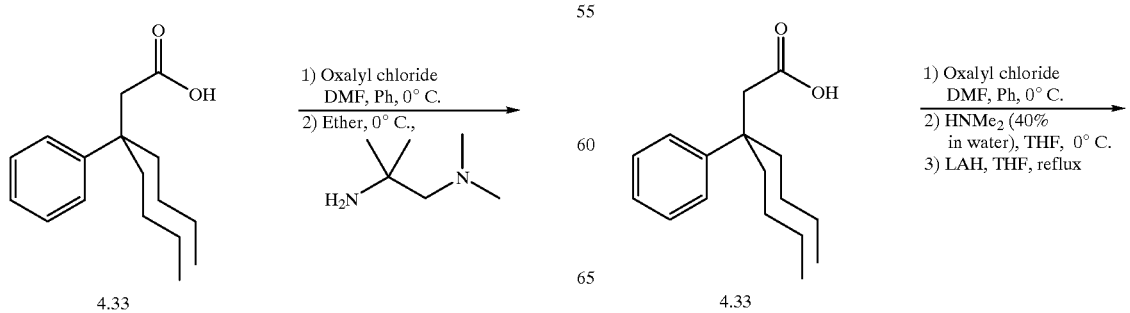

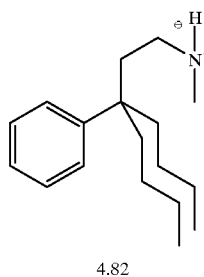

4.82

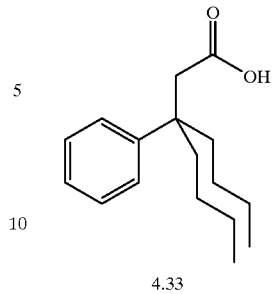

4.33

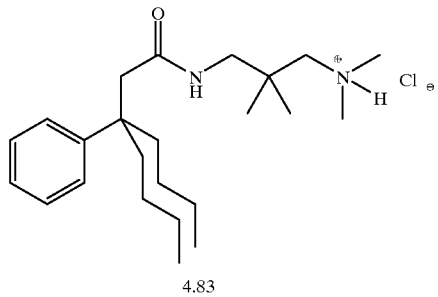

4.83

Preparation of 4.82. The acid 4.33 (500 mg, 1.91 mmol) was dissolved in 5 mL of benzene in a round bottom flask. One drop of DMF was added as a catalyst and the solution was cooled with an ice bath. Once the solution had cooled the oxalyl chloride (0.832 mL, 9.55 mmol) was added dropwise resulting in a vigorously bubbling solution. The reaction was allowed to stir 3 hours and the volatiles were removed under vacuum. The oil was dissolved in dry THF (20 mL), cooled to 0° C., and HNMe$_2$ (20 mL, 40% solution in water) was added. The solution was allowed to stir overnight. The next day 1 N NaOH (25 mL) was added along with 75 mL of ether. The organic solution was then washed twice more with 25 mL portions of 1 N NaOH and two 25 mL portions of 1 N HCl. The organic layer was dried by first washing with saturated NaCl solution and then dried with either Na$_2$SO$_4$ or MgSO$_4$. The dried organic solution was concentrated yielding 500 mg (91%) of a light yellow solid. The solid was dissolved in 20 mL of THF and lithium aluminum hydride (182 mg 4.8 mmol) was added. The suspension was refluxed for 4 hours and then cooled to room temperature. The excess lithium aluminum hydride was quenched with a freshly made sat. solution Na$_2$SO$_4$. The addition of Na$_2$SO$_4$ caused a granular precipitate to form which was easily removed by filtration through a celite plug. The filtrate was concentrated yielding 476 mg (100%) of a clear oil. The amine was dissolved in ether (10 mL) and precipitated by adding 4 N HCl in dioxane (0.432 mL) diluted in 10 mL of ether. The off-white solid was recrystallized from methylene chloride/hexanes. IR (KBr HCl Salt): 2954, 2934, 2869, 2649 (br), 2474 (br, N—H), 1467; $^1$H NMR (CDCl$_3$, HCl Salt): δ 0.877 (t, J=7, 6H); 0.989–1.166 (m, 3H); 1.271 (p, J=8, 4H); 1.663–1.744 (m, 5H); 2.133–2.189 (m, 2H); 2.608–2.667 (m, 8H); 7.221–7.376 (m, 5H); 12.4 (br, m, 1H); $^{13}$C NMR (CDCl$_3$, 75.4, HCl Salt): δ 145.1 (C); 128.6 (CH); 126.3 (CH), 126.1 (CH); 54.1 (CH$_2$); 42.6 (CH$_3$); 42.2 (C); 36.2 (CH$_2$); 32.4 (CH$_2$); 25.5 (CH$_2$); 23.3 (CH$_2$); 14.1 (CH$_3$); EI-MS m/z (M$^+$HCl$^-$) calcd for C$_{19}$H$_{33}$N: 275.48 obsd 275.26. MALDI-TOF (M$^+$) calcd for C$_{19}$H$_{34}$N: 276.49, obsd 276.22.

Preparation of 4.83. The acid 4.33 (500 mg, 1.91 mmol) was dissolved in 5 mL of benzene in a round bottom flask. One drop of DMF was added as a catalyst and the solution was cooled with an ice bath. Once the solution had cooled the oxalyl chloride (0.831 mL, 9.53 mmol) was added dropwise resulting in a vigorously bubbling solution. The reaction was allowed to stir 3 hours and the volatiles were removed under vacuum. The residue was dissolved in dry ether (20 mL), cooled to 0° C., and N,N,2,2-tetramethyl-1,3-propanediamine (0.607 mL, 3.8 mmol) in ether (20 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either Na$_2$SO$_4$ or MgSO$_4$. The dried ether solution was concentrated yielding 783 mg (100%) of a light yellow oil. The oil was dissolved in 10 mL of ether and the amine was precipitated by adding 4 N HCl in dioxane (478 mL) diluted in 10 mL of ether. The off-white solid was recrystallized from methylene chloride/hexanes. IR (KBr HCl Salt): 3244 (N—H), 2786 (br), 1656 (C=O); $^1$H NMR (CDCl$_3$, HCl Salt): δ 0.873 (t, J=7 Hz, 6H); 0.923 (s, 6H); 0.962–1.345 (m, 8H); 1.720–1.910 (m, 4H); 2.447 (s, 2H); 2.656 (s, 2H); 2.748 (s, 2H); 3022 (d, J=6.5, 2H); 6.635 (t, J=6.5, 1H); 7.175–7.450 (m, 5H), 11.2 (br, m, 1H); $^{13}$C NMR (CDCl$_3$, 75.4 MHz, HCl Salt): δ 173.1 (C); 174.2 (C), 127.6 (CH); 126.1 (CH), 125.4 (CH); 45.8 (CH$_3$); 45.1 (CH$_2$); 42.5 (CH$_2$); 36.6 (CH$_2$); 25.1 (CH$_2$); 24.3 (CH$_3$); 22.7 (CH$_2$); 13.7 (CH$_3$); MALDI-TOF (M$^+$H$^+$) calcd for C$_{24}$H$_{49}$N$_2$O:376.63, obsd 376.34.

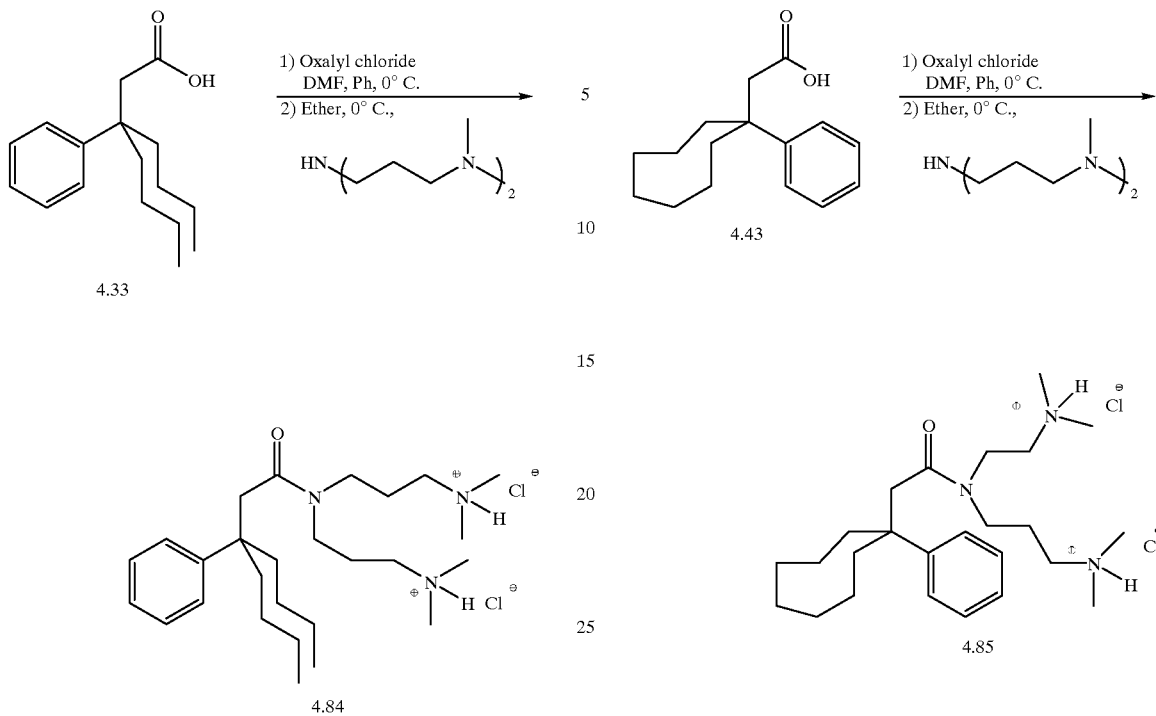

Preparation of 4.84. The acid 4.33 (1 g, 3.8 mmol) was dissolved in 5 mL of benzene in a round bottom flask. One drop of DMF was added as a catalyst and the solution was cooled with an ice bath. Once the solution had cooled, the oxalyl chloride (1.66 mL, 19.0 mmol) was added dropwise resulting in a vigorously bubbling solution. The reaction was allowed to stir 3 hours and the volatiles were removed under vacuum. The oil was dissolved in dry ether (25 mL), cooled to 0° C., and 3,3'-iminobis(N,N-dimethylpropylamine) (1.86 mL, 7.6 mmol) in ether (25 mL) was added dropwise resulting in a white precipitate. The solution was allowed to stir overnight. The next day 1 N NaOH (25 mL) was added and the precipitate dissolved. The layers were separated and the ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 1.54 g (94%) of a light yellow oil. The oil was dissolved in 15 mL of ether and the amine was precipitated by adding 4 N HCl in dioxane (0.950 mL) diluted in 15 mL of ether. The off-white solid was recrystallized from methylene chloride/hexanes. IR (Kbr HCl Salt): 3399 (N—H) (br), 2952, 2859, 2765, 2240 (N—H), 1635 (N—H), 1459; $^1$H NMR (CDCl$_3$, Free Amine): δ 0.868 (t, J=7, 6H); 1.046–1.186 (m, 4H); 1.291 (h, J=7, 4H); 1.488–1.570 (m, 4H); 2.133–2.189 (dp, J=5,6 4H); 2.103–2.216 (m, 16H); 2.916 (t, J=7, 2H); 3.191 (t, J=7, 2H); 7.150–7.340 (m, 5H); $^{13}$C NMR (CDCl$_3$, 75.4, HCl Salt): δ 170.6 (C); 146.7 (C); 127.7 (CH); 126.2 (CH); 125.3 (CH); 56.8 (CH$_2$); 56.2 (CH$_2$); 45.7 (CH$_2$); 45.2 (CH$_3$); 43.8 (CH$_2$); 43.2 (C); 40.7 (CH$_2$); 35.6 (CH$_2$); 26.9 (CH$_2$); 25.8 (CH$_2$); 25.6 (CH$_2$); 23.1 (CH$_2$); 13.9 (CH$_3$); MALDI-TOF (M$^+$) calcd for $C_{27}H_{51}N_3O$: 433.725, obsd 433.13.

Preparation of 4.85. The acid 4.43 (1 g, 4.1 mmol) was dissolved in 5 mL of benzene in a round bottom flask. One drop of DMF was added as a catalyst and the solution was cooled with an ice bath. Once the solution had cooled the oxalyl chloride (1.77 mL, 20 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (1.81 mL, 8 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 1.3 g (77%) of a light yellow oil. The oil was dissolved in 15 mL of ether and the amine was precipitated by adding 4 N HCl in dioxane (1.9 mL) diluted in 15 mL of ether. The off-white solid was recrystallized from methylene chloride/hexanes. IR (KBr HCl Salt): 3403 (N—H) (br), 2958, 2927, 2867, 2721 (N—H), 1625 (N—H), 1467; $^1$H NMR (CDCl$_3$, Free Amine): δ 1.449–1.488 (m, 10H); 1.839–1.890 (m, 4H); 2.136–2.195 (m, 4H); 2.535 (s, 2H); 2.764 (s, 6H); 2.848 (s, 6H); 2.803–3.001 (m, 8H); 3.315 (t, J=7, 2H); 5.00 (br, 2H); 7.176–7.392 (m, 5H); $^{13}$C NMR (CDCl$_3$, 75.4, HCl Salt): δ 172.4 (C); 146.1 (C); 127.9 (CH); 126.8 (CH), 125.3 (CH); 56.8 (CH$_2$); 56.2 (CH$_2$); 45.7 (CH$_2$); 43.8 (CH$_2$); 43.3 (CH$_2$); 43.2 (C); 42.9 (CH$_3$); 33.1 (CH$_2$); 28.3 (CH$_2$); 26.7 (CH$_2$); 24.8 (CH$_2$); 23.1 (CH$_2$); 22.6 (CH$_2$); MALDI-TOF (M$^+$) calcd for $C_{26}H_{47}N_3O$: 417.68, obsd 417.30.

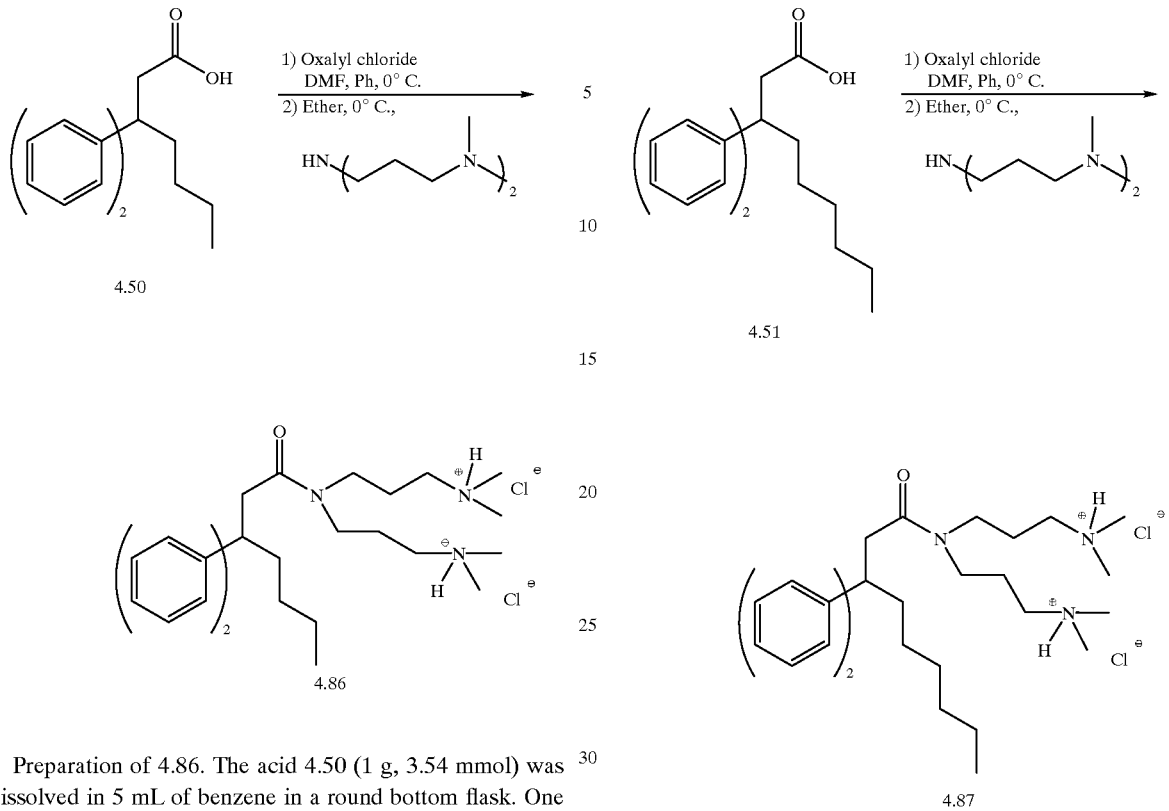

Preparation of 4.86. The acid 4.50 (1 g, 3.54 mmol) was dissolved in 5 mL of benzene in a round bottom flask. One drop of DMF was added as a catalyst and the solution was cooled with an ice bath. Once the solution had cooled the oxalyl chloride (1.54 mL, 17.7 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (1.54 ml, 7.1 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 1.45 g (94%) of a light yellow oil. The oil was dissolved in 15 mL of ether and the amine was precipitated by adding 4 N HCl in dioxane (1.77 mL) diluted in 15 mL of ether. The off-white solid was recrystallized from methylene chloride/hexanes. IR (KBr HCl Salt): 3364 (N—H) (br), 2955, 2931, 2860, 2732 (N—H), 1634 (C=O), 1467 $^1$H NMR (CDCl$_3$, HCl Salt): δ 0.804 (t, J=7, 6H); 0.976–1.101 (m, 2H); 1.21–1.306 (m, 2H); 1.744–1.814 (m, 2H); 2.369–2.422 (m, 2H); 2.710–2.863 (m, 24H); 3.34 (t, J=7, 2H); 7.173–7.298 (m, 5H); 11.49 (m, 1H); 11.81 (m, 1H); $^{13}$C NMR (CDCl$_3$, HCl Salt): δ 171.2 (C); 147.5 (C); 127.9 (CH); 127.6 (CH), 125.8 (CH); 55.5 (CH$_2$); 54.7 (CH$_2$); 49.6 (C); 42.9 (CH$_2$); 42.8 (CH$_3$); 38.9 (CH$_2$); 38.2 (CH$_2$); 24.0 (CH$_2$); 22.9 (CH$_2$); 13.9 (CH$_3$); MALDI-TOF (M$^+$) calcd for C$_{29}$H$_{47}$N$_3$O: 453.72, obsd 453.08.

Preparation of 4.87. The acid 4.51 (500 mg, 1.6 mmol) was dissolved in 5 mL of benzene in a round bottom flask. One drop of DMF was added as a catalyst and the solution was cooled with an ice bath. Once the solution had cooled the oxalyl chloride (717 mL, 8 mmol) was added dropwise resulting in a vigorously bubbling solution. The reaction was allowed to stir 3 hours and the volatiles were removed under vacuum. The oil was dissolved in dry ether (25 mL), cooled to 0° C., and 3,3'-iminobis(N,N-dimethylpropylamine) (0.717 mL, 7.1 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 651 mg (85%) of a light yellow oil. The oil was dissolved in 15 mL of ether and the amine was precipitated by adding 4 N HCl in dioxane (0.800 mL) diluted in 15 mL of ether. The off-white solid was recrystallized from methylene chloride/hexanes. IR (KBr HCl Salt): 3391 (N—H) (br), 2955, 2928, 2868, 2709 (N—H), 1627 (C=O); $^1$H NMR (CDCl$_3$, HCl Salt): δ 0.804 (t, J=7, 6H); 0.976–1.101 (m, 8H); 1.75–2.08 (m, 4H); 2.34–2.45 (m, 2H); 2.74 (s, 6H); 2.85 (s, 6H); 2.78–3.06 (m, 4H); 3.10 (s, 2H); 3.36 (m, 2H); 7.15–7.4 (m, 10H); 11.49 (m, 1H); 11.81 (m, 1H); $^{13}$C NMR (CDCl$_3$, 75.4, HCl Salt): δ 171.4 (C); 147.7 (C); 128.0 (CH); 127.8 (CH), 125.9 (CH); 55.3 (CH$_2$); 54.8 (CH$_2$); 49.7 (C); 45.3 (CH$_2$); 43.0 (CH$_2$); 42.9 (CH$_2$); 39.0 (CH$_2$); 38.7 (CH$_2$); 31.6 (CH$_2$); 29.8 (CH$_2$); 24.3 (CH$_2$); 24.1 (CH$_2$); 22.8 (CH$_2$); 22.5 (CH$_2$); 13.9 (CH$_3$); MALDI-TOF (M$^+$) calcd for C$_{29}$H$_{47}$N$_3$O: 481.39, obsd 481.18.

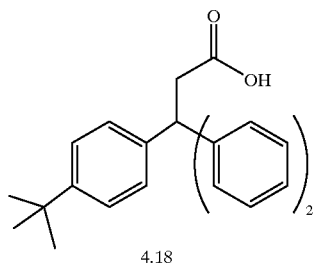
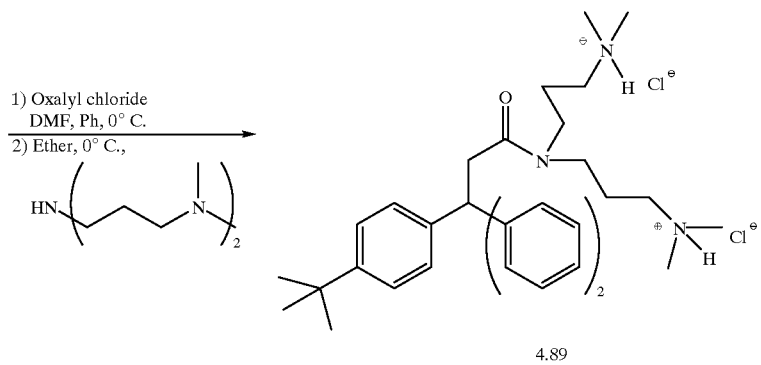

Preparation of 4.89. The acid 4.18 (1 g, 2.79 mmol) was dissolved in 5 mL of benzene in a round bottom flask. One drop of DMF was added as a catalyst and the solution was cooled with an ice bath. Once the solution had cooled the oxalyl chloride (1.22 mL, 13.9 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (1.24 mL, 5.6 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 1.0 g (68%) of a light yellow oil. The oil was dissolved in 15 mL of ether and the amine was precipitated by adding 4 N HCl in dioxane (1.40 mL) diluted in 15 mL of ether. The off-white solid was recrystallized from methylene chloride/hexanes. IR (KBr HCl Salt): 3399 (N—H) (br), 2962, 2705 (N—H), 2478, 2240 (N—H), 1634 (C=O), 1473; $^1$H NMR (CDCl$_3$, 300 Mhz HCl Salt): δ 1.30 (s, 9H); 1.821–1.901 (m, 2H); 2.05–2.13 (m, 2H); 2.72 (d, J=8 Hz, 2H); 2.78–2.88 (m, 2H); 2.85 (d, J=8 Hz, 24H); 3.04–3.12 (m, 2H); 3.20 (t, J=6.5, 2H); 3.35 (t, J=6.5, 2H); 3.69 (s, 2H); 7.13–7.33 (m, 14H); 11.58 (m, 1H); 11.95 (m, 1H); $^{13}$C NMR (CDCl$_3$, 75.4 MHz HCl Salt): δ 170.7 (C); 148.5 (C); 146.5 (C); 143.3 (C); 127.5 (CH), 125.8 (CH); 124.5 (CH); 55.9 (CH$_2$); 55.6 (C); 54.8 (CH$_2$); 45.7 (CH$_2$); 43.7 (CH$_2$); 42.9 (CH$_3$); 42.8 (CH$_3$); 42.2 (CH$_2$); 34.1 (C); 31.1 (CH$_3$); 24.2 (CH$_2$); 23.1 (CH$_2$); MALDI-TOF (M$^+$) calcd for $C_{35}H_{51}N_3O$: 529.47, obsd 529.19.

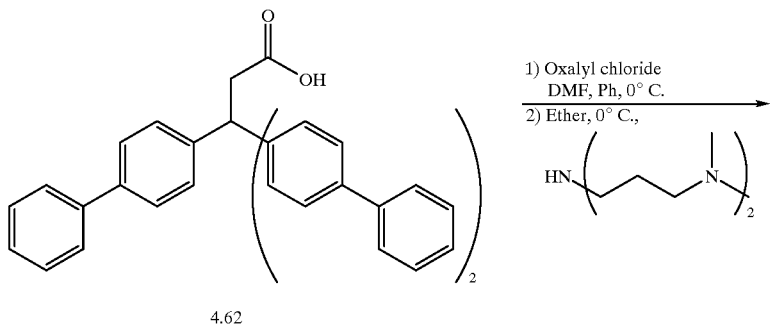

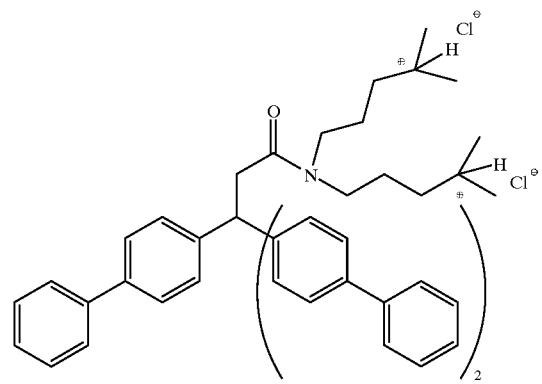

4.90

Preparation of 4.90. The acid 4.62 (1 g, 2.79 mmol) was dissolved in 5 mL of benzene in a round bottom flask. One drop of DMF was added as a catalyst and the solution was cooled with an ice bath. Once the solution had cooled the oxalyl chloride (1.22 mL, 13.9 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (1.24 mL, 5.6 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 1.0 g (68%) of a light yellow oil. The oil was dissolved in 15 mL of ether and the amine was precipitated by adding 4 N HCl in dioxane (1.40 mL) diluted in 15 mL of ether. The off-white solid was recrystallized from methylene chloride/hexanes. IR (KBr HCl Salt): 3399 (N—H) (br), 3027, 2966, 2711 (N—H), 2478, 1635 (C=O), 1484; $^1$H NMR ($CDCl_3$, 300 MHz HCl Salt): δ 1.74–1.85 (m, 2H); 2.10–2.23 (m, 2H); 2.52 (d, J=8 Hz, 2H); 2.65–2.73 (m, 2H); 2.83 (d, J=8 Hz, 24H); 3.04–3.14 (m, 2H); 3.29–3.4 (m, 4H); 3.69 (s, 2H); 7.25–7.63 (m, 27H); 11.58 (m, 1H); 11.95 (m, 1H); $^{13}$C NMR ($CDCl_3$, 75.4 MHz HCl Salt): δ 170.7 (C); 145.5 (C); 140.2 (C); 138.6 (C); 129.6 (CH); 128.7 (CH); 127.2 (CH); 126.7 (CH); 126.3 (CH); 55.8 ($CH_2$); 55.4 (C); 54.8 ($CH_2$); 44.6 ($CH_2$); 43.7 ($CH_2$); 42.9 ($CH_3$); 42.8 ($CH_2$); 24.2 ($CH_2$); 23.1 ($CH_2$); MALDI-TOF ($M^+$) calcd for $C_{49}H_{55}N_3O$: 701.99, obsd 701.95.

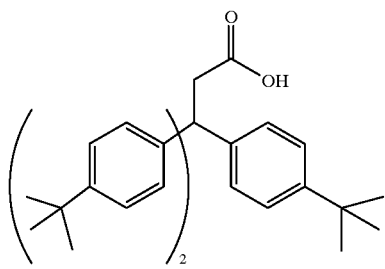

4.58

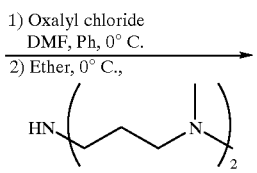

1) Oxalyl chloride
   DMF, Ph, 0° C.
2) Ether, 0° C.,

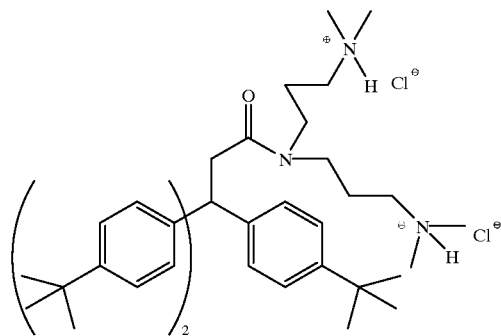

4.91

Preparation of 4.91. The acid 4.58 (890 mg, 1.89 mmol) was dissolved in 5 mL of benzene in a round bottom flask. One drop of DMF was added as a catalyst and the solution was cooled with an ice bath. Once the solution had cooled, oxalyl chloride (0.825 mL, 9.45 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (8.41 mL, 3.78 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 931 mg (77%) of a light yellow oil. The oil was dissolved in 15 mL of ether and the amine was precipitated by adding 4 N HCl in dioxane (0.945 mL) diluted in 15 mL of ether. The off-white solid was recrystallized from methylene chloride/hexanes. IR (Kbr HCl Salt): 3442 (N—H) (br), 2957, 2928, 2857, 1635 (C=O), 1456; $^1$H NMR (CDCl$_3$, 300 MHz HCl Salt): δ 1.25 (s, 27H); 1.72–1.89 (m, 4H); 2.57 (s, 6H); 2.62 (s, 6H); 2.66–2.78 (m, 4H); 3.05–3.14 (m, 2H); 3.29–3.4 (m, 4H); 3.67 (s, 2H); 7.14–7.33 (m, 12H); $^{13}$C NMR (CDCl$_3$, 75.4 MHz HCl Salt): δ 171.2 (C); 148.3 (C); 143.7 (C); 128.6 (CH), 125.2 (CH); 55.7 (CH$_2$); 55.2 (C); 54.8 (CH$_2$); 46.2 (CH$_2$); 43.7 (CH$_2$); 43.1 (CH$_3$); 42.8 (CH$_2$); 34.1 (C); 31.2 (Ch$_2$); 29.4 (Ch$_2$); 25.1 (CH$_2$); 23.1 (CH$_2$); MALDI-TOF (M$^+$H$^+$) calcd for $C_{43}H_{68}N_3O$: 643.037, obsd 643.17.

drop of DMF was added as a catalyst and the solution was cooled with an ice bath. Once the solution had cooled the oxalyl chloride (1.61 mL, 18.5 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (1.65 mL, 7.4 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 1.622 g (100%) of a light yellow solution. The oil was dissolved in 15 mL of ether and the amine was precipitated by adding 4 N HCl in dioxane (1.85 mL) diluted in 15 mL of ether. The off-white solid was recrystallized from methylene chloride/hexanes. IR (KBr HCl Salt): 3430 (N—H) (br), 2957, 2928, 2869, 2697 (N—H), 1635 (C=O), 1456; $^1$H NMR (CDCl$_3$, 300 MHz HCl Salt): δ 0.869–0.925 (m, 9H); 1.28–1.395 (m, 20H); 2.105–2.213 (m, 6H); 2.856 (s, 6H); 2.929 (s, 6H); 3.092 (t, J=7 Hz, 2H); 3.195 (t, J=7, 2H); 3.55 (m, 4H); $^{13}$C NMR (CDCl$_3$, 75.4 MHz HCl Salt): δ 172.1 (C); 55.8 (CH$_2$); 54.9 (CH$_2$); 46.1 (CH$_2$); 43.5 (CH$_3$); 43.0 (CH$_3$); 42.8 (CH$_2$); 38.4 (C); 37.6 (CH$_2$); 36.3 (CH$_2$); 31.6 (CH$_2$); 29.9 (CH$_2$); 25.4 (CH$_2$); 24.3 (CH$_2$); 23.3 (CH$_2$); 22.5 (CH$_2$); 14.0 (CH$_3$); MALDI-TOF (M$^+$H$^+$) calcd for $C_{27}H_{59}N_3O$: 441.79, obsd 441.18.

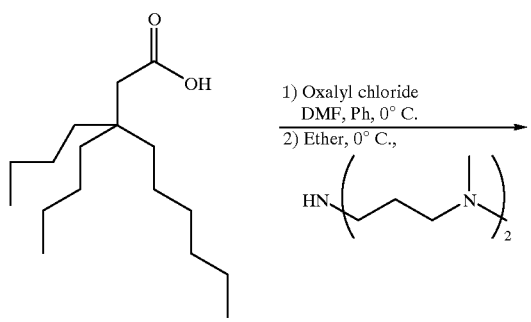

4.36

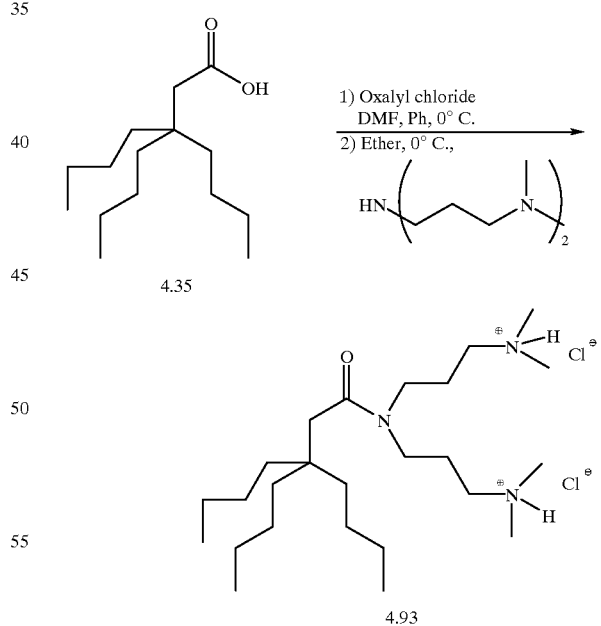

4.35

4.93

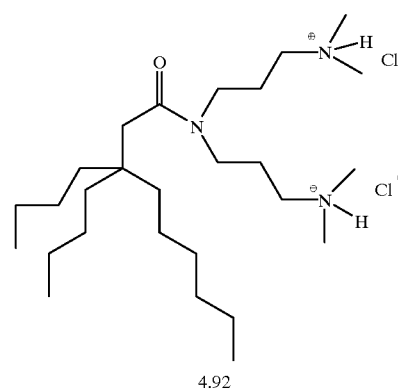

4.92

Preparation of 4.92. The acid 4.36 (1 g, 3.7 mmol) was dissolved in 5 mL of benzene in a round bottom flask. One Preparation of 4.93. The acid 4.35 (1 g, 4.1 mmol) was dissolved in 5 mL of benzene in a round bottom flask. One drop of DMF was added as a catalyst and the solution was cooled with an ice bath. Once the solution had cooled the oxalyl chloride (1.8 mL, 21 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (1.84 mL, 8.2 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 1.7 g (100%) of a light yellow oil. The oil was dissolved in 15 mL of ether and the amine was precipitated by adding 4 N HCl in dioxane (2 mL) diluted in 15 mL of ether. The off-white solid was recrystallized from methylene chloride/hexanes. IR (KBr HCl Salt): 3399 (N—H) (br), 2954, 2929, 2861, 2707 (N—H), 1627 (C=O), 1467; $^1$H NMR (CDCl$_3$, 300 MHz HCl Salt): δ 0.900 (t, J=7, 9H); 1.055–1.42 (m, 16H); 2.08–2.27 (s, 6H); 2.85 (d, J=4.5, 6H); 2.96 (t, J=4.5, 6H); 3.08 (q, J=7, 2H); 3.18–3.22 (m, 2H); 3.57 (t, J=6, 4H); 11.92 (m, 1H); 12.15 (m, 1H); $^{13}$C NMR (CDCl$_3$, 75.4 MHz HCl Salt): δ 172.2 (C); 55.9 (CH$_2$); 55.0 (CH$_2$); 46.1 (CH$_2$); 43.6 (CH$_2$); 43.0 (CH$_3$); 42.9 (CH$_3$); 38.5 (C); 37.6 (CH$_2$); 36.5 (CH$_2$); 25.6 (CH$_2$); 24.4 (CH$_2$); 23.4 (CH$_2$); 14.1 (CH$_3$); MALDI-TOF (M$^+$H$^+$) calcd for $C_{25}H_{55}N_3O$: 413.73, obsd 413.36.

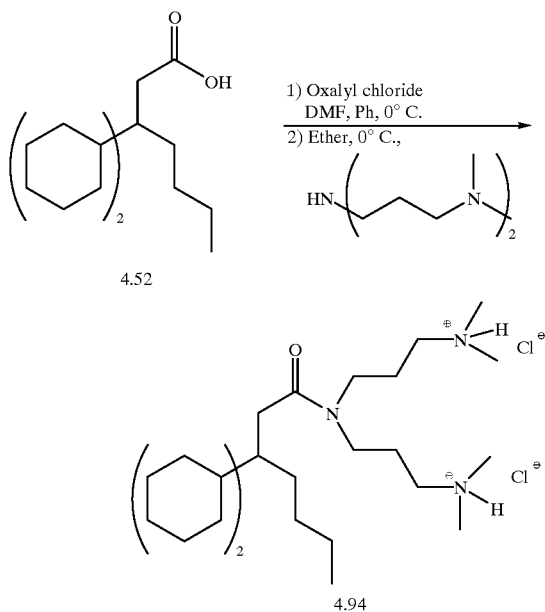

4.52

4.94

Preparation of 4.94. The acid 4.52 (1 g, 3.4 mmol) was dissolved in 5 mL of benzene in a round bottom flask. One drop of DMF was added as a catalyst and the solution was cooled with an ice bath. Once the solution had cooled the oxalyl chloride (1.48 mL, 17 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (1.51 mL, 8.2 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 1.26 g (80%) of a light yellow oil. The oil was dissolved in 15 mL of ether and the amine was precipitated by adding 4 N HCl in dioxane (1.7 mL) diluted in 15 mL of ether. The off-white solid was recrystallized from methylene chloride/hexanes. IR (KBr HCl Salt): 3399 (N—H) (br), 2928, 2850, 2709 (N—H), 1625 (C=O), 1467; $^1$H NMR (CDCl$_3$, 300 MHz HCl Salt): δ 0.904 (t, J=7, 3H); 1.027–1.26 (m, 16H); 1.499–1.80 (m, 16H); 2.11–2.27 (m, 6H); 2.84 (d, J=5, 6H); 2.939 (d, J=5, 6H); 3.08 (q, J=6, 2H); 3.18–3.22 (m, 2H); 3.59 (p, J=7, 4H); 11.9 (m, 1H); 12.1 (m, 1H); $^{13}$C NMR (CDCl$_3$, 75.4 MHz HCl Salt): δ 173.2 (C); 55.9 (CH$_2$); 54.9 (CH$_2$); 46.2 (CH$_2$); 44.1 (CH$_2$); 43.7 (C); 43.5 (CH$_3$); 43.0 (CH$_3$); 42.9 (CH$_3$); 35.9 (CH$_2$); 34.6 (CH$_2$); 28.9 (CH$_2$); 27.6 (CH$_2$); 27.5 (CH$_2$); 27.0 (CH$_2$); 26.7 (CH$_2$); 24.3 (CH$_2$); 23.8 (CH$_2$); 23.2 (CH$_2$); 14.1 (CH$_3$); EI-MS m/z (M$^+$): calcd for $C_{29}H_{57}N_3O$: 463.4501, obsd 463.4506 MALDI-TOF (M$^+$) calcd for $C_{29}H_{57}N_3O$ 463.45, obsd 463.29.

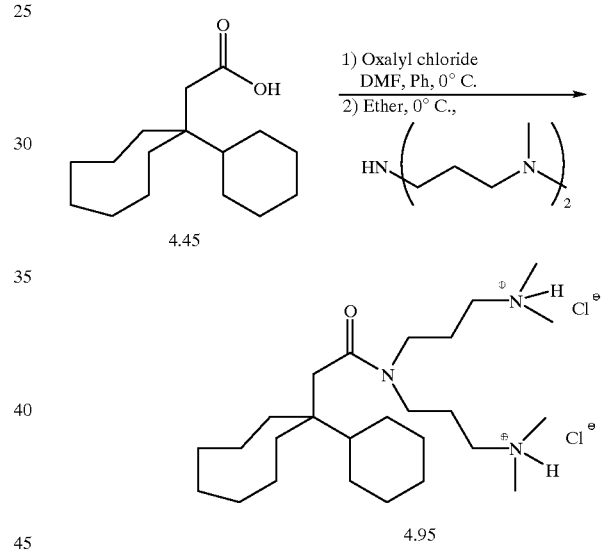

4.45

4.95

Preparation of 4.95. The acid 4.45 (500 mg, 2 mmol) was dissolved in 5 mL of benzene in a round bottom flask. One drop of DMF was added as a catalyst and the solution was cooled with an ice bath. Once the solution had cooled, oxalyl chloride (0.864 mL, 10 mmol) was added dropwise resulting in a vigorously bubbling solution. The reaction was allowed to stir 3 hours and the volatiles were removed under vacuum. The residue was dissolved in dry ether (25 mL), cooled to 0° C., and 3,3'-iminobis(N,N-dimethylpropylamine) (0.888 mL, 4 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 833 mg (100%) of a light yellow oil. The oil was dissolved in 15 mL of ether and the amine was precipitated by adding 4 N HCl in dioxane (1 mL) diluted in 15 mL of ether. The off-white solid was recrystallized from methylene chloride/hexanes. IR (KBr HCl Salt): 3399 (N—H) (br), 2923, 2850, 2692 (N—H), 1623 (C=O), 1473; $^1$H NMR (CDCl$_3$, 300 MHz HCl Salt): δ 0.895–2.011 (m, 21H); 1.027–1.26 (m, 16H); 1.499–1.80 (m, 16H); 2.11–2.27 (m, 6H); 2.84 (d, J=5, 6H); 2.15 (s, 2H) 2.16–2.35 (m, 4H); 2.84 (d, J=8, 6H); 2.94 (d, J=8, 6H); 3.005–3.201 (m, 4H); 3.62 (m, 4H); 12.15 (m, 1H); 12.28 (m, 1H); $^{13}$C NMR (CDCl$_3$, 75.4 MHz HCl Salt): δ 173.2 (C); 55.9 (CH$_2$); 54.9 (CH$_2$); 46.2 (CH$_2$); 44.1 (CH$_2$); 43.7 (C); 43.5 (CH$_3$); 43.0 (CH$_3$); 42.9 (CH$_3$); 35.9 (CH$_2$); 34.6 (CH$_2$); 28.9 (CH$_2$); 27.6 (CH$_2$); 27.5 (CH$_2$); 27.0 (CH$_2$); 26.7 (CH$_2$); 24.3 (CH$_2$); 23.8 (CH$_2$); 23.2 (CH$_2$); 14.1 (CH$_3$); MALDI-TOF (M$^+$) calcd for C$_{26}$H$_{51}$N$_3$O: 421.98, obsd 421.93.

N HCl in dioxane (0.550 mL) diluted in 15 mL of ether. The off-white solid was recrystallized from methylene chloride/hexanes. IR (KBr Free Amine): 3442, 3405 (br, N—H), 2927, 2858, 2672 (br, N—H), 1635 (C=O), 1469; $^1$H NMR (CDCl$_3$, 300 MHz HCl Salt): δ 0.897 (t, J=7, 6H); 0.980–1.783 (m, 9H); 2.117–2.252 (m, 4H); 2.843 (s, 6H); 2.927 (s, 6H); 3.072 (t, J=7, 2H); 3.16–3.212 (m, 2H); 3.577 (q, J=7.5, 2H); $^{13}$C NMR (CDCl$_3$, 75.4 MHz HCl Salt): δ 172.9 (C); 56.0 (CH$_2$); 55.1 (CH$_2$); 46.5 (CH$_2$); 44.9 (CH); 43.8 (CH$_2$); 43.1 (CH$_3$); 43.0 (CH$_3$); 41.2 (C); 36.4 (CH$_2$); 35.7 (CH$_2$); 27.7 (CH$_2$); 26.7 (CH$_2$); 26.3 (CH$_2$); 24.5 (CH$_2$); 23.6 (CH$_2$); 23.4 (CH$_2$); 14.1 (CH$_3$); MALDI-TOF (M$^+$) calcd for C$_{27}$H$_{57}$N$_3$O: 439.773, obsd 439.347.

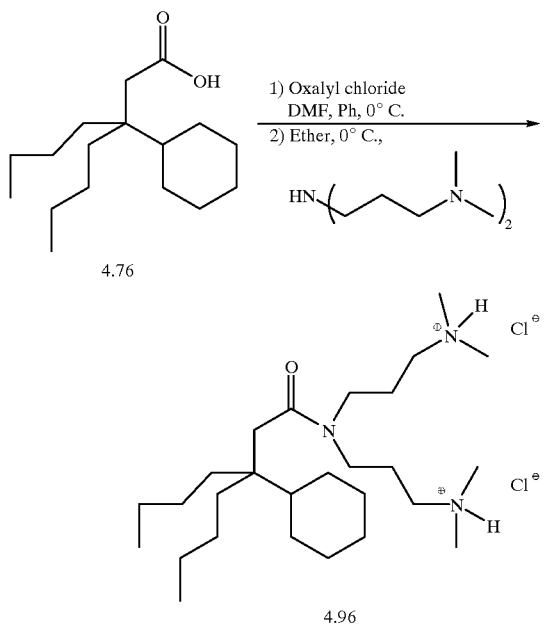

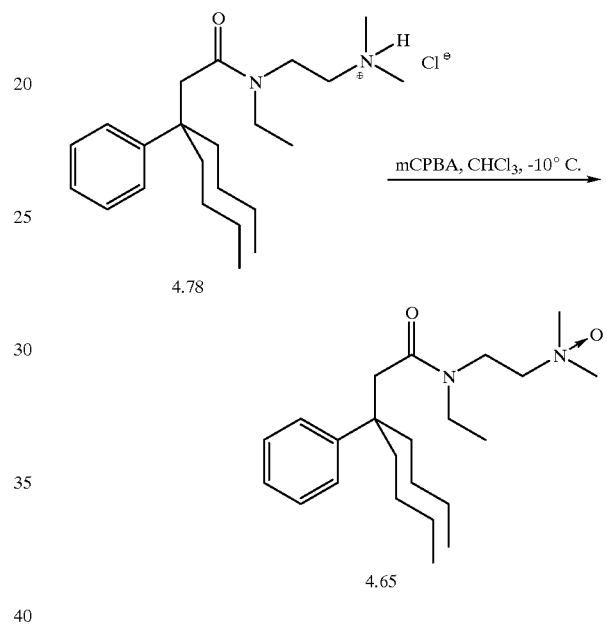

Preparation of 4.96. The acid 4.76 (300 mg, 1.1 mmol) was dissolved in 5 mL of benzene in a round bottom flask. One drop of DMF was added as a catalyst and the solution was cooled with an ice bath. Once the solution had cooled, oxalyl chloride (0.487 mL, 5.5 mmol) was added dropwise resulting in a vigorously bubbling solution. The reaction was allowed to stir 3 hours and the volatiles were removed under vacuum. The oil was dissolved in dry ether (25 mL), cooled to 0° C., and 3,3'-iminobis(N,N-dimethlylpropylamine) (0.498 mL, 2.2 mmol) in ether (25 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either Na$_2$SO$_4$ or MgSO$_4$. The dried ether solution was concentrated yielding 490 mg (100%) of a light yellow solution. The oil was dissolved in 15 mL of ether and the amine was precipitated by adding 4

Preparation of 4.65. The hydrochloride salt 4.78 (3.43 g, 8.69 mmol) was dissolved in 1 N NaOH causing a white precipitate to form. The free amine was extracted with chloroform (20 mL) three times. The organic layers were combined, dried with MgSO$_4$, and concentrated to a light yellow oil. The oil was dissolved in chloroform (5 mL), cooled to -10° C., and mCPBA (6 g, 34.8 mmol) was added as a solid. The reaction was allowed to stir for 3 hours and then poured onto an alumina column pre-equilibrated with chloroform. The column was eluted first with chloroform (1 bed volume) to remove impurities and then with 10% methanol in chloroform (enough to remove all of the product). The fractions containing product were combined and concentrated. The resulting oil which contained some alumina was dissolved in water which formed a milky solution. Upon filtration through 0.22 mm syringe filter the solution clarified to a colorless solution which was lyophilized. The material was first isolated as an oil. The oil upon sitting formed 2.45 g (75%) of waxy yellow crystals. IR (KBr): 3377, 2955, 2930, 2870 (br, N—H), 1634 (C=O), 1456; $^1$H NMR (CDCl$_3$, 300 MHz): δ 0.897 (t, J=7, 6H); 1.08 (t, J=7, 3H); 1.08–1.398 (m, 4H); 1.580–2.05 (m, 4H);

2.55 (s, 2H); 3.002–3.105 (m, 10H); 3.65–3.72 (m, 2H); 7.102–7.34 (m, 5H); $^{13}$C NMR (MeOH, 75.4 MHz): δ 171.9 (C); 146.0 (C); 127.7 (CH); 126.0 (CH); 125.5 (CH); 65.9 (CH$_2$); 59.1 (CH$_3$); 43.1 (C); 42.9 (CH$_2$); 40.5 (CH$_2$); 36.0 (CH$_3$); 25.7 (CH$_2$); 22.9 (CH$_2$); 13.5 (CH$_3$); 13.4 (CH$_3$); FAB-MS m/z (M$^+$H$^+$) calcd for C$_{23}$H$_{41}$N$_2$O$_2$: 377.6, obsc 377.3.

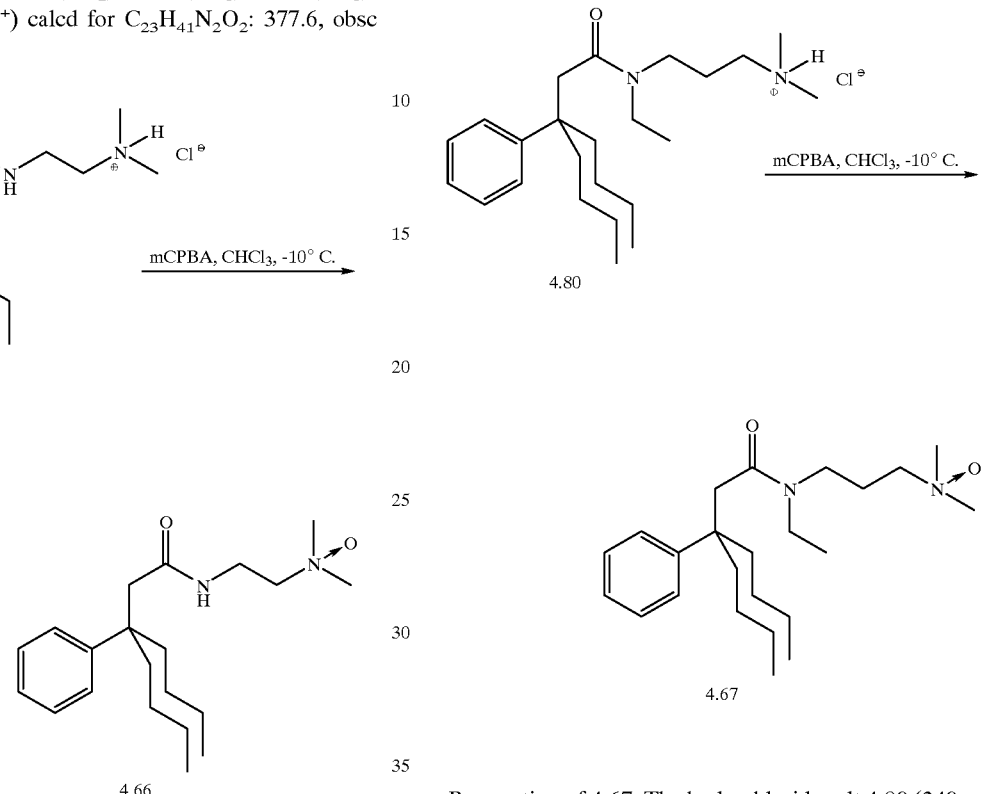

Preparation of 4.66. The hydrochloride salt 4.79 (6.15 g, 16.9 mmol) was dissolved in 1 N NaOH causing a white precipitate to form. The free amine was extracted with chloroform (20 mL) three times. The organic layers were combined, dried with MgSO$_4$, and concentrated to a light yellow oil. The oil was dissolved in chloroform (5 mL), cooled to –10° C., and mCPBA (14.6 g, 84.5 mmol) was added as a solid. The reaction was allowed to stir for 3 hours and then poured onto an alumina column pre-equilibrated with chloroform. The column was eluted first with chloroform (1 bed volume) to remove impurities and then with 10% methanol in chloroform (enough to remove all of the product). The fractions containing product were combined and concentrated. The resulting oil which contained some alumina was dissolved in water which formed a milky solution. Upon filtration through 0.22 mm syringe filter the solution clarified to a colorless solution which was lyophilized. The material was first isolated as an oil. The oil upon sitting formed 5.0 g (85%) of a waxy solid which could be suspended in dry ether to form crystalline plates. IR (KBr): 3309, 3076, 2927, 2861, 1634 (C=O), 1549, 1456; $^1$H NMR (CDCl$_3$, 300 MHz): δ 0.860 (t, J=7, 6H); 1.08–1.398 (m, 8H); 1.750–1.91 (m, 6H); 2.48 (s, 2H); 3.082–3.185 (m, 10H); 6.55 (t, J=4, 1H); 7.102–7.34 (m, 5H); $^{13}$C NMR (MeOH, 75.4 MHz): d 171.1 (C); 146.5 (C); 127.8 (CH); 126.1 (CH); 125.3 (CH); 68.1 (CH$_2$); 58.5 (CH$_3$); 45.5 (CH$_2$); 42.8 (C); 36.4 (CH$_2$); 25.4 (CH$_2$); 23.1 (CH$_2$); 22.9 (CH$_2$); 13.7 (CH$_3$); 13.4 (CH$_3$); FAB-MS m/z 363.3 (M$^+$H$^+$).

Preparation of 4.67. The hydrochloride salt 4.80 (340 mg, 0.796 mmol) was dissolved in 1 N NaOH causing a white precipitate to form. The free amine was extracted with chloroform (20 mL) three times. The organic layers were combined, dried with MgSO$_4$, and concentrated to a light yellow oil. The oil was dissolved in chloroform (10 mL), cooled to –10° C., and mCPBA (687 mg, 3.98 mmol) was added as a solid. The reaction was allowed to stir for 3 hours and then poured onto an alumina column pre-equilibrated with chloroform. The column was eluted first with chloroform (1 bed volume) to remove impurities and then with 10% methanol in chloroform (enough to remove all of the product). The fractions containing product were combined and concentrated. The resulting oil which contained some alumina was dissolved in water which formed a milky solution. Upon filtration through 0.22 mm syringe filter the solution clarified to a clear colorless solution which was lyophilized. The material was isolated as 297 mg (95%) of a clear yellow oil. IR (KBr): 3382, 2953, 2870, 1634 (C=O); $^1$H NMR (CDCl$_3$, 300 MHz): δ 0.882 (t, J=7, 6H); 1.052–1.3428 (m, 6 H); 1.834–2.003 (m, 6H); 2.592 (s, 2H); 2.663 (s, 3H); 3.085–3.307 (m, 10); 7.168–7.34 (m, 5H); $^{13}$C NMR (MeOH, 75.4 MHz): δ 171.3 (C); 146.5 (C); 127.8 (CH); 126.2 (CH); 125.5 (CH); 67.9 (CH$_2$); 58.1 (CH$_3$); 44.5 (CH$_2$); 42.9 (C); 41.1 (CH$_2$); 36.2 (CH$_2$); 35.6 (CH$_3$); 25.7 (CH$_2$); 23.1 (CH$_2$); 21.2 (CH$_2$); 13.9 (CH$_3$); FAB-MS m/z (M$^+$H$^+$) calcd for C$_{23}$H$_{41}$N$_2$O$_2$ 377.5, obsd 377.3.

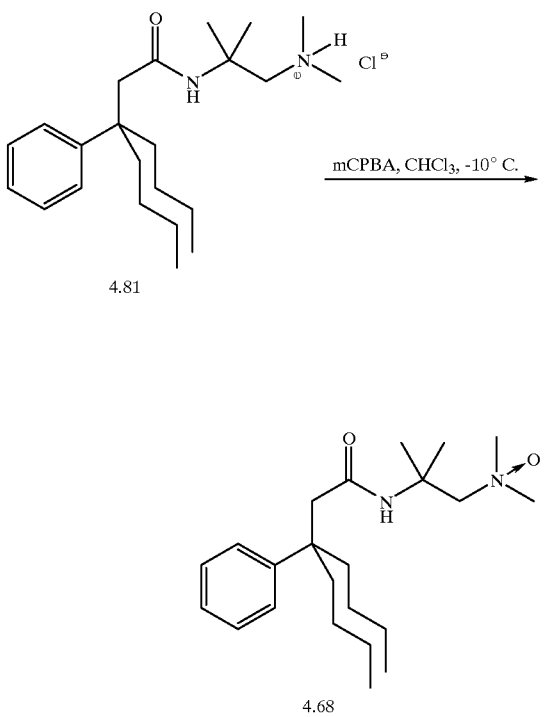

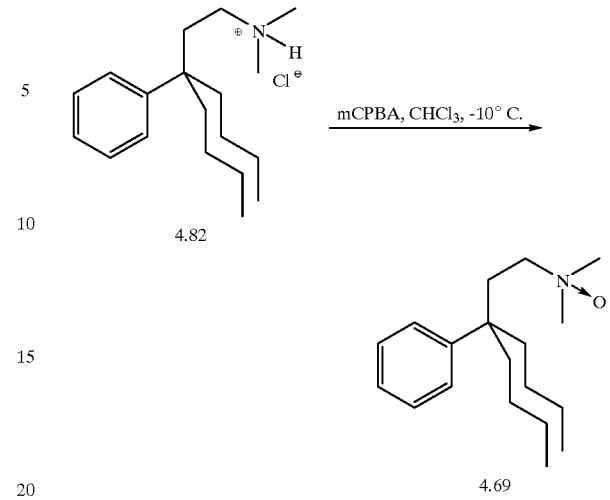

Preparation of 4.68. The hydrochloride salt 4.81 (630 mg, 1.7 mmol) was dissolved in 1 N NaOH causing a white precipitate to form. The free amine was extracted with chloroform (20 mL) three times. The organic layers were combined, dried with MgSO$_4$, and concentrated to a light yellow oil. The oil was dissolved in chloroform (10 mL), cooled to −10° C., and mCPBA (1.58 g, 8.5 mmol) was added as a solid. The reaction was allowed to stir for 3 hours and then poured onto an alumina column pre-equilibrated with chloroform. The column was eluted first with chloroform (1 bed volume) to remove impurities and then with 10% methanol in chloroform (enough to remove all of the product). The fractions containing product were combined and concentrated. The resulting oil which contained some alumina was dissolved in water which formed a milky solution. Upon filtration through 0.22 mm syringe filter the solution clarified to a clear colorless solution which was lyophilized. The material was isolated as 605 mg (92%) of a clear yellow oil. IR (KBr): 2954, 2930, 2860, 1662 (C=O), 1539, 1445, 1373; $^1$H NMR (CDCl$_3$, 300 MHz): δ 0.865 (t, J=7, 6H); 1.088–1.335 (m, 8H); 1.357 (s, 6H); 1.813–1.905 (m, 4H); 2.431 (s, 2H); 3.13 (s, 6); 3.144 (s, 2H); 7.14–7.39 (m, 5H); 9.866 (br. s, 1H); $^{13}$C NMR (MeOH, 75.4 MHz): δ 170.9 (C); 146.7 (C); 127.9 (CH); 126.7 (CH); 125.3 (CH); 75.8 (CH$_2$); 60.8 (CH$_3$); 53.2 (C); 46.7 (CH$_2$); 43.3 (C); 36.8 (CH$_2$); 26.9 (CH$_3$); 25.7 (CH$_2$); 23.4 (CH$_2$); 14.1 (CH$_3$); FAB-MS m/z (M$^+$H$^+$) calcd for C$_{23}$H$_{41}$N$_2$O$_2$ 377.5, obsd 377.3; calcd for C$_{23}$H$_{40}$N$_2$O$_2$Na 399.4, obsd 399.3 (M$^+$Na$^+$).

Preparation of 4.69. The hydrochloride salt 4.82 (598 mg, 1.92 mmol) was dissolved in 1 N NaOH causing a white precipitate to form. The free amine was extracted with chloroform (20 mL) three times. The organic layers were combined, dried with MgSO$_4$, and concentrated to a light yellow oil. The oil was dissolved in chloroform (10 mL), cooled to −10° C., and m mCPBA (398 mg, 2.3 mmol) was added as a solid. The reaction was allowed to stir for 3 hours and then poured onto an alumina column pre-equilibrated with chloroform. The column was eluted first with chloroform (1 bed volume) to remove impurities and then with 10% methanol in chloroform (enough to remove all of the product). The fractions containing product were combined and concentrated. The resulting oil which contained some alumina was dissolved in water which formed a milky solution. Upon filtration through 0.22 mm syringe filter the solution clarified to a colorless solution which was lyophilized. The material was isolated as 397 mg (71%) of a clear yellow oil. IR (KBr): 3316, 2957, 2929, 2865, 1467; $^1$H NMR (CDCl$_3$, 300 MHz): δ 0.870 (t, J=7, 6H); 1.008–1.319 (m, 8H); 1.624–1.718 (m, 4H); 2.141–2.197 (m, 2H); 2.932–2.988 (m, 2H); 3.072 (s, 6H); 7.184–7.34 (m, 5H); $^{13}$C NMR (MeOH, 75.4 MHz): δ 145.7 (C); 128.1 (CH); 125.9 (CH); 125.8 (CH); 67.6 (CH$_2$); 58.1 (CH$_3$); 41.9 (C); 36.3 (CH$_2$); 32.3 (CH$_2$); 25.2 (CH$_2$); 23.0 (CH$_2$); 13.8 (CH$_3$); FAB-MS m/z 292.3 (M$^+$H$^+$) calcd for C$_{19}$H$_{34}$NO 292.5, obsd 292.3 (2M$^+$) 583.6.

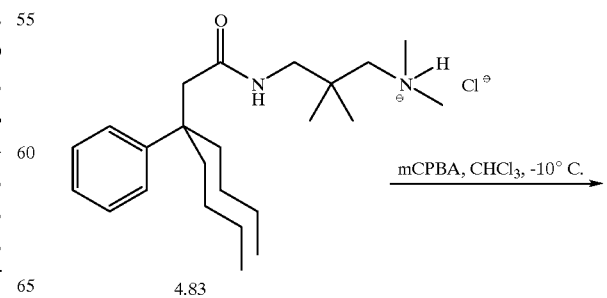

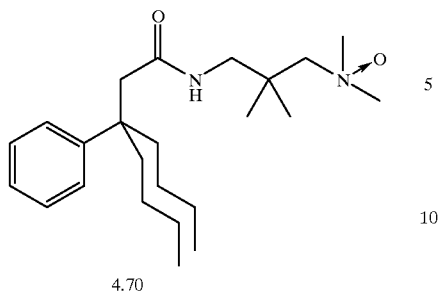

4.70

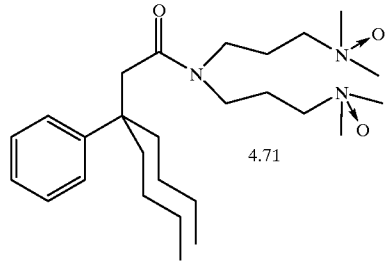

4.71

Preparation of 4.70. The hydrochloride salt 4.83 (517 mg, 1.26 mmol) was dissolved in 1 N NaOH causing a white precipitate to form. The free amine was extracted with chloroform (20 mL) three times. The organic layers were combined, dried with $MgSO_4$, and concentrated to a light yellow oil. The oil was dissolved in chloroform (10 mL), cooled to $-10°$ C., and mCPBA (260 mg, 1.5 mmol) was added as a solid. The reaction was allowed to stir for 3 hours and then poured onto an alumina column pre-equilibrated with chloroform. The column was eluted first with chloroform (1 bed volume) to remove impurities and then with 10% methanol in chloroform (enough to remove all of the product). The fractions containing product were combined and concentrated. The resulting oil which contained some alumina was dissolved in water which formed a milky solution. Upon filtration through 0.22 mm syringe filter the solution clarified to a colorless solution which was lyophilized. The material was isolated as 471 mg (87%) of a white solid. IR (KBr): 3345 (br), 2955, 2930, 2870, 1648 (C=O); $^1$H NMR (CDCl$_3$, 300 MHz): δ 0.869 (t, J=7, 6H); 1.017–1.340 (m, 8H); 1.771–1.970(m, 4H); 2.514 (s, 2H); 2.889 (s, 2H); 3.164 (s, 6H); 3.246 (d, J=6, 2H); 7.127 (t, J=7, $^1$H); 7.258–7.389 (m, 4H); 8.57 (t, J=6, 1H); $^{13}$C NMR (MeOH, 75.4 MHz) δ 170.8 (C); 146.9 (C); 127.7 (CH); 126.6 (CH); 125.0 (CH); 78.4 (CH$_2$); 61.3 (CH$_3$); 46.3 (CH$_2$); 45.3 (CH$_2$); 43.0 (C); 36.9 (CH$_2$); 36.5 (C); 26.7 (CH$_3$); 25.6 (CH$_2$); 23.1 (CH$_2$); 13.9 (CH$_3$); FAB-MS m/z (M$^+$H$^+$) calcd for $C_{24}H_{43}N_2O_2$ 391.6, obsd 391.4; (M$^+$Na$^+$) calcd for $C_{24}H_{42}N_2O_2Na$ 413.6, obsd 413.4.

Preparation of 4.71. The hydrochloride salt 4.84 (1.93, 4.28 mmol) was dissolved in 1 N NaOH causing a white precipitate to form. The free amine was extracted with chloroform (20 mL) three times. The organic layers were combined, dried with $MgSO_4$, and concentrated to a light yellow oil. The oil was dissolved in chloroform (10 mL), cooled to $-10°$ C., and mCPBA (1.1 g, 12.8 mmol) was added as a solid. The reaction was allowed to stir for 3 hours and then poured onto an alumina column pre-equilibrated with chloroform. The column was eluted first with chloroform (1 bed volume) to remove impurities and then with 30% methanol in chloroform (enough to remove all of the product). The fractions containing product were combined and concentrated. A large group of the column fractions contained both product and presumably m-chlorobenzoic acid. The 30% methanol elutes a large portion of both materials. Attempts to run columns on bis-N-oxides using less than 30% methanol would not elute the bis-N-oxides. The mCPBA oxidation does not provide bis-N-oxides in good yields; therefore it is preferred that the hydrogen peroxide method be used for bis-N-oxides. The resulting oil which contained some alumina was dissolved in water which formed a milky solution. Upon filtration through 0.22 mm syringe filter the solution clarified to a colorless solution which was lyophilized. The material was isolated as 922 mg (50%) of a clear yellow oil. IR (KBr): 3396 (br), 2954, 2871,1622 (C=O), 1466; $^1$H NMR (CDCl$_3$, 300 MHz): δ 0.889 (t, J=7, 6H); 1.007–1.380 (m, 8H); 1.771–2.09 (m, 4H); 2.2 (s, 2H); 3.001–3.39 (m, 6H); 3.09 (s, 6H); 3.164 (s, 6H); 7.147 (t, J=7, $^1$H); 7.258–7.389 (m, 4H); $^{13}$C NMR (CDCl$_3$, 75.4 MHz): d 171.0 (C); 146.9 (C); 127.8 (CH); 126.2 (CH); 125.5 (CH); 67.9 (CH$_2$); 67.5 (CH$_2$); 58.6 (CH$_3$); 58.4 (CH$_3$); 46.3 (CH$_2$); 43.1 (CH$_2$); 43.0 (C); 40.9 (CH$_2$); 36.0 (CH$_2$); 25.6 (CH$_2$); 23.1 (CH$_2$); 21.8 (CH$_2$); 13.9 (CH$_3$); FAB-MS m/z 463.7 (M$^+$H$^+$).

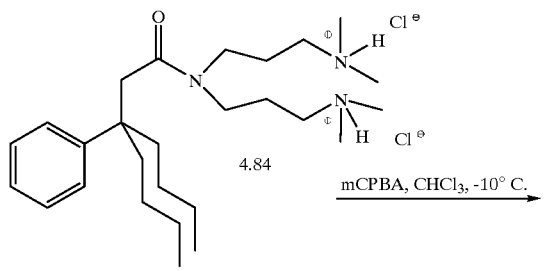

4.84 mCPBA, CHCl$_3$, -10° C.

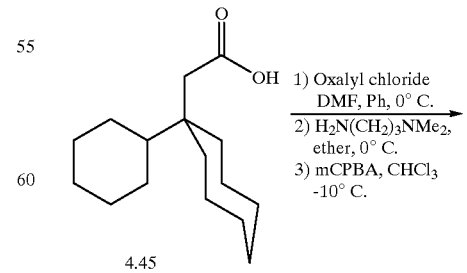

4.45

1) Oxalyl chloride
   DMF, Ph, 0° C.
2) H$_2$N(CH$_2$)$_3$NMe$_2$,
   ether, 0° C.
3) mCPBA, CHCl$_3$
   -10° C.

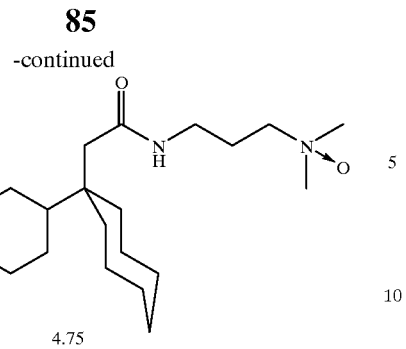

4.75

Preparation of 4.75. The acid 4.45 (143 mg, 0.56 mmol) was dissolved in 5 mL of benzene in a round bottom flask. One drop of DMF was added as a catalyst and the solution was cooled with an ice bath. Once the solution had cooled the oxalyl chloride (0.247 mL, 2.8 mmol) was added dropwise resulting in a vigorously bubbling solution. The reaction was allowed to stir 3 hours and the volatiles were removed under vacuum. The oil was dissolved in dry ether (10 mL), cooled to 0° C., and N,N-dimethylethylenediamine (0.142 mL, 1.12 mmol) in ether (10 mL) was added dropwise resulting in a white precipitate. The solution was allowed to stir overnight. The next day 1 N NaOH (15 mL) was added and the precipitate dissolved. The ether solution was then washed twice more with 15 mL portions of 1 N NaOH. The ether layer was dried by first washing with saturated NaCl solution and then dried with either $Na_2SO_4$ or $MgSO_4$. The dried ether solution was concentrated and dissolved in chloroform (5 mL), cooled to $-10°$ gC., and mCPBA (0.974 g, 5.6 mmol) was added as a solid. The reaction was allowed to stir for 3 hours and then poured onto an alumina column pre-equilibrated with chloroform. The column was eluted first with chloroform (1 bed volume) to remove impurities and then with 10% methanol in chloroform (enough to remove all of the product). The fractions containing product were combined and concentrated. The resulting oil which contained some alumina was dissolved in water which formed a milky solution. Upon filtration through 0.22 mm syringe filter the solution clarified to a colorless solution which was lyophilized. The material was isolated as 163 mg (82%) of an oil that crystallized upon standing. IR (KBr): 3386 (br), 3259 (br), 2915, 1647 (C=O), 1550, 1488; $^1$H NMR (CDCl$_3$, 300 MHz): δ 0.910–1.853 (m, 27H); 2.016 (s, 2H); 3.219 (s, 6H); 3.329–3.415 (m, 4H); 7.564–7.581 (m, 1H) $^{13}$C NMR (CDCl$_3$, 75.4 MHz): δ 173.0 (C); 68.5 (CH$_2$); 58.6 (CH$_3$); 45.4 (CH$_3$); 44.1 (CH$_2$); 40.9 (C); 36.8 (CH$_2$); 33.4 (CH$_2$); 28.7 (CH$_2$); 27.2 (CH$_2$); 27.0 (CH$_2$); 26.7 (CH$_2$); 25.8 (CH$_2$); 23.2 (CH$_2$).

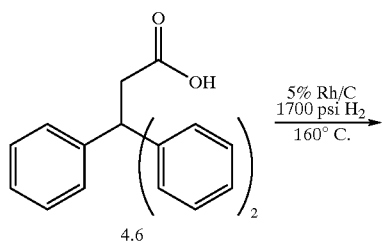

4.6

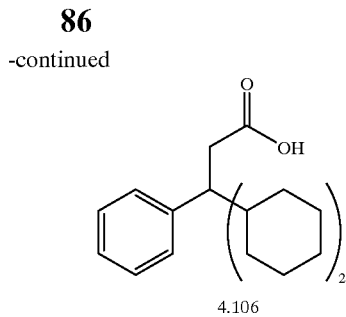

4.106

Preparation of 4.106. The acid 4.6 (1 g, 3.3 mmol) was dissolved in 20 mL of acetic acid and 5% rhodium on carbon (230 mg) was added along with a stir bar. The reaction mixture which was in a glass sleeve was placed in a small reaction bomb and the bomb was sealed. Hydrogen pressure of 1500 psi was charged into the bomb and the bomb was heated to 150° C. for 24 hours. The bomb was cooled and the solution was filtered over celite to remove the catalyst eluting with ethyl acetate. The solution was concentrated and chromatographed on a silica gel column eluting with 9:1 hexanes:ethyl acetate. The fractions containing product were pooled and concentrated yielding 104 mg (10%) of a crystalline solid. The crystals were X-ray quality and were submitted for crystallographic analysis. IR (KBr): 2935, 2848, 1700 (C=O), 698; $^1$H NMR (CDCl$_3$, 300 MHz): δ 0.750–2.275 (m, 22H); 2.878 (s, 2H); 7.120–7.326 (m, 5H); $^{13}$C NMR (CDCl$_3$, 75.4 MHz): δ 179.8 (C); 142.3 (C); 127.5 (CH); 127.0 (CH); 125.4 (CH); 50.6 (C); 41.8 (CH); 36.1 (CH$_2$); 27.9 (CH$_2$); 27.6 (CH$_2$); 27.5 (CH$_2$); 26.5 (CH$_2$); EI-MS m/z (M$^+$) calcd for C$_{21}$H$_{30}$O$_2$: 314.2246, obsd 314.2240.

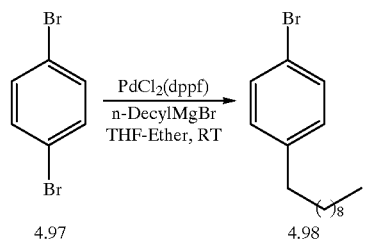

Preparation of 4.98. The dibromobenzene 4.97 (10 g, 42.2 mmol) was combined with the Pd (II) catalyst (350 mg, 4.24 mmol) in dry THF. To the solution was added decylmagnesium bromide (30 mL, 1.1 M in ether). Initially upon addition of the Grignard reagent, the solution turned orange and then turned to purple after addition of 2 mL of the Grignard reagent. The solution was allowed to stir for 1 hour at which time the reaction was cooled to 0° C. and quenched with methanol (2 mL) in hexanes (90 mL). The solution was filtered through a plug of silica gel eluting with hexanes. The filtrate was concentrated and the resulting oil was vacuum distilled (bp @ 155° C./2 torr). The reaction yielded 7 g (56%) of a clear colorless liquid. The material was taken on without characterization.

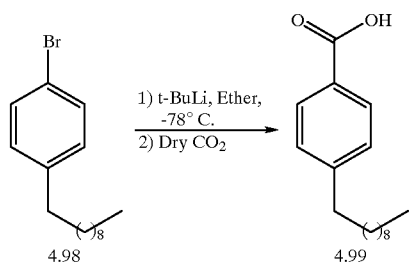

Preparation of 4.99. The bromide 4.98 was dissolved in dry ether and the solution was cooled to −78° C. The bromide was reacted with t-butyl lithium to affect a lithium-halogen exchange. The reaction was allowed to stir for 30 minutes. The lithium species was quenched with dry carbon dioxide. Dry carbon dioxide was prepared by adding dry ice to a flask which was fitted with a drying tube filled with fresh Dryrite. A syringe needle was connected to the drying tube and the carbon dioxide was bubbled into the reaction for 1 hour, while allowing the reaction to warm. The solution was poured over a ice/conc. HCl slurry and the precipitate was extracted with ether. The organic layers were combined and dried with $MgSO_4$. The dried solution was concentrated and the orange solid was chromatographed on silica eluting with 1.5:8.5 ethyl acetate:hexanes. The fractions containing product were concentrated and recrystallized with hexanes resulting in 3 g (47%) of white needles. IR (KBr): 2921, 2848, 1783 (C=O), 698; $^1$H NMR ($CDCl_3$, 300 MHz): δ 0.879 (t, J=7, 3H); 1.260–1.317 (m, 14H); 1.636 (p, J=7.5 Hz, 2H); 2.675 (t, J=7.5 Hz, 2H); 7.278 (d, J=8 Hz, 2H); 8.029 (d, J=8 Hz, 2H); $^{13}$C NMR ($CDCl_3$, 75.4 MHz): d 172.1 (C); 149.4 (C); 130.1 (CH); 128.3 (CH); 126.6 (CH); 36.9 ($CH_2$); 31.7 ($CH_2$); 30.9 ($CH_2$); 29.4 ($CH_2$); 29.2 ($CH_2$); 29.1 ($CH_2$); 29.0 ($CH_2$); 22.5 ($CH_2$); 13.9 ($CH_3$); EI-MS m/z ($M^+$) calcd for $C_{17}H_{27}O_2$: 263.2011, obsd 263.1952.

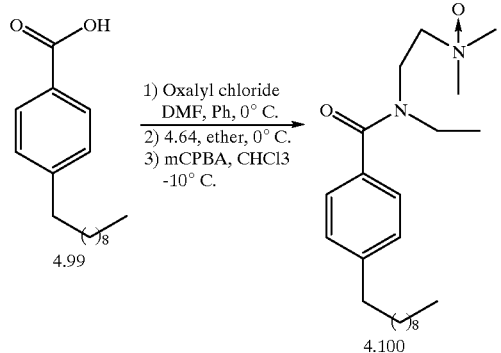

Preparation of 4.100. The acid 4.99 (300 mg, 1.141 mmol) was dissolved in 5 mL of benzene in a round bottom flask. One drop of DMF was added as a catalyst and the solution was cooled with an ice bath. Once the solution had cooled, oxalyl chloride (0.500 mL, 5.7 mmol) was added dropwise resulting in a vigorously bubbling solution. The reaction was allowed to stir 3 hours and the volatiles were removed under vacuum. The residue was dissolved in dry ether (15 mL), cooled to 0° C., and 4.64 (360 mL, 2.2 mmol) in ether (15 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 453 mg (100%) of a light yellow oil. The oil was dissolved in 5 mL of ether and the amine was precipitated by adding 4 N HCl in dioxane (0.285 mL) diluted in 5 mL of ether. The off-white solid was recrystallized from methylene chloride/hexanes. The hydrochloride salt (100 mg, 0.250 mmol) was dissolved in chloroform (5 mL) and cooled to 0° C. mCPBA (218 mg, 1.25 mmol) was added and the reaction was allowed to stir before being chromatographed on an alumina column eluting first with chloroform (250 mL) and then with 10% methanol in chloroform. The fractions containing product were combined and concentrated. The concentrated material was dissolved in water and filtered through a 0.22 mm filter to remove any alumina. The filtered solution was lyophilized yielding 94 mg (99%) of an off-white solid. IR (KBr): 3432, 2922, 2853, 1623 (C=O), 1467; $^1$H NMR ($CDCl_3$, 300 MHz): δ 0.880 (t, J=7, 3H); 1.176–1.290 (m, 17H); 1.609 (p, J=7.5 Hz, 2H); 2.624 (t, J=7.5 Hz, 2H); 3.249–3.413 (m, 8H); 3.641 (m, 2H); 4.035 (m, 2H); 7.197–7.296 (m, 4H); $^{13}$C NMR ($CDCl_3$, 75.4 MHz); δ 172.1 (C); 144.7 (C); 138.2 (CH); 126.1 (CH); 66.6 ($CH_2$); 58.9 ($CH_3$); 45.1 ($CH_2$); 40.5 ($CH_2$); 35.1 ($CH_2$); 31.6 ($CH_2$); 30.9 ($CH_2$); 29.3 ($CH_2$); 29.1 ($CH_2$); 28.9 ($CH_2$); 22.3 ($CH_2$); 13.9 ($CH_3$); 13.8 ($CH_3$); FAB-MS m/z ($M^+H^+$) calcd for $C_{23}H_{41}N_2O_2$ 377.5, obsd 377.3.

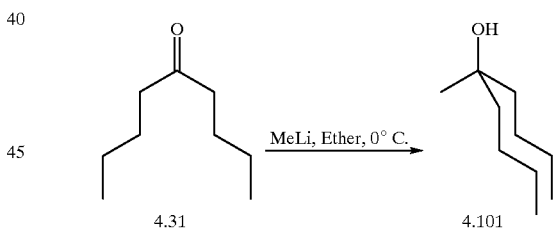

Preparation of 4.101. Ketone 4.31 (12.1 mL, 70.3 mmol) was placed into a flame dried round bottom flask which was then charged with ether (100 mL). The solution was cooled to 0° C. and MeLi (100 mL, 1.4 M, 140 mmol) was added dropwise. The material was allowed to stir for 1 h and was poured over ice water. The organic layer was washed with water twice. The organic layer was dried with $MgSO_4$, concentrated, and chromatographed on silica eluting with 9:1 hexanes:ethyl acetate. The reaction yielded 10 g (91%) of a clear colorless oil. IR (KBr): 3383 (O—H), 2956, 2932, 2861, 1467; $^1$H NMR ($CDCl_3$, 300 MHz): δ 0.916 (t, J=7, 6H); 1.152 (s, 3H); 1.274–1.466 (m, 12H); $^{13}$C NMR ($CDCl_3$, 75.4 MHz): δ 72.6 (C); 41.4 ($CH_2$); 26.8 ($CH_3$); 25.9 ($CH_2$); 23.1 ($CH_2$); 13.9 ($CH_3$).

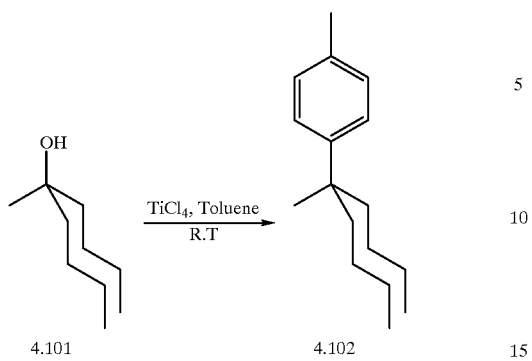

Preparation of 4.102. The alcohol 4.101 (5 g, 32 mmol) was dissolved in toluene (8 mL) in a flamed dried round bottom flask fitted with a condenser. The solution was allowed to stir as titanium tetrachloride (3.51 mL, 32 mmol) was added slowly. An orange-white precipitate was formed immediately after addition of the titanium tetrachloride along with the evolution of heat. The reaction was cooled with an ice bath if boiling became too violent. The reaction was allowed to stir for 1 hr. Dilute HCl was cautiously added to quench the reaction. The organic layer was separated and washed twice with dilute HCl and twice with water. The organic layer was dried with $MgSO_4$, concentrated and chromatographed on silica eluting with hexanes. The product was a clear colorless oil (6 g, 81%). IR (KBr): 2956, 2871, 1466 [1] H NMR ($CDCl_3$, 300 MHz): δ 0.916 (t, J=7, 6H); 1.004–1.466 (m, 15H); 2.344 (s, 3H); 7.081–7.177 (m, 4H); $^{13}C$ NMR ($CDCl_3$, 75.4 MHz): δ 145.2 (C); 134.2 (C); 128.4 (CH); 126.0 (CH); 42.9 ($CH_2$); 40.8 (C); 26.7 ($CH_2$); 23.9 ($CH_3$); 23.2 ($CH_2$); 20.6($CH_3$); 13.9($CH_3$); EI-MS m/z ($M^+$) calcd for $C_{17}H_{28}$: 232.2191, obsd 232.2198.

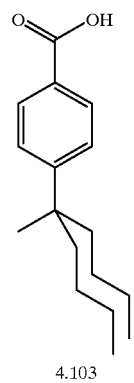

Preparation of 4.103. The $Co(acac)_2$ (11 mg, 0.0427 mmol) was placed into a flask containing acetic acid (17 mL), resulting in the formation of a light pink solution. The hydrophthalimide (7 mg, 0.0427 mmol) was added to the solution which was then heated in a steam bath for two minutes. An oxygen filled balloon was placed on the reaction and the solution turned violet. Hydrocarbon 4.102 (2 g, 8 mmol) was then added and the solution was refluxed for 17 hrs. The reaction was then removed from the steam bath and allowed to cool before extracting with hexanes four times (25 mL). The combined hexanes layers were then extracted with 1 N NaOH (15 mL) three times. The basic aqueous solution was acidified to pH 1 and extracted with ether (50 mL) three times. The organic layers were combined, dried with $MgSO_4$, and concentrated resulting in an off-white solid which was recrystallized from ethanol/water. The reaction yielded 687 mg (32%, 1st crop) of off-white needles. IR (KBr): 2957, 2858, 1683 (C=O),1466 $^1H$ NMR ($CDCl_3$, 300 MHz): δ 0.909 (t, J=7, 6H); 1.064–1.278 (m, 4H); 1.306 (s, 3H); 1.534–1.759 (m, 4H); 7.389 (d, J=7, 2H); 8.055 (d, J=7, 2H); 10.12 (br. s, 1H); $^{13}C$ NMR ($CDCl_3$, 75.4 MHz): δ 172.2 (C); 154.9 (C);129.6 (CH); 126.3 (CH); 126.0 (CH); 42.8 ($CH_2$); 41.1 (C); 26.1 ($CH_2$); 23.4 ($CH_3$); 23.0 ($CH_2$); 13.7 ($CH_3$); EI-MS m/z ($M^+H^+$) calcd for $C_{17}H_{26}O_2$: 263.2011, obsd 263.2012.

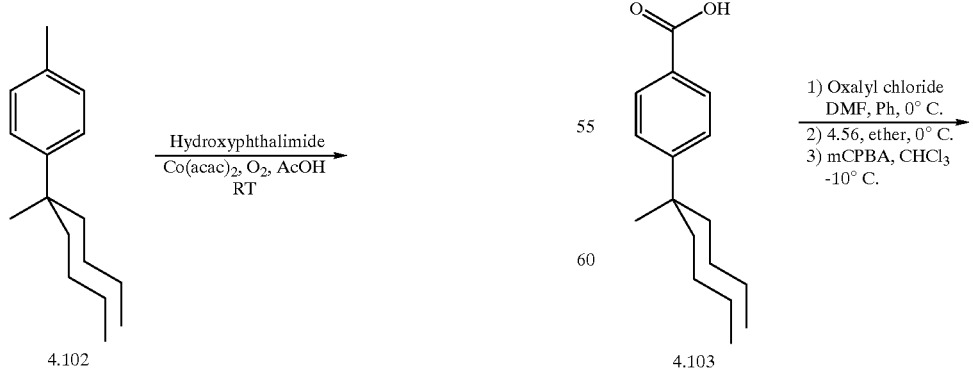

-continued

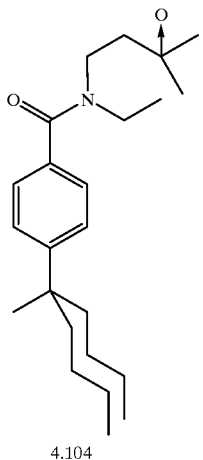

4.104

Preparation of 4.104. The acid 4.103 (300 mg, 1.141 mmol) was dissolved in 5 mL of benzene in a round bottom flask. One drop of DMF was added as a catalyst and the solution was cooled with an ice bath. Once the solution had cooled, oxalyl chloride (0.500 mL, 5.7 mmol) was added dropwise resulting in a vigorously bubbling solution. The reaction was allowed to stir 3 hours and the volatiles were removed under vacuum. The residue was dissolved in dry ether (15 mL), cooled to 0° C., and 4.64 (360 mL, 2.2 mmol) in ether (15 mL) was added dropwise resulting in a white precipitate. The solution was allowed to stir overnight. The next day 1 N NaOH (25 mL) was added and the precipitate dissolved. The ether solution was then washed twice more with 25 mL portions of 1 N NaOH. The ether layer was dried by first washing with saturated NaCl solution and then dried with either $Na_2SO_4$ or $MgSO_4$. The dried ether solution was concentrated yielding 453 mg (100%) of a light yellow oil. The oil was dissolved in 5 mL of ether and the amine was precipitated by adding 4 N HCl in dioxane (0.285 mL) diluted in 5 mL of ether. The off-white solid was recrystallized from methylene chloride/hexanes. The hydrochloride salt (100 mg, 0.250 mmol) was dissolved in chloroform (5 mL) and cooled to 0° C. mCPBA (218 mg, 1.25 mmol) was added and the reaction was allowed to stir before being chromatographed on an alumina column eluting first with chloroform (250 mL) and then with 10% methanol in chloroform. The fractions containing product were combined and concentrated. The concentrated material was dissolved in water and filtered through a 0.22 mm filter to remove any alumina. The filtered solution was lyophilized yielding 83 mg (87%) of a yellow oil. $^1$H NMR (CDCl$_3$, 300 MHz): δ 0.805 (t, J=7, 6H); 1.064–1.31 (m, 11H); 1.42–1.75 (m, 4H); (m, 4H); 3.29 (s, 6H); 3.25–3.68 (m, 4H); 4.05–4.15 (m, 2H); 7.3 (s, 4H); $^{13}$C NMR (CDCl$_3$, 75.4 MHz): δ 172.2 (C); 154.9 (C); 129.6 (CH); 126.3 (CH); 126.0 (CH); 42.8 (CH$_2$); 41.1 (C); 26.1 (CH$_2$); 23.4 (CH$_3$); 23.0 (CH$_2$); 13.7 (CH$_3$); EI-MS m/z (M$^+$CH$_3$) calcd for $C_{23}H_{40}N_2O_2$ 377.4, obsd 377.3.

Preparation of A.2.1. Acid 4.34 (705 mg, 2.68 mmol) was dissolved in freshly distilled THF (50 mL). Lithium aluminum hydride was added cautiously to the stirring solution. The suspension was refluxed for 3 hours. The reaction was cooled to room temperature and slowly quenched with a freshly prepared saturated aqueous solution of Na$_2$SO$_4$ (1 mL). The resulting white preciptate was removed by filtration and the filtrate was concentrated, resulting in a quantitative yield of pure product as a white solid. $^1$H-NMR (CDCl$_3$, 300 MHz): 0.855 (t, J=7, 6H); 1.038–1.078 (m, 4H); 1.246 (p, J=7, 4H); 1.295 (br.s., 1H); 1.622–1.677 (m, 4H); 1.974 (t, J=8, 2H); 3,472 (app. t, J=8, 2H); 7.260–7.324 (m, 5H); $^{13}$C NMR (CDCl$_3$, 74.5 M Hz); 146.9 (C), 127.7 (CH), 125.9 (CH), 125.1 (CH), 59.1 (CH$_2$), 41.6 (C), 40.4 (CH$_2$), 36.9 (CH$_2$), 25.2 (CH$_2$), 23.0 (CH$_2$), 13.7 (CH$_3$).

Preparation of A.2.2. O-peractylated Maltose (5 g, 6.86 mmol) was dissolved in N-methylpyrrolidinone (10 mL). Hydrazine acetate (948 mg, 10.2 mmol) was added and the solution was heated to 50° C. for 10 minutes. The solution was cooled and the material was placed onto a silica column and eluted with 1:1 hexanes:ethyl acetate. The fractions containing product were concentrated and the resulting clear oil (3.88 g, 5.69 mmol) was dissolved in dry methylene chloride (35 mL). Cesium carbonate (463 mg, 1.4 mmol) was added along with 10 crushed molecular sieves and the solution was stirred while trichloroacetonitrile (2.85 g, 28 mmol) was added. The resulting reaction was stirred overnight. The next day the sieves were filtered off using a celite plug. The filtrate was concentrated to an oil which was applied to a silica column which was eluted with 1:1 ethyl acetate:hexanes. The product fractions were concentrated to a clear oil which was taken on without characterization.

Preparation of A.2.3. The alcohol A.2.1 (680 mg, 2.76 mmol) and the trichloroacetimidate A.2.2. (2 g, 3.97 mmol) were combined in a round bottom flask. Benzene was added and evaporated off several times to azeotrope any residual water. The mixture was then evacuated overnight and the next day the mixture was dissolved in dry methylene chloride (25 mL). The solution was cooled to 4° C. and a solution of trifluorosulfonic acid (TfOH) (882 μL, 1.985 mmol) was added. The reaction was allowed to stir for 2.5 hours and was then quenched with a saturated aqueous solution of sodium bicarbonate. The organic layers were dried with MgSO$_4$, concentrated, and chromatographed on a silica column (eluting with 3:7 ethyl acetate:hexanes) yielding 653 mg (26%) of the product as a white solid. The material was carried on without characterization.

Preparation of A.2.4. The O-peractylated maltoside A.2.3 (660 mg, 0.724 mmol) was dissolved in dry methanol. A small chunk of freshly cut sodium was added and the reaction was allowed to stir at room temperature for 5 hours. The solution was neutralized with the acidic ion-exchange resin amberlite IR 120. The resin was filtered off and the solution was concentrated to provide pure product (414 mg, 100%). $^1$H NMR (CDCl$_3$/d$_3$-MeOD, 300 MHz): 0.8 (m, 6H); 1.038–1.078 (m, 4H); 1.208–1.205 (m, 4H); 1.208–1.205 (m, 4H); 1.602–1.655 (m, 4H); 2.05 (m, 2H); 3.25–3.8 (m, 14H); 4.2 (m, 1H), 4.5 (br s, 7H), 5.15 (br s, 1H); 7.260–7.324 (M, 5H); $^{13}$C NMR (CDCl$_3$, 74.5 M Hz); 146.6 (C), 127.4 (CH), 125.4 (CH), 124.9 (CH), 102.5 (CH), 101.2 (CH), 79.5 (CH), 77.4 (CH), 76.9 (CH), 76.5 (CH), 75.8 (CH), 74.5 (CH), 73.2 (CH), 72.7 (CH), 72.1 (CH), 69.7 (CH), 60.1 (CH$_2$), 41.3 (C), 37.1 (CH$_2$), 36.6 (CH$_2$), 36.4 (CH$_2$), 25.0 (CH$_2$), 22.8 (CH$_2$), 13.7 (CH$_3$). FAB-MS m/z (M+, Na+), 595.2.

Determination of CMC

The CMC of a detergent can be determined experimentally by measuring the solubilization of a water-insoluble dye or fluorophore while varying the concentration of detergent. CMC may also be determined by measuring the diminution of the surface tension of an aqueous solution as a function of detergent concentration. (CMC's determined by either method correlate with each other.) The CMC is determined by extrapolating the plot of solubilization vs. concentration (or surface tension vs. concentration) in the two linear regions above and below the CMC. Where the two lines intersect is the CMC. In this Example, CMC's were determined by the method of Nugebauer, J. M. (1990), *Methods in Enzymology*, 182:239–253:

Tripod solutions in aqueous solutions containing 25 mM sodium phosphate pH 6.9 were prepared and transferred to screw-capped vials, and 1 mL of a 1,6-diphenylhexatriene solution (DPH, 3.125 mM DPH in THF) was added. The solutions were vortexed at room temperature for 30 seconds. The solutions were placed into a 3 mm×3mm quartz cell and the fluorescence spectrum was obtained (excitation 358 nm, emission 430 nm, excitation slit width=1 mm, emission slit width=20 nm, PMT voltage=700). The fluorescence intensity of each sample was plotted against amphiphile concentration. The CMC was determined by the intersection of the lines formed by linear regressions calculated for the concentrations that did not show fluorescence and those that did. The data points immediately surrounding the CMC were not considered due to non-linear behavior. See Tables 1 and 2, above, for the results.

Solubilization of Bacteriorhodopsin (BR) from Purple Membrane (PM)

BR is a membrane protein produced by halophilic archea from the genus Halobacterium. BR is highly expressed under anaerobic conditions and uses light energy to pump protons from inside the cell to outside the cell. The protein gradient generated by BR is used to synthesize adenosine triphosphate (ATP). BR consists of seven transmembrane helices that bundle together to form a center pore that contains the chromophore retinal.

BR resides in a two-dimensional lattice composed of trimers of BR arranged in a hexagonal pattern. The lattice is referred to as the purple membrane (PM) and can be seen by electron microscopy to form crystalline patches on the surface of the *H. salinerium* cell. The purple color results from the bound retinal chromophore. The retinal provides a useful spectral handle for monitoring the protein's solubility and stability in the presence of a detergent. In the PM, the bound retinal absorbs 570 nm light. Triton X-100-solubilized BR has a 10 nm blue shifted retinal absorbance.

We used BR solubilization from the PM to evaluate tripod detergents synthesized using the modular synthetic approach described above. The retinal chromophore of BR allowed us to quantify solubilized material by UV. Solubilized BR is defined as the intact protein left in the supernatant after a sample is centrifuged for 30 minutes at 300,000 g. The percent BR solubilized is determined by dividing the absorbance of the supernatant by the absorbance of the solution before centrifugation.

Solubilization experiments were conducted by making a series of solutions with constant concentration of PM and varying the concentration of detergent. The samples were mixed on a nutating table (used to gently mix a sample) for 24 hours in the dark. The absorbance at the $\lambda_{max}$ (between 540 nm and 570 nm) was then measured, and immediately afterward the samples were centrifuged for 30 minutes at 300,000 g. The supernatant was carefully removed so as not to disturb pelleted material. Absorbance measurements were made again, and the ratio of the supernatant absorbance to the absorbance before centrifugation provided the percent solubilization.

Tripod detergents 4.65 and 4.66 were tested in this fashion and shown to solubilize BR from the PM quite rapidly. To measure whether the solublized BR was present in a monomeric state, CD spectra of the supernatants were taken. When suspended within the native PM, BR yields a distinct sigmoidal CD spectrum due to exciton coupling between adjacent retinal chromophores. It has been shown that the strength of the exciton coupling is directly proportional to the concentration of retinal chromophore in the PM. Because the exciton coupling requires retinals to be held in a fixed geometry (as when suspended in the PM), the solubilization of BR can be measured in terms of the loss of exciton coupling. For compounds 4.65 and 4.66, the rate of solubilization of BR at room temperature was too rapid to monitor the loss of exciton coupling. Exciton coupling was completely gone after less than 10 minutes for samples solubilized by 4.65 and 4.66, a time period which is faster than the time required to obtain a CD spectrum. In comparison, Triton X-100 is effective at solubilizing BR, but takes 24 hours to so do at pH 6.9, and 49 hours at pH 5.

It is understood that the invention is not confined to the particular reagents, reactions, and protocols illustrated and described hereinabove, but embraces all modified and equivalent forms thereof as fall within the scope of the attached claims.

What is claimed is:

1. Amphiphilic compounds comprising Formula I:

Formula I:

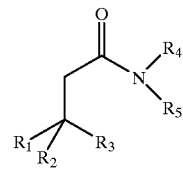

wherein $R_1$, $R_2$, and $R_3$ are independently selected from the group consisting of $C_2$–$C_{12}$ straight or branched alkyl; unsubstituted phenyl, biphenyl, $C_3$–$C_8$ cycloalkyl, and $C_3$–$C_8$ cycloalkenyl; and phenyl, biphenyl, $C_3$–$C_8$ cycloalkyl, and $C_3$–$C_8$ cycloalkenyl substituted with one, two, or three $C_1$–$C_6$ straight or branched alkyl groups; or $R_1$ and $R_2$ combined are selected from the group consisting of $C_3$–$C_8$ cycloalkyl, $C_3$–$C_8$ cycloalkenyl; and $C_3$–$C_8$ cycloalkyl and $C_3$–$C_8$ cycloalkenyl substituted with one, two, or three $C_1$–$C_6$ straight or branched alkyl groups;

one of $R_4$ or $R_5$ is selected from the group consisting of $C_2$–$C_6$-straight or branched alkyl-(dimethyl-N-oxide), alkyl-(dimethylamine), alkyl-(trimethylammonium), alkyl-glucosyl, alkyl-maltosyl, glucosyl, maltosyl, and polyethylene(glycosyl);

the other of $R_4$ or $R_5$ is selected from the group consisting of H, $C_2$–$C_6$ straight or branched alkyl or alkenyl, $C_2$–$C_6$-straight or branched alkyl-(dimethyl-N-oxide); alkyl-(dimethylamine), alkyl-(trimethylammonium), alkyl-glucosyl, alkyl-maltosyl, glucosyl, maltosyl, and polyethylene(glycosyl);

and salts thereof.

2. The compounds of claim 1, wherein $R_1$ and $R_2$ are combined.

3. The compounds of claim 2, wherein $R_3$ is $C_2$–$C_{12}$ straight or branched alkyl.

4. The compounds of claim 2, wherein $R_3$ is unsubstituted or substituted phenyl.

5. The compounds of claim 2, wherein $R_3$ is unsubstituted or substituted biphenyl.

6. The compounds of claim 2, wherein $R_3$ is unsubstituted or substituted $C_3$–$C_8$ cycloalkyl.

7. The compounds of claim 2, wherein $R_3$ is unsubstituted or substituted $C_3$–$C_8$ cycloalkenyl.

8. The compounds of claim 2, wherein $R_4$ and $R_5$ are $C_2$–$C_6$-straight or branched alkyl-(dimethyl-N-oxide).

9. The compounds of claim 2, wherein $R_4$ is a $C_2$–$C_6$-straight or branched alkyl-(dimethyl-N-oxide) and $R_5$ is a $C_2$–$C_6$ straight or branched alkyl or alkenyl.

10. The compounds of claim 2, wherein $R_4$ is glucosyl or maltosyl.

11. The compounds of claim 1, wherein $R_1$, $R_2$, and $R_3$, are $C_2$–$C_{12}$ straight or branched alkyl.

12. The compounds of claim 1, wherein $R_1$, $R_2$, and $R_3$, are unsubstituted or substituted phenyl.

13. The compounds of claim 1, wherein $R_1$, $R_2$, and $R_3$, are unsubstituted or substituted biphenyl.

14. The compounds of claim 1, wherein $R_1$, $R_2$, and $R_3$, are unsubstituted or substituted $C_3$–$C_8$ cycloalkyl.

15. The compounds of claim 1, wherein $R_1$, $R_2$, and $R_3$, are unsubstituted or substituted $C_3$–$C_8$ cycloalkenyl.

16. The compounds of claim 1, wherein $R_4$ is glucosyl or maltosyl.

17. A method of solubilizing a protein comprising treating the protein with an amphiplhilic compound as recited in claim 1.

* * * * *